United States Patent
Lu et al.

(10) Patent No.: US 8,945,943 B2
(45) Date of Patent: *Feb. 3, 2015

(54) PERSONAL GLUCOSE METERS FOR DETECTION AND QUANTIFICATION OF A BROAD RANGE OF ANALYTES

(75) Inventors: Yi Lu, Champaign, IL (US); Yu Xiang, Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/699,578

(22) PCT Filed: May 26, 2011

(86) PCT No.: PCT/US2011/038103
§ 371 (c)(1),
(2), (4) Date: Nov. 21, 2012

(87) PCT Pub. No.: WO2011/150186
PCT Pub. Date: Dec. 1, 2011

(65) Prior Publication Data
US 2013/0065224 A1 Mar. 14, 2013

Related U.S. Application Data

(60) Provisional application No. 61/348,615, filed on May 26, 2010.

(51) Int. Cl.
*G01N 33/558* (2006.01)
*C12Q 1/34* (2006.01)
*C12Q 1/54* (2006.01)

(52) U.S. Cl.
CPC ............... *G01N 33/558* (2013.01); *C12Q 1/34* (2013.01); *C12Q 1/54* (2013.01)
USPC ........... 436/514; 436/518; 436/524; 436/528; 435/283.1; 435/287.1; 435/7.1; 435/287.2; 435/287.7; 435/287.9; 435/14

(58) Field of Classification Search
USPC ............ 436/518, 524, 528; 435/283.1, 287.1, 435/7.1, 287.2, 287.7, 14
See application file for complete search history.

(56) References Cited

U.S. PATENT DOCUMENTS 3,839,153 A 10/1974 Schuurs et al.
4,463,090 A * 7/1984 Harris ........................... 435/7.7

(Continued)

FOREIGN PATENT DOCUMENTS

CA 2 364 288 A1 2/2000
EP 0 335 167 A1 10/1989

(Continued)

OTHER PUBLICATIONS

Balasubrananian et al., "Interferon-γInhibitory Oligodeoxynucleotides Alter the Confirmation of Interferon-γ," *Mol. Pharmacol.* 53:926-932, 1998.

(Continued)

*Primary Examiner* — Melanie Y Brown
(74) *Attorney, Agent, or Firm* — Klarquist Sparkman, LLP

(57) ABSTRACT

A general methodology for the development of highly sensitive and selective sensors that can achieve portable, low-cost and quantitative detection of a broad range of targets using only a personal glucose meter (PGM) is disclosed. The method uses recognition molecules that are specific for a target agent, enzymes that can convert an enzyme substrate into glucose, and PGM. Also provided are sensors, which can include a solid support to which is attached a recognition molecule that permits detection of a target agent, wherein the recognition molecule specifically binds to the target agent in the presence of the target agent but not significantly to other agents as well as an enzyme that can catalyze the conversion of a substance into glucose, wherein the enzyme is attached directly or indirectly to the recognition molecule, and wherein in the presence of the target agent the enzyme can convert the substance into glucose. The disclosed sensors can be part of a lateral flow device. Methods of using such sensors for detecting target agents are also provided.

35 Claims, 22 Drawing Sheets

(56) References Cited

U.S. PATENT DOCUMENTS

| | | | |
|---|---|---|---|
| 4,533,493 A | | 8/1985 | Benovic et al. |
| 4,861,711 A | | 8/1989 | Friesen et al. |
| 4,959,305 A | * | 9/1990 | Woodrum ............... 435/7.7 |
| 5,177,012 A | | 1/1993 | Kim et al. |
| 5,229,073 A | | 7/1993 | Luo et al. |
| 5,374,533 A | | 12/1994 | Matsuzawa et al. |
| 2003/0207332 A1 | * | 11/2003 | Sakaino et al. ............ 435/7.1 |
| 2006/0019406 A1 | | 1/2006 | Wei et al. |
| 2006/0177855 A1 | * | 8/2006 | Utermohlen et al. ......... 435/6 |
| 2006/0292561 A1 | * | 12/2006 | Li et al. ..................... 435/6 |
| 2007/0037153 A1 | | 2/2007 | Mandrand et al. |
| 2009/0298094 A1 | * | 12/2009 | Kohara et al. ............ 435/7.9 |
| 2009/0298191 A1 | * | 12/2009 | Whitesides et al. ........ 436/164 |

FOREIGN PATENT DOCUMENTS

| | | |
|---|---|---|
| EP | 1 884 766 A1 | 2/2008 |
| IN | 191 604 A1 | 12/2003 |

OTHER PUBLICATIONS

Boehm et al., "Cellular Responses to Interferon-γ," *Annu. Rev. Immunol.* 15:749-795, 1997.

Breaker and Joyce, "A DNA Enzyme that Cleaves RNA," *Chem. Biol.* 1:223-229, 1994.

Breaker, "Engineered Allosteric Ribozymes as Biosensor Components," *Curr. Opin. Biotechnol.* 13:31-39, 2002.

Brown et al., "Biochemical Characterization of a Uranyl Ion-Specific DNAzyme," *ChemBioChem* 10:486-492, 2009.

Carmi et al., "In Vitro Selection of Self-Cleaving DNAs," *Chem. Biol.* 3:1039-1046, 1996.

Chen and He, "Selective Recognition of Metal Ions by Metalloregulatory Proteins," *Curr. Opin. Chem. Biol.* 12:214-221, 2008.

Danielli et al., "Magnetic Modulation Biosensing for Rapid and Homogeneous Detection of Biological Targets at Low Concentrations," *Curr. Pharm. Biotechnol.* 11:128-137, 2010.

Drummond et al., "Electrochemical DNA Sensors," *Nat. Biotechnol.* 21:1192-1199, 2003.

Ellington and Szostak, "In Vitro Selection of RNA Molecules That Bind Specific Ligands," *Nature* 346:818-822, 1990.

Freeman et al., "Supramolecular Cocaine—Aptamer Complexes Activate Biocatalytic Cascades," *J. Am. Chem. Soc.* 131:5028-5029, 2009.

Huang et al., "Aptamer-Modified Gold Nanoparticles for Colorimetric Determination of Platelet-Derived Growth Factors and Their Receptors," *Anal. Chem.* 77:5735-5741, 2005.

Huizenga and Szostak, "A DNA Aptamer That Binds Adenosine and ATP," *Biochem.* 34:656-665, 1995.

Koshland and Stein, "Correlation of Bond Breaking with Enzyme Specificity. Cleavage Point of Invertase," *J. Biol. Chem.* 208:139-148, 1954.

Lee et al., "An Oligonucleotide Blocks Interferon-[gamma] Signal Transduction," *Transplantation* 62:1297-1301, 1996.

Lee et al., "Aptamer Database," *Nucleic Acids Res.* 32:D95-D100, 2004.

Lee et al., "Colorimetric Detection of Mercuric Ion ($Hg^{2+}$) in Aqueous Media Using DNA-Functionalized Gold Nanoparticles," *Angew. Chem. Int. Ed.* 46:4093-4096, 2007.

Lee, "Over-the-Counter Biosensors: Past, Present, and Future," *Sensors* 8:5535-5559, 2008.

Lee et al., "Highly Sensitive and Selective Colorimetric Sensors for Uranyl ($UO_2^{2+}$): Development and Comparison of Labeled and Label-Free DNAzyme-Gold Nanoparticle Systems," *J. Am. Chem. Soc.* 130:14217-14226, 2008.

Liu and Lu, "A Colorimetric Lead Biosensor Using DNAzyme-Directed Assembly of Gold Nanoparticles," *J. Am. Chem. Soc.* 125:6642-6643, 2003.

Liu and Lu, "Colorimetric Biosensors Based on DNAzyme-Assembled Gold Nanoparticles," *J. Fluoresc.* 14:343-354, 2004.

Liu and Lu, "Fast Colorimetric Sensing of Adenosine and Cocaine Based on a General Sensor Design Involving Aptamers and Nanoparticles," *Angew. Chem. Int. Ed.* 45:90-94, 2006.

Liu and Lu, "Fluorescent DNAzyme Biosensors for Metal Ions Based on Catalytic Molecular Beacons," *Methods Mol. Biol.* 335:275-288, 2006.

Liu et al., "A Catalytic Beacon Sensor for Uranium with Parts-Per-Trillion Sensitivity and Millionfold Selectivity," *Proc. Nat. Acad. Sci. U.S.A.* 104:2056-2061, 2007.

Liu et al., "Development of a Monoclonal Antibody Against Ochratoxin A and Its Application in Enzyme-Linked Immunosorbent Assay and Gold Nanoparticle Immunochromatographic Strip," *Anal. Chem.* 80:7029-7035, 2008.

Liu et al., "Functional Nucleic Acid Sensors," *Chem. Rev.* 109:1948-1998, 2009.

Liu et al., "A Simple and Sensitive "Dipstick" Test in Serum Based on Lateral Flow Separation of Aptamer-Linked Nanostructures," *Angew. Chem. Int. Ed.* 45:7955-7959, 2006.

Montagnana et al., "Overview on Self-Monitoring of Blood Glucose," *Clin. Chim. Acta* 402:7-13, 2009.

Navani and Li, "Nucleic Acid Aptamers and Enzymes as Sensors," *Curr. Opin. Chem. Biol.* 10:272-281, 2006.

Ngundi et al., "Array Biosensor for Detection of Ochratoxin A in Cereals and Beverages," *Anal. Chem.* 77:148-154, 2005.

Niemeyer, "The Developments of Semisynthetic DNA-Protein Conjugates," *Trends Biotechnol.* 20:395-401, 2002.

Niemeyer, "Functional Devices from DNA and Proteins," *Nano Today* 2:42-52, 2007.

Niemeyer, "Semisynthetic DNA-Protein Conjugates for Biosensing and Nanofabrication," *Angew. Chem. Int. Ed.* 49:1200-1216, 2010.

Nolan and Lippard, "Tools and Tactics for the Optical Detection of Mercuric Ion," *Chem. Rev.* 108:3443-3480, 2008.

Nutiu and Li, "Structure-Switching Signaling Aptamers," *J. Am. Chem. Soc.* 125:4771-4778, 2003.

Nutiu and Li, "In Vitro Selection of Structure-Switching Signaling Aptamers," *Angew. Chem. Int. Ed.* 44, 1061-1065, 2005.

Nutiu and Li, "Aptamers with Fluorescence-Signaling Properties," *Methods* 37:16-25, 2005.

Ono and Togashi, "Highly Selective Oligonucleotide-Based Sensor for Mercury(II) in Aqueous Solutions," *Angew. Chem. Int. Ed.* 43:4300-4302, 2004.

Pai et al., "Interferon-γ Assays in the Immunodiagnosis of Tuberculosis: A Systematic Review," *Lancet Infect. Dis.* 4:761-776, 2004.

Pfohl-Leszkowicz and Manderville, "Ochratoxin A: An Overview on Toxicity and Carcinogenicity in Animals and Humans," *Mol. Nutr. Food Res.* 51:61-99, 2007.

Pohland et al., "Ochratoxin A: A Review," *Pure Appl. Chem* 64:1029-1046, 1992.

Que et al., "Metals in Neurobiology: Probing Their Chemistry and Biology with Molecular Imaging," *Chem. Rev* 108:1517-1549, 2008.

Que and Chang, "Responsive Magnetic Resonance Imaging Contrast Agents as Chemical Sensors for Metals in Biology and Medicine," *Chem. Soc. Rev.* 39:51-60, 2010.

Rajendran and Ellington, "Selecting Nucleic Acids for Biosensor Applications," *Comb. Chem. High Throughput Screening* 5:263-270, 2002.

Reddy and Maley, "Identification of an Active-Site Residue in Yeast Invertase by Affinity Labeling and Site-Directed Mutagenesis," *J. Biol. Chem.* 265:10817-10820, 1990.

Reddy and Maley, "Studies on Identifying the Catalytic Role of Glu-204 in the Active Site of Yeast Invertase," *J. Biol. Chem.* 271:13953-13958, 1996.

Sefah et al., "Nucleic Acid Aptamers for Biosensors and Bio-Analytical Applications," *Analyst* 134:1765-1775, 2009.

Song et al., "Aptamer-Based Biosensors," *Trends Anal. Chem.* 27:108-117, 2008.

Swensen et al., "Continuous, Real-Time Monitoring of Cocaine in Undiluted Blood Serum via a Microfluidic, Electrochemical Aptamer-Based Sensor," *J. Am. Chem. Soc.* 131:4262-4266, 2009.

Tamanaha et al., "Magnetic Labeling, Detection, and System Integration," *Biosens. Bioelectron.* 24:1-13, 2008.

Tan et al., "Molecular Beacons," *Curr. Opin. Chem. Biol.* 8:547-553, 2004.

(56) References Cited

OTHER PUBLICATIONS

Tuerk and Gold, "Systematic Evolution of Ligands by Exponential Enrichment: RNA Ligands to Bacteriophage T4 DNA Polymerase," Science 249:505-510, 1990.

Tuleuova et al., "Development of an Aptamer Beacon for Detection of Interferon-Gamma," Anal. Chem. 82:1851-1857, 2010.

Wang et al., "Magnetic Bead-Based Label-Free Electrochemical Detection of DNA Hybridization," Analyst 126:2020-2024, 2001.

Wang et al., "Metal Nanoparticle-Based Electrochemical Stripping Potentiometric Detection of DNA Hybridization," Anal. Chem. 73:5576-5581, 2001.

Wang and Musameh, "Carbon Nanotube/Teflon Composite Electrochemical Sensors and Biosensors," Anal. Chem. 75:2075-2079, 2003.

Willner and Zayats, "Electronic Aptamer-Based Sensors," Angew. Chem. Int. Ed. 46:6408-6418, 2007.

Willner et al., "DNAzymes for Sensing, Nanobiotechnology and Logic Gate Applications," Chem. Soc. Rev. 37:1153-1165, 2008.

Wu et al., "Terminal Protection of Small-Molecule-Linked DNA for Sensitive Electrochemical Detection of Protein Binding via Selective Carbon Nanotube Assembly," J. Am. Chem. Soc. 131:12325-12332, 2009.

Xiang et al., "Abasic Site-Containing DNAzyme and Aptamer for Label-Free Fluorescent Detection of Pb2+ and Adenosine with High Sensitivity, Selectivity, and Tunable Dynamic Range," J. Am. Chem. Soc. 131:15352-15357, 2009.

Xiang and Lu, "Using Personal Glucose Meters and Functional DNA Sensors to Quantify a Variety of Analytical Targets," Nat. Chem. 3:697-703, 2011.

Xiang and Lu, "Using Commercially Available Personal Glucose Meters for Portable Quantification of DNA," Anal. Chem. 84:1975-1980, 2012.

Xiang and Lu, "Portable and Quantitative Detection of Protein Biomarkers and Small Molecular Toxins Using Antibodies and Ubiquitous Personal Glucose Meters," Anal. Chem. Mar. 20, 2012 [Epub ahead of print] (Abstract).

Xiao et al., "Electrochemical Detection of Parts-Per-Billion Lead via an Electrode-Bound DNAzyme Assembly," J. Am. Chem. Soc. 129:262-263, 2007.

Xu et al., "Ultrasensitive and Selective Colorimetric DNA Detection by Nicking Endonuclease Assisted Nanoparticle Amplification," Angew. Chem. Int. Ed. 48:6849-6852, 2009.

Xue et al., "One-Step, Room Temperature, Colorimetric Detection of Mercury (Hg2+) Using DNA/Nanoparticle Conjugates," J. Am. Chem. Soc. 130:3244-3245, 2008.

Yigit et al., "MRI Detection of Thrombin with Aptamer Functionalized Superparamagnetic Iron Oxide Nanoparticles," Bioconjugate Chem. 19:412-417, 2008.

Yu et al., "Comparison of Enzyme-Linked Immunosorbent Assays with Chemiluminescent and Colorimetric Detection for the Determination of Ochratoxin A in Food," J. Agric. Food. Chem 59:809-813, 2011.

Zhao et al., "Design of Gold Nanoparticle-Based Colorimetric Biosensing Assays," ChemBioChem 9:2363-2371, 2008.

Zuo et al., "A Target-Responsive Electrochemical Aptamer Switch (TREAS) for Reagentless Detection of Nanomolar ATP," J. Am. Chem. Soc. 129:1042-1043, 2007.

Zuo et al., "High Specificity, Electrochemical Sandwich Assays Based on Single Aptamer Sequences and Suitable for the Direct Detection of Small-Molecule Targets in Blood and Other Complex Matrices," J. Am. Chem. Soc. 131:6944-6945, 2009.

Li, Y.; Lu, Y. *Functional Nucleic Acids for Sensing and Other Analytical Applications*; Springer: New York, 2009.

Ishikawa, "Enzyme Immunoassay of Insulin by Fluorimetry of the Insulin-glucoamylase Complex," *J. Biochem.* 73:1319-1321, 1973.

Nanda et al., "Thermostable α-Amylase Conjugated Antibodies as Probes for Immunodetection in Elisa," *J. Immunoassay Immunochem.* 23:327-345, 2002.

Tsuji et al., "Chemiluminescent Enzyme Immunoassay A Review," *Anal. Sci.* 5:497-506-1989.

Sigma, MSDS Sucrose, pp. 1-6, 2013, tetrieved from: http://www.sigmaaldrich.com/MSDS/MSDS/DisplayMSDSPage.do?country-US&language=en&productNumber=S8501&brand=SIGMA&PageToGoToURL=URL=http%3A%2F%www.sigmaaldrich.com%2Fcatalog%2Fproduct%2Fsigma%sFs8501%3Flang%3Den retrieved on Jan. 3, 2014.

\* cited by examiner

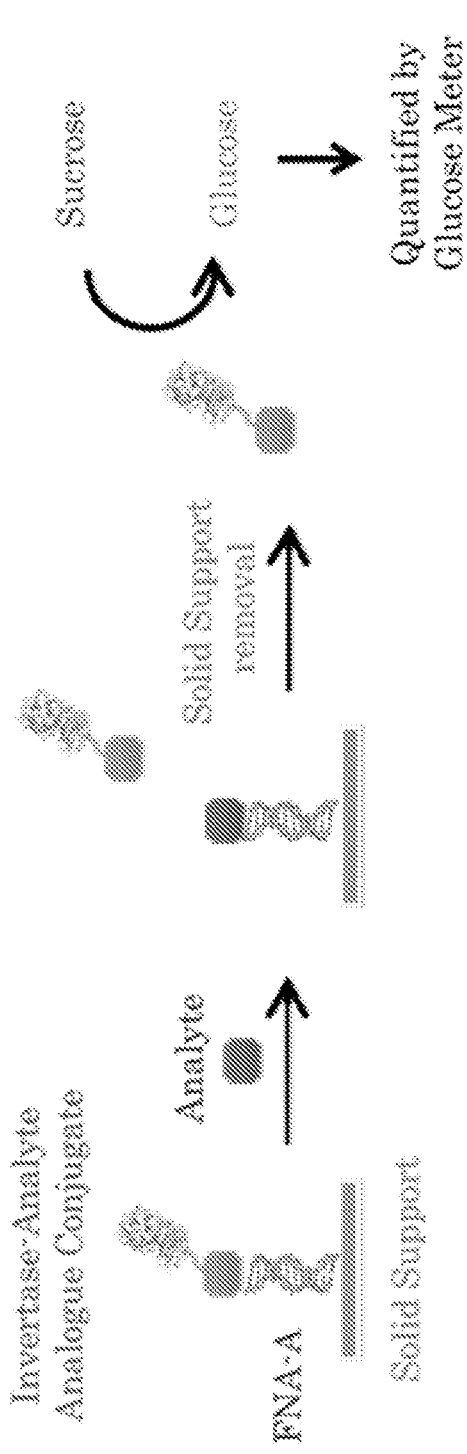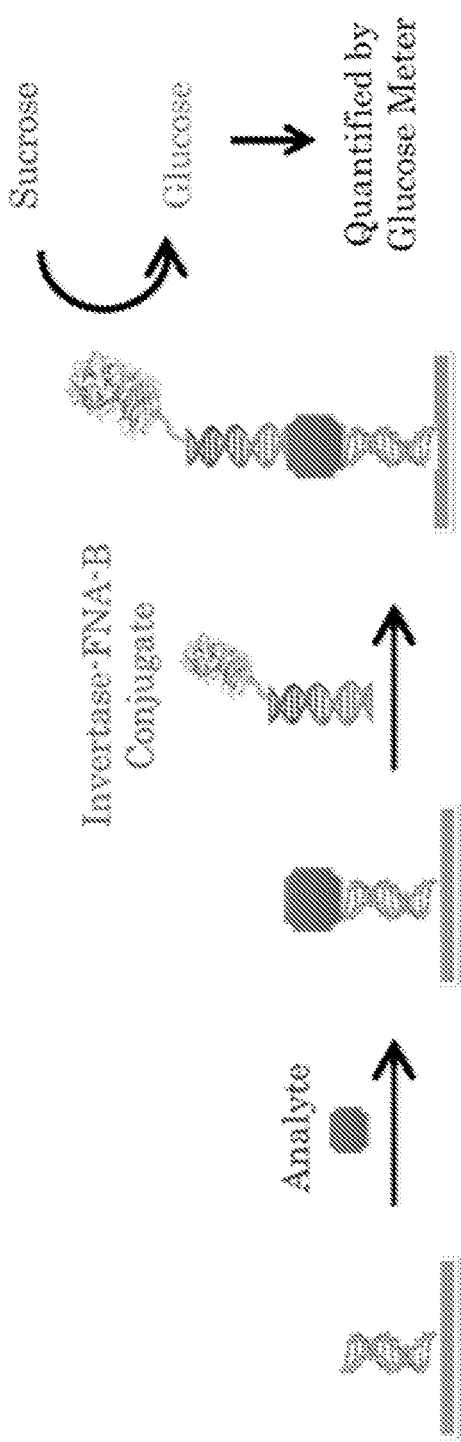

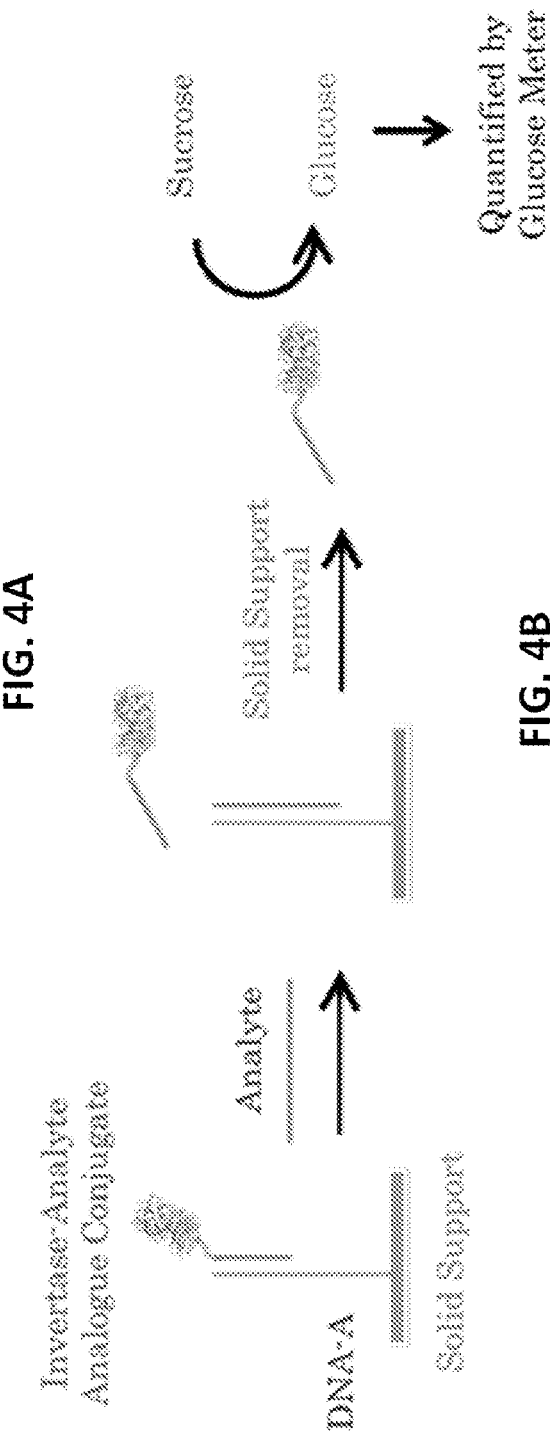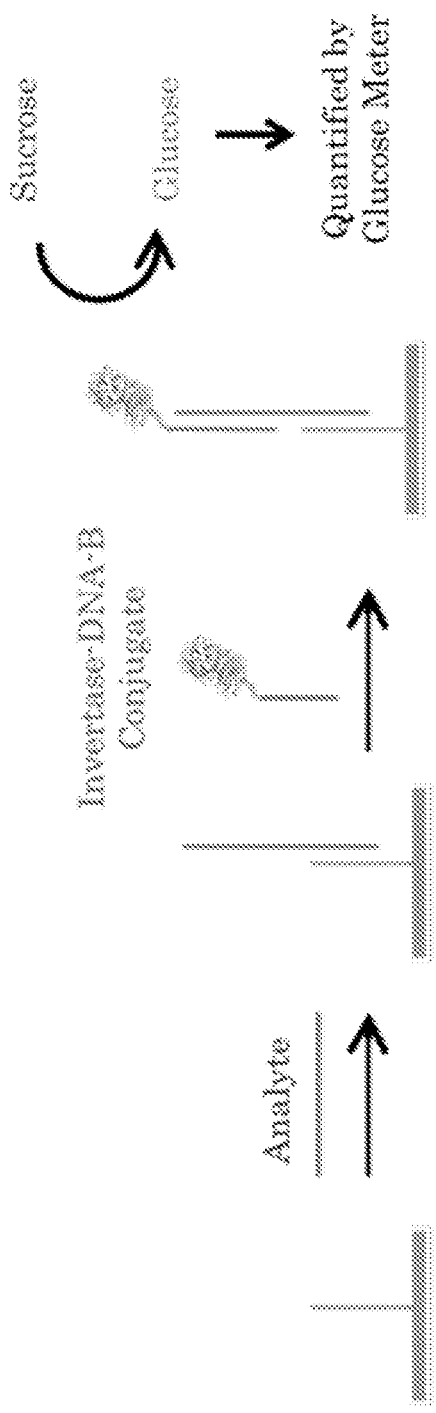
FIG. 4A
FIG. 4B

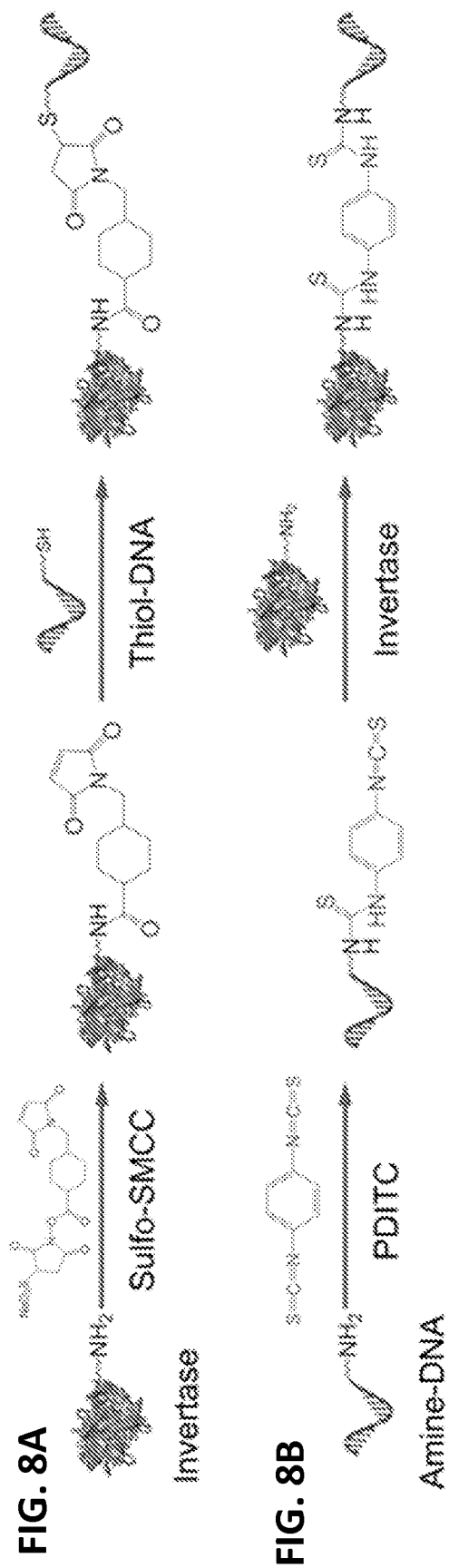

FIG. 11
Cocaine aptamer control
Adensoine aptamer control
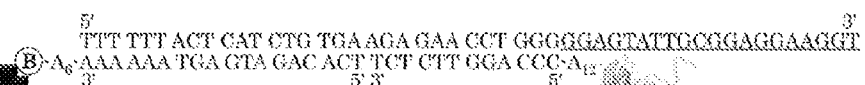
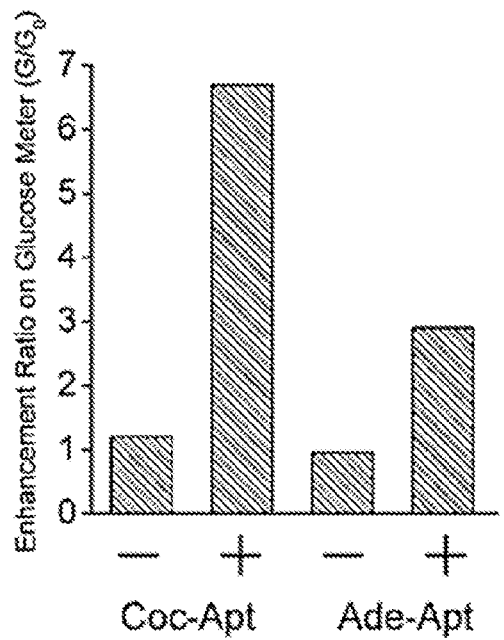

SEQUENCE LISTING

```
<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: biotin-modified DNA

<400> SEQUENCE: 1
tcacagatga gtaaaaaaaa aaaa                                              24

<210> SEQ ID NO 2
<211> LENGTH: 24
<212> TYPE: DNA
<213> ORGANISM: Artificial Sequence
<220> FEATURE:
<223> OTHER INFORMATION: thiol-modified DNA

<400> SEQUENCE: 2
aaaaaaaaaa aagtctcccg agat                                              24

<210> SEQ ID NO 3
<211> LENGTH: 24
<212> TYPE: DNA
<213> ORGANISM: Artificial Sequence
<220> FEATURE:
<223> OTHER INFORMATION: amine-modified DNA

<400> SEQUENCE: 3
aaaaaaaaaa aacccaggtt ctct                                              24

<210> SEQ ID NO 4
<211> LENGTH: 62
<212> TYPE: DNA
<213> ORGANISM: Artificial Sequence
<220> FEATURE:
<223> OTHER INFORMATION: Cocaine aptamer

<400> SEQUENCE: 4 tttttactc atctgtgaat ctcgggagac aaggataaat ccttcaatga agtgggtctc         60
cc                                                                      62

<210> SEQ ID NO 5
<211> LENGTH: 30
<212> TYPE: DNA
```

```
<213> ORGANISM: Artificial Sequence
<220> FEATURE:
<223> OTHER INFORMATION: Cocaine aptamer control

<400> SEQUENCE: 5 tttttttactc atctgtgaat ctcgggagac                                       30

<210> SEQ ID NO 6
<211> LENGTH: 50
<212> TYPE: DNA
<213> ORGANISM: Artificial Sequence
<220> FEATURE:
<223> OTHER INFORMATION: adenosine aptamer

<400> SEQUENCE: 6 tttttttactc atctgtgaag agaacctggg ggagtattgc ggaggaaggt                 50

<210> SEQ ID NO 7
<211> LENGTH: 30
<212> TYPE: DNA
<213> ORGANISM: Artificial Sequence
<220> FEATURE:
<223> OTHER INFORMATION: adenosine aptamer control

<400> SEQUENCE: 7 tttttttactc atctgtgaag agaacctggg                                       30

<210> SEQ ID NO 8
<211> LENGTH: 27
<212> TYPE: DNA
<213> ORGANISM: Artificial Sequence
<220> FEATURE:
<223> OTHER INFORMATION: biotin-modified DNA for IFN-gamma

<400> SEQUENCE: 8
aaaaaaaaaa aatcacagat gagtagt                                           27

<210> SEQ ID NO 9
<211> LENGTH: 25
<212> TYPE: DNA
<213> ORGANISM: Artificial Sequence
<220> FEATURE:
<223> OTHER INFORMATION: thiol-modified DNA for IFN-gamma

<400> SEQUENCE: 9
aaaaaaaaaa aaacaaccaa cccca                                             25

<210> SEQ ID NO 10
<211> LENGTH: 55
<212> TYPE: DNA
<213> ORGANISM: Artificial Sequence
<220> FEATURE:
<223> OTHER INFORMATION: IFN-gamma aptamer

<400> SEQUENCE: 10
tggggttggt tgtgttgggt gttgtgtaaa aaaaaaaaaa actactcatc tgtga            55

<210> SEQ ID NO 11
<211> LENGTH: 52
<212> TYPE: DNA
<213> ORGANISM: Artificial Sequence
<220> FEATURE:
<223> OTHER INFORMATION: UO22+-dependent DNAzyme

<400> SEQUENCE: 11
cacgtccatc tctgcagtcg ggtagttaaa ccgaccttca gacatagtga gt               52
```

<210> SEQ ID NO 12
<211> LENGTH: 51
<212> TYPE: DNA
<213> ORGANISM: Artificial Sequence
<220> FEATURE:
<223> OTHER INFORMATION: substrate of UO22+-dependent DNAzyme

<400> SEQUENCE: 12
actcatctgt gaactcacta traggaagag atggacgtga tctcgggaga c    51

<210> SEQ ID NO 13
<211> LENGTH: 30
<212> TYPE: DNA
<213> ORGANISM: Hepatitis B virus

<400> SEQUENCE: 13
actcatctgt gaatctcggg agacttttttt    30

<210> SEQ ID NO 14
<211> LENGTH: 30
<212> TYPE: DNA
<213> ORGANISM: Artificial Sequence
<220> FEATURE:
<223> OTHER INFORMATION: Hepatitis B target sequence with a G mismatch

<400> SEQUENCE: 14
actcatgtgt gaatctcggg agacttttttt    30

<210> SEQ ID NO 15
<211> LENGTH: 30
<212> TYPE: DNA
<213> ORGANISM: Artificial Sequence
<220> FEATURE:
<223> OTHER INFORMATION: hepatitis B target sequence with an A mismatch

<400> SEQUENCE: 15
actcatatgt gaatctcggg agacttttttt    30

<210> SEQ ID NO 16
<211> LENGTH: 30
<212> TYPE: DNA
<213> ORGANISM: Artificial Sequence
<220> FEATURE:
<223> OTHER INFORMATION: hepatitis B target sequence with a T mismatch

<400> SEQUENCE: 16
actcatttgt gaatctcggg agacttttttt    30

<210> SEQ ID NO 17
<211> LENGTH: 30
<212> TYPE: DNA
<213> ORGANISM: Artificial Sequence
<220> FEATURE:
<223> OTHER INFORMATION: hepatitis B target sequence with two mismatchs

<400> SEQUENCE: 17
actcaagtgt gaatctcggg agacttttttt    30

<210> SEQ ID NO 18
<211> LENGTH: 32
<212> TYPE: DNA
<213> ORGANISM: Artificial Sequence
<220> FEATURE:
<223> OTHER INFORMATION: thiol-modified DNA for HBV

```
<400> SEQUENCE: 18
tcctccccca actcctccca aaaaaaaaaa aa                                32

<210> SEQ ID NO 19
<211> LENGTH: 35
<212> TYPE: DNA
<213> ORGANISM: Hepatitis B virus

<400> SEQUENCE: 19
tgggaggagt gggggagga gattaggtta aaggt                              35

<210> SEQ ID NO 20
<211> LENGTH: 35
<212> TYPE: DNA
<213> ORGANISM: Artificial Sequence
<220> FEATURE:
<223> OTHER INFORMATION: HBV target sequence with an A mismatch

<400> SEQUENCE: 20
tgggaggagt gggggagga gattaggtaa aaggt                              35

<210> SEQ ID NO 21
<211> LENGTH: 35
<212> TYPE: DNA
<213> ORGANISM: Artificial Sequence
<220> FEATURE:
<223> OTHER INFORMATION: HBV target sequence with an G mismatch

<400> SEQUENCE: 21
tgggaggagt gggggagga gattaggtga aaggt                              35

<210> SEQ ID NO 22
<211> LENGTH: 35
<212> TYPE: DNA
<213> ORGANISM: Artificial Sequence
<220> FEATURE:
<223> OTHER INFORMATION: HBV target sequence with a C mismatch

<400> SEQUENCE: 22
tgggaggagt gggggagga gattaggtca aaggt                              35

<210> SEQ ID NO 23
<211> LENGTH: 18
<212> TYPE: DNA
<213> ORGANISM: Artificial Sequence
<220> FEATURE:
<223> OTHER INFORMATION: amine-modified DNA

<400> SEQUENCE: 23
agagaacctg ggttttt                                                 18

<210> SEQ ID NO 24
<211> LENGTH: 24
<212> TYPE: DNA
<213> ORGANISM: Artificial Sequence
<220> FEATURE:
<223> OTHER INFORMATION: thiol-modified DNA

<400> SEQUENCE: 24
aaaaaaaaaa aacccaggtt ctct                                         24
```

PERSONAL GLUCOSE METERS FOR DETECTION AND QUANTIFICATION OF A BROAD RANGE OF ANALYTES

CROSS REFERENCE TO RELATED APPLICATION

This is the U.S. National Stage of International Application No. PCT/US2011/038103, filed May 26, 2011, which was published in English under PCT Article 21(2), which in turn claims the benefit of U.S. Provisional Application No. 61/348,615 filed May 26, 2010, herein incorporated by reference in its entirety.

ACKNOWLEDGMENT OF GOVERNMENT SUPPORT

This invention was made with government support under DE-FG02-08ER64568 awarded by the US Department of Energy, under ES16865 awarded by the National Institutes of Health, and CTS-0120978 awarded by the National Science Foundation. The government has certain rights in the invention.

FIELD

This application relates to sensors, kits that include such sensors, and methods for making and using such sensors. The sensors permit detection of a broad array of target agents, such as nucleic acids (e.g., DNA and RNA), proteins, toxins, pathogens, cells, and metals, and can be used in combination with readily available personal glucose meters.

BACKGROUND

The development of sensors that are portable and inexpensive for quantification can realize the on-site and point-of-care applications of current sensing techniques in detecting substances of significant impact on human health and environment.[1-7] It can also further lead to household and personal sensors for analytes related to everyday life and health. One such successful example is glucose meter, which has been commercialized as a routine sensor for blood glucose over nearly 30 years and proven as a key element for monitoring diabetes mellitus or hypoglycemia.[8,9] The personal glucose meter (PGM) is well known for its advantages of wide availability to the public, portable pocket size, low cost, reliable quantitative results, and simple operation. Thus, it has found its widespread applications in personal healthcare and provided a large and growing market. PGM can be easily and cheaply obtained from commercial sources, and has already been integrated into mobile phones such as iPhone and LG models.

Despite of PGM's success, it is still a great challenge to develop sensor systems that can detect various analytes other than glucose but also exhibit advantages of glucose meter: wide availability, portability, low cost, and quantitative analysis. In recent years, sensors that can quantitatively detect various analytes with high selectivity and sensitivity have been developed using spectroscopy,[3-6] electrochemistry,[1,2] magnetic resonance,[7] and other analytical techniques. While some of these sensing techniques use simple instrumentation, most still need a laboratory-developed portable device, which is not widely and commercially available to the public. There are also colorimetric sensors developed for simple and on-site detection of various analytes by visible color change[10-13] thus no instrumentation is required. However, these sensors are qualitative or semi-quantitative, and thus cannot provide quantitative results.

SUMMARY

The present application discloses sensors, and methods of making such sensors, that can be used to detect a target agent. In one example, the sensor includes a solid support, such as a bead or membrane. A recognition molecule that permits detection of the target agent is bound or immobilized to the solid support. The recognition molecule specifically binds to the target agent in the presence of the target agent but not significantly to other agents. Examples of such recognition molecules include antibodies, nucleic acid molecules (such as DNA, RNA, functional nucleic acids including ribozymes/deoxyribozymes and aptamers), peptide nucleic acids, polymers, peptides and proteins, cells, and small organic molecules.

The sensor also can include an enzyme that can catalyze the conversion of a substance (such as sucrose, cellulose, trehalose, starch or maltose) into glucose. In one example, the enzyme is attached to the recognition molecule that permits detection of the target agent, for example as part of an enzyme analyte analogue conjugate that can bind to the recognition molecule, such that in the presence of the target agent the enzyme is released (e.g., the enzyme analyte analogue conjugate can be released due to competition with the target agent) from the solid support and can then catalyze the conversion of a substance (such as sucrose, cellulose, trehalose, starch or maltose) into glucose, which can be detected (for example using a personal glucose meter). In another example, the target agent is allowed to bind to the recognition molecule, and the enzyme analyte analogue conjugate binds to the target agent bound to the recognition molecule, thereby generating a "sandwich." Thus, in the presence of the target agent, the enzyme bound to the target agent can catalyze the conversion of a substance (such as sucrose, cellulose, trehalose, starch or maltose) into glucose, which can be detected (for example using a personal glucose meter, PGM).

In one example, the disclosed sensors are part of a lateral flow device. The lateral flow device can include a sample or wicking pad (which can be contacted with the sample), a conjugation pad comprising the sensor, a membrane that includes the substance that can be converted into glucose (such as sucrose), and an absorption pad (which draws the sample across the conjugation pad and membrane by capillary action and collects it and the resulting glucose produced). For example, the lateral flow device can be contacted with the sample and subsequently contacted with a glucose meter to detect the presence of a target agent in the sample, wherein the presence of the target in the sample is indicated by the detection of glucose.

The disclosure also provides kits that include the disclosed sensors and lateral flow devices. For example, such kits can further include one or more of a buffer, a chart for correlating detected glucose level and amount of target agent present, or the substance that the enzyme can convert into glucose (such as sucrose, trehalose, cellulose, maltose or starch).

Methods of detecting a target agent using the disclosed sensors are also provided. In one example the method includes contacting one or more sensors with a sample (such as a biological sample or an environmental sample) under conditions sufficient to allow the target agent in the sample to bind to the recognition molecule.

In some examples, such binding releases an enzyme (such as an enzyme analyte analogue conjugate) previously bound to the recognition molecule. The solid support is subsequently separated from the released enzyme. The released enzyme is contacted with the substance that the enzyme can convert into glucose, thereby generating glucose. The generated glucose is detected (for example using a PGM), wherein detection of glucose indicates the presence of the target agent in the sample, and an absence of detected glucose indicates the absence of the target agent in the sample. The method can also include quantifying the target agent, wherein a level of glucose detected indicates an amount (such as a relative or absolute amount) of target agent present.

In other examples, following binding of target agent to the recognition molecule, the enzyme is contacted with the target agent-recognition molecule-solid substrate complex under conditions to permit the enzyme (such as an enzyme analyte analogue conjugate) to bind to the target agent, thereby forming a "sandwich" type structure. The bound enzyme is then contacted with the substance (e.g., enzyme substrate) that the enzyme can convert into glucose, thereby generating glucose. The generated glucose is detected (for example using a PGM), wherein detection of glucose indicates the presence of the target agent in the sample, and an absence of detected glucose indicates the absence of the target agent in the sample. The method can also include quantifying the target agent, wherein a level of glucose detected indicates an amount (such as a relative or absolute amount) of target agent present.

In yet other examples, the method can include contacting a lateral flow device having a sensor with a sample under conditions sufficient to allow the target agent in the sample to flow through the lateral flow device and bind to the recognition molecule present on the lateral flow device. The recognition molecule can be conjugated to the enzyme that catalyzes the conversion of a substance into glucose. This results in the formation of a target agent-recognition molecule or a target agent-recognition molecule-enzyme complex, wherein formation of the complex results in the release of the enzyme that can convert the substance into glucose. The enzyme is allowed to interact with the substance that the enzyme can convert into glucose, thereby generating glucose. The resulting glucose is detected (for example quantified), wherein detection of glucose indicates the presence of the target agent in the sample, and an absence of detected glucose indicates the absence of the target agent in the sample.

Exemplary target agents that can be detected with the disclosed sensors and methods provided herein include a metal, nutritional metal ion (such as calcium, iron, cobalt, magnesium, manganese, molybdenum, zinc, cadmium, or copper), microbe, cytokine, hormone, cell (such as a tumor cell), DNA, RNA, spore (such as an anthrax spore), or toxin. For example, the target agent can be a heavy metal such as mercury (Hg), cadmium (Cd), arsenic (As), chromium (Cr), thallium (Tl), uranium (U), plutonium (Pu), or lead (Pb). In other examples, the target agent is a microbe, such as a virus, bacteria, fungi, or protozoa (such as a microbial antigen or nucleic acid molecule, such as DNA or RNA). In one example the target agent is a spore, such as a bacterial spore, fungal spore or plant spore. For example, *Bacillus* and *Clostridium* bacteria (such as *C. botulinum, C. perfringens, B. cereus*, and *B. anthracis*) produce spores that can be detected.

The foregoing and other objects and features of the disclosure will become more apparent from the following detailed description, which proceeds with reference to the accompanying figures.

BRIEF DESCRIPTION OF THE DRAWINGS

FIGS. 3A and 3B are schematic drawings showing exemplary mechanism of target agent (analyte) detection using a glucose meter based on the interaction between functional nucleic acid (FNA) A and FNA B and the target agent.

FIGS. 4A and 4B are schematic drawings showing exemplary mechanism of target agent (analyte) detection using a glucose meter based on the interaction between nucleic acid molecule A and nucleic acid molecule B and the target agent, wherein the target agent is a nucleic acid molecule.

FIGS. 8A and 8B are schematic drawings showing exemplary methods to conjugate DNA and invertase by (A) the heterobifuntional linker (sulfo-SMCC) and (B) the homobifunctional linker (PDITC).

FIG. 11 is a graph showing the role of aptamers on the performance of the sensors using glucose meter. For cocaine and adenosine sensors in the presence of 1 mM targets: (−): with underlined parts in the figure trunked; (+) with no truncation to the aptamers. Cocaine aptamer control shown in SEQ ID NO: 5; adenosine aptamer control shown in SEQ ID NO: 7.

SEQUENCE LISTING

Figure 1A:
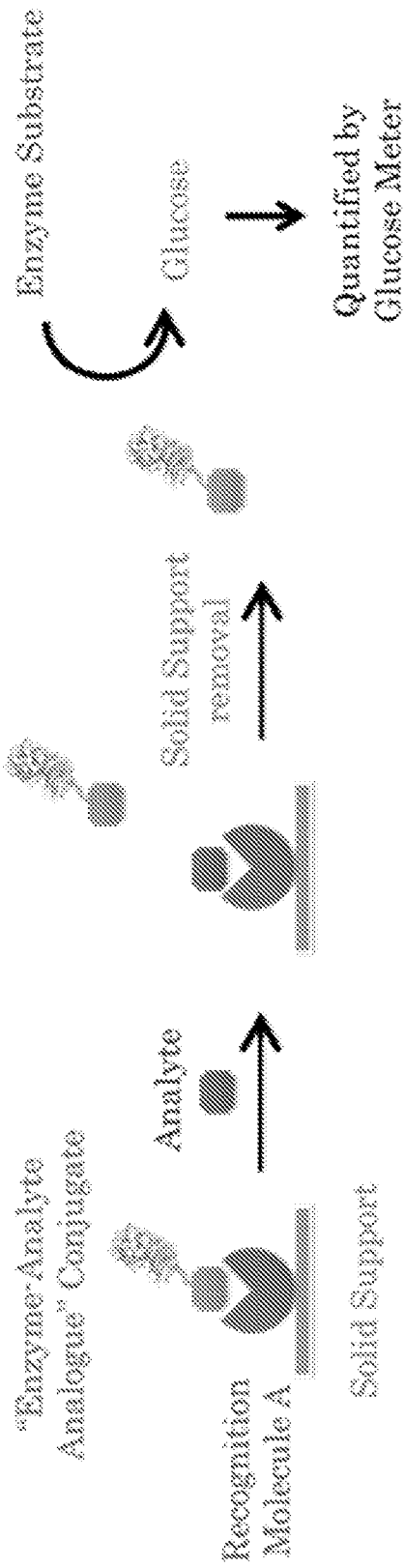
FIGS. 1A and 1B are schematic drawings showing exemplary mechanism of target agent (analyte) detection using a glucose meter based on the interaction between recognition molecule A and recognition molecule B and the target agent.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. All strands are shown 5' to 3' unless otherwise indicated.

SEQ ID NO: 1 is a biotin-modified DNA.
SEQ ID NO: 2 is a thiol-modified DNA.
SEQ ID NO: 3 is an amine-modified DNA.
SEQ ID NO: 4 is a cocaine aptamer.
SEQ ID NO: 5 is a cocaine aptamer control.
SEQ ID NO: 6 is an adenosine aptamer.
SEQ ID NO: 7 is an adenosine aptamer control.
SEQ ID NO: 8 is a biotin-modified DNA for IFN-γ.
SEQ ID NO: 9 is a thiol-modified DNA for IFN-γ.
SEQ ID NO: 10 is an IFN-γ aptamer.
SEQ ID NO: 11 is a $UO_2^{2+}$-dependent DNAzyme.
SEQ ID NO: 12 is a substrate of $UO_2^{2+}$-dependent DNAzyme.
SEQ ID NO: 13 is a hepatitis B virus (HBV) target sequence.
SEQ ID NO: 14 is a HBV target sequence with a G mismatch.
SEQ ID NO: 15 is a HBV target sequence with an A mismatch.
SEQ ID NO: 16 is a HBV target sequence with a T mismatch.
SEQ ID NO: 17 is a HBV target sequence with two mismatches.
SEQ ID NO: 18 is a thiol-modified DNA for HBV.
SEQ ID NO: 19 is a HBV target sequence.
SEQ ID NO: 20 is a HBV target sequence with an A mismatch.
SEQ ID NO: 21 is a HBV target sequence with a G mismatch.
SEQ ID NO: 22 is a HBV target sequence with a C mismatch.
SEQ ID NO: 23 is an amine-modified DNA.
SEQ ID NO: 24 is a thiol-modified DNA.

DETAILED DESCRIPTION

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2nd ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All publications, patent applications, patents, and other references mentioned herein are incorporated by reference in their entirety for all purposes. All sequences associated with the GenBank® Accession numbers mentioned herein are incorporated by reference in their entirety as were present on May 26, 2010, to the extent permissible by applicable rules and/or law.

In order to facilitate review of the various embodiments of the disclosure, the following explanations of specific terms are provided:

Antibody (Ab): A polypeptide that includes at least a light chain or heavy chain immunoglobulin variable region and specifically binds an epitope of an antigen (such as a target agent). Antibodies include monoclonal antibodies, polyclonal antibodies, or fragments of antibodies as well as others known in the art. In some examples, an antibody is specific for a target agent, such as a microbial antigen, spore, cell-surface receptor, or toxin, and thus can be used as a recognition molecule in the sensors provided herein.

Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies) and heteroconjugate antibodies (such as, bispecific antibodies). See also, Pierce Catalog and Handbook, 1994-1995 (Pierce Chemical Co., Rockford, Ill.); Kuby, *Immunology*, 3rd Ed., W.H. Freeman & Co., New York, 1997.

A "monoclonal antibody" is an antibody produced by a single clone of B lymphocytes or by a cell into which the light and heavy chain genes of a single antibody have been transfected. Monoclonal antibodies are produced by methods known to those of ordinary skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Antigen: A molecule that stimulates an immune response. Antigens are usually proteins or polysaccharides. An epitope is an antigenic determinant, that is, particular chemical groups or peptide sequences on a molecule that elicit a specific immune response. An antibody binds a particular antigenic epitope. The binding of an antibody to a particular antigen or epitope of an antigen can be used to determine if a particular antigen (such as a target antigen or antigen of interest) is present in a sample.

Binding: An association between two substances or molecules, such as the hybridization of one nucleic acid molecule to another (or itself), the association of an antibody with a peptide, the association of a protein with another protein or nucleic acid molecule, or the association between a hapten and an antibody. Binding can be detected by any procedure known to one skilled in the art, for example using the methods provided herein.

One molecule is said to "specifically bind" to another molecule when a particular agent (a "specific binding agent") can specifically react with a particular analyte, for example to specifically immunoreact with an antibody, or to specifically bind to a particular target agent. The binding is a non-random binding reaction, for example between an antibody molecule and an antigenic determinant or between one oligonucleotide (such as a functional nucleic acid) and a target agent (such as DNA or RNA). Binding specificity of an antibody is typically determined from the reference point of the ability of the antibody to differentially bind the specific antigen and an unrelated antigen, and therefore distinguish between two different antigens, particularly where the two antigens have unique epitopes. An antibody that specifically binds to a particular epitope is referred to as a "specific antibody". An oligonucleotide molecule binds or stably binds to a target nucleic acid molecule if a sufficient amount of the oligonucleotide molecule forms base pairs or is hybridized to its target nucleic acid molecule, to permit detection of that binding.

In particular examples, two compounds are said to specifically bind when the binding constant for complex formation between the components exceeds about $10^4$ L/mol, for example, exceeds about $10^6$ L/mol, exceeds about $10^8$ L/mol, or exceeds about $10^{10}$ L/mol. The binding constant for two components can be determined using methods that are well known in the art.

Detect: To determine if a particular agent is present or absent, and in some example further includes quantification of the agent if detected.

Glucose Meter: Refers to any medical device for determining the approximate concentration of glucose in the blood. Glucose meters include any commercially available glucose meter, such as a personal glucose meter (PGM). Such meters typically display the level of glucose in mg/dl or mmol/l. The disclosure is not limited to a particular brand of glucose meter, though examples include ACCU-CHEK® glucose meter, ONETOUCH® glucose meter, PRODIGY® glucose meter, ADVOCATE® glucose meter, AGAMATRIX® glucose meter, ASCENSIA® glucose meter, BIONIME® glucose meter, CLEVERCHEK®, EASYGLUCO®, FREESTYLE® glucose meter, MAXIMA® glucose meter, MEDISENSE® glucose meter, PRESTIGE® glucose meter, TRUEBALANCE® glucose meter, TRUETEST® glucose meter.

Immobilized: Bound to a surface, such as a solid support. In one embodiment, the solid surface is in the form of a bead. The surface can include immobilized recognition molecules that can specifically bind to a target agent. In some examples, an enzyme that can catalyze the conversion of a substance into glucose is bound (directly or indirectly) to the recognition molecule that permits detection of a target agent. In one example, the enzyme that can catalyze the conversion of a substance into glucose is liberated from the solid support (or is released thus allowing it to move to another part of the solid support, such as from one part of a lateral flow device to another) once the target agent binds to the molecule immobilized to the solid support. Methods of immobilizing agents to solid supports are known in the art. For example, methods of immobilizing peptides on a solid surface can be found in WO 94/29436, and U.S. Pat. No. 5,858,358. In some examples, agents are immobilized to a support by simply applying the agent in solution to the support, and allowing the solution to dry, thereby immobilizing the agent to the support.

Invertase: (EC 3.2.1.26) An enzyme that catalyzes the hydrolysis of sucrose into fructose and glucose. Also known as beta-fructofuranosidase. Nucleic acid and protein sequences for invertase are publicly available. For example, GENBANK® Accession Nos.: D10265; AY378100 REGION: 43839.44963; Z46921 REGION: 37385.38983 and AB534221 disclose exemplary invertase nucleic acid sequences, and GENBANK® Accession Nos.: BAA01107.1; AAR07688.1; BAA25684.1; CAA87030.1 and BAJ07824.1 disclose exemplary invertase protein sequences, all of which are incorporated by reference as provided by GENBANK® on May 26, 2010. In certain examples, invertase has at least 80% sequence identity, for example at least 85%, 90%, 95%, or 98% sequence identity to a publicly available invertase sequence, and is an invertase which can catalyze the hydrolysis of sucrose into fructose and glucose.

Lateral flow device: An analytical device in the form of a test strip used in lateral flow chromatography, in which a sample fluid, such as one suspected of containing a target agent, flows (for example by capillary action) through the strip (which is frequently made of bibulous materials such as paper, nitrocellulose, and cellulose). The test sample and any suspended analyte (including target agents) can flow along the strip to a detection zone in which the target agent (if present) interacts with a recognition molecule of the sensors provided herein to indicate a presence, absence and/or quantity of the target agent.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,368,876; 7,799,554; EP 0810436; and WO 92/12428; WO 94/01775; WO 95/16207; and WO 97/06439, each of which is incorporated by reference.

Lateral flow devices can in one example be a one-step lateral flow assay in which a sample fluid is placed in a sample or wicking area on a bibulous strip (though, non bibulous materials can be used, and rendered bibulous by applying a surfactant to the material), and allowed to migrate along the strip until the sample comes into contact with a recognition molecule that interacts with a target agent in the liquid. After the target agent binds to the recognition molecule, the enzyme that can convert a substance into glucose is released (for example from the recognition molecule), and allowed to interact with the substance, thereby generating glucose indicating that the interaction has occurred, and that the target agent is present in the sample. The resulting glucose can be detected with a PGM In some examples, multiple discrete binding partners can be placed on the strip (for example in parallel lines or as other separate portions of the device) to detect multiple target agents in the liquid. The test strips can also incorporate control indicators, which provide a signal that the test has adequately been performed, even if a positive signal indicating the presence (or absence) of an analyte is not achieved.

A lateral flow device can include a sample application area or wicking pad, which is where the fluid or liquid sample is introduced. In one example, the sample may be introduced to the sample application area by external application, as with a dropper or other applicator. In another example, the sample application area may be directly immersed in the sample, such as when a test strip is dipped into a container holding a sample. In yet another example, the sample may be poured or expressed onto the sample application area.

A lateral flow device can include a conjugation pad, the region of a lateral flow device where the recognition molecule (such as a recognition molecule-enzyme that can convert a substance to glucose) is immobilized. A lateral flow device may have more than one conjugation area, for example, a "primary conjugation area," a "secondary conjugation area," and so on. Often a different capture reagent will be immobilized in the primary, secondary, or other conjugation areas. Multiple conjugation areas may have any orientation with respect to each other on the lateral flow substrate; for example, a primary conjugation area may be distal or proximal to a secondary (or other) conjugation area and vice versa. Alternatively, a primary conjugation area and a conjugation (or other) capture area may be oriented perpendicularly to each other such that the two (or more) conjugation areas form a cross or a plus sign or other symbol. For example, Apilux et al. (*Anal. Chem.* 82:1727-32, 2010), Dungchai et al. (*Anal. Chem.* 81:5821-6, 2009), and Dungchai et al. (*Analytica Chemica Acta* 674:227-33, 2010), provide exemplary lateral flow devices with a central sample area and one or more conjugation areas distal to the sample area, which provide independent test zones where independent reactions can occur (e.g., each test zone has a different recognition molecule, and can further include as a membrane that includes the substance that can be converted into glucose and an absorption pad that receives the generated glucose, wherein each absorption pad can be independently read by a PGM), for example that form a "Y", cloverleaf, or spoke-wheel pattern.

A lateral flow device can include a membrane that includes the substance that can be converted into glucose (such as sucrose), and an absorption pad that draws the sample across the conjugation pad and membrane by capillary action and collects it.

Sensor: A device that is used to detect the presence of a target, such as a target analyte/agent. The disclosed sensors include a recognition molecule that is specific for the target agent, attached to a solid support, and an enzyme that can catalyze the conversion of a substance into glucose (for example in the presence of the target agent). The enzyme can be attached directly or indirectly to the recognition molecule.

Target Agent: Any substance whose detection is desired, including, but not limited to, a chemical compound, metal, pathogen, toxin, nucleic acid (such as DNA or RNA), or protein (such as a cytokine, hormone or antigen), as well as particular cells (such as a cancer cell or bacterial cell), viruses, or spores.

Sensors for Detecting Target Agents

Provided herein are sensors that can be used to detect an analyte of interest (referred to herein as a target agent). Such sensors can be engineered using the methods provided herein to detect a broad range of targets, significantly facilitating rational design and increasing the efficiency of sensor development. By combining molecules that can specifically bind to a target agent (referred to herein as recognition molecules), enzymes that can convert a substance (such as an enzyme substrate) into glucose, and commercially available personal glucose meters (PGM), a general platform for the design of portable, low-cost and quantitative sensors specific to a broad range of analytes is provided. In one example, the approach is based on the target agent-induced release of the enzyme from a solid support, or the use of an enzyme-recognition molecule complex that can also bind to the target agent, wherein the enzyme can efficiently convert a PGM-inert substance (such as sucrose) into PGM-detectable glucose.

Using this general methodology, sensitive and selective particular examples of sensors for the quantification of cocaine, adenosine, interferon-γ (IFN-γ), and $UO_2^{2+}$ are reported herein that require only a commercially available PGM to do the detections. Cocaine is an addictive drug whose detection is important for the regulation of the drug abuse;[32,43] adenosine is an important metabolite and involved in many biological processes;[46] IFN-γ is a cytokine related to human immune system,[47] and IFN-γ release assay is currently used for the diagnosis of tuberculosis,[48] which is an infectious disease estimated to be latent in one-third of the world's population and 10% of the latently infected may become active during lifetime; $UO_2^{2+}$ is a radioactive heavy metal ion that is hazardous to both human and environment.[49] Using this platform, many other sensors for various analytes using a PGM can be achieved through the general approach described herein.

Disclosed herein are sensors that permit detection of a target agent. In one example, such sensors include a solid support to which is attached a recognition molecule that permits detection of a target agent. For example, the recognition molecule can bind to the target agent with high specificity in the presence of the target agent but not significantly to other agents. The sensors in some examples also include an enzyme that can catalyze the conversion of a substance (enzyme substrate) into glucose (or any other product that can be detected by any glucose meter). For example, the enzyme can be invertase, sucrase or sucrase-isomaltase which can convert sucrose into glucose, maltase which can convert maltose into glucose, trehalase which can convert trehalose into glucose, lactase which can convert lactose into glucose, amylase or glucoamylase which can convert starch into glucose, or a cellulase that can convert cellulose into glucose. The enzyme can also be an alpha- or beta-glucosidase or debranching enzyme from any source. In one example, the enzyme is attached to the recognition molecule that permits detection of a target agent, such that in the presence of the target agent the enzyme is released from the solid support and can convert the substance into glucose, which can be detected and in some examples quantified. In another example, the enzyme is not initially part of the sensor, but instead after the target agent binds to the recognition molecule, a second recognition molecule (which may be the same or a different recognition molecule attached to the solid support) which has conjugated thereto the enzyme, binds to the target agent bound to the first recognition molecule bound to the solid support, thus creating a type of "sandwich." The bound enzyme can then convert the substance into glucose, which can be detected and in some examples quantified.

One skilled in the art will recognize that any approach using other techniques to transform one target agent's concentration information into another's, which is subsequently detected using the methods in this application, can be used. For example, if target agent A can quantitatively produce substance B by a certain technique, one can simply use the methods in this application to detect substance B, and then convert the concentration of substance B into that of target agent A in the sample.

Figure 1B:
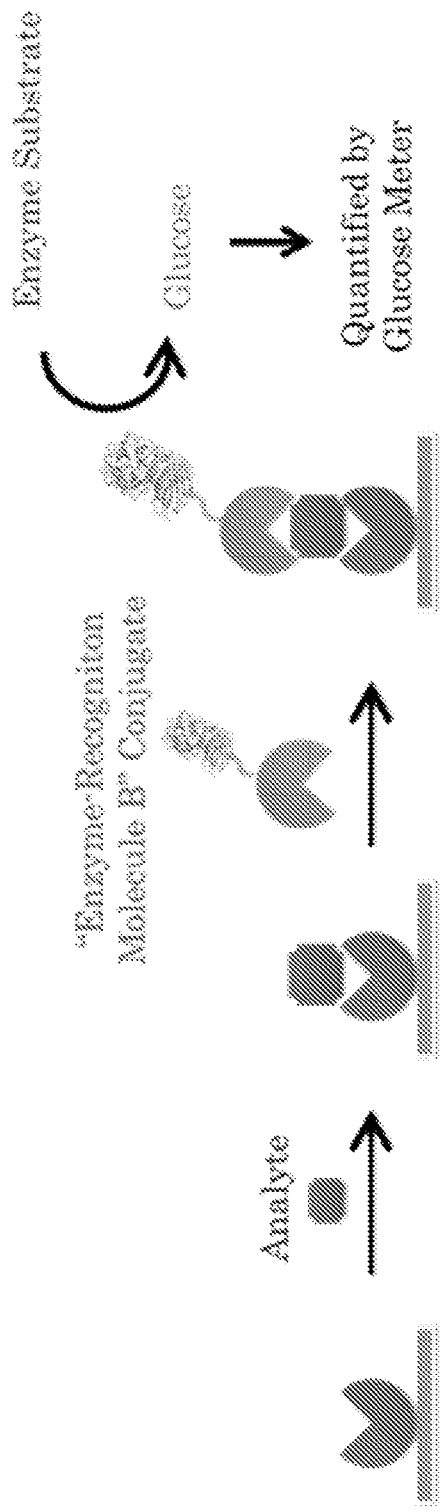

FIGS. 1A-B provide an overview of the sensors and the methods of their use. In FIGS. 1A and 1B, the recognition molecule A and recognition molecule B (referred to herein as the recognition molecule that can bind to the target agent with high specificity) can be the same or different molecules, wherein both can bind to the analyte (referred to herein as the target agent). The enzyme that can catalyze the conversion of a substance (enzyme substrate) into glucose is conjugated with an analyte analogue (that is, an analogue of the target agent; FIG. 1A) or recognition molecule B (FIG. 1B) using a conjugation method to form enzyme-analyte analogue conjugate (FIG. 1A) or enzyme-recognition molecule B conjugate (FIG. 1B), respectively. The enzyme substrate can be catalytically converted into glucose by enzyme, and the glucose produced can be quantified by a glucose meter. The test agent (analyte) can be any substance that can be recognized by recognition molecule A and Recognition molecule B.

The analyte analogue can be any substance that can bind to recognition molecule A, and completes with the binding between the target agent and recognition molecule A. Examples of analyte analogue include but are not limited to: antibodies and antigens; aptamers and corresponding targets; ribozymes and corresponding cofactors or targets; DNAzymes or catalytic DNAs or DNA enzymes and corresponding cofactors or targets; and nucleic acids or other analogues, such as peptide nucleic acids, locked nucleic acids, and any chemically modified analogues. The enzyme-analyte analogue conjugate and the enzyme-recognition molecule B conjugate are prepared by conjugating the enzyme with the analyte analogue or recognition molecule B, respectively, using routine conjugation methods.

FIG. 1A shows an exemplary release-based assay. Initially, enzyme-analyte analogue conjugate binds to the solid support through the interaction between enzyme-analyte analogue conjugate and recognition molecule A. When samples containing the test agent are applied to the solid support, the enzyme-analyte analogue conjugate will be released as a result of the competition between enzyme-analyte analogue conjugate and test agent in binding with recognition molecule A. The concentration of enzyme-analyte analogue conjugate released can be proportional to the test agent concentration in the sample. After removal of the solid support, enzyme-analyte analogue conjugate remaining in the solution can catalyze the conversion of the enzyme substrate into glucose, which is detected by a glucose meter, and the readout is proportional to the analyte concentration.

FIG. 1B shows an exemplary binding-base assay. Initially, recognition molecule A is immobilized to the solid support. When a sample containing or suspected of containing the test agent (analyte) is applied to solid support, the analyte binds to recognition molecule A. Subsequently, enzyme-recognition molecule B conjugate is added and will bind to the analyte on recognition molecule A, forming a sandwich structure. The amount of enzyme-recognition molecule B conjugate bound can be proportional to the concentration of analyte in the sample. After applying enzyme substrate (e.g., sucrose) to solid support, the bound enzyme-recognition molecule B conjugate can convert enzyme substrate into glucose, which is detected by a glucose meter, and the readout is proportional to the analyte concentration. So in this example, the enzyme is not bound to recognition molecule A, nor is released and separated from the solid support. The enzyme is actually bound to the target agent, and the target agent can bind both recognition molecules A and B together. In this way, in the presence of more the target agent, more enzyme will be bound to the solid support, and the solid support can convert more sucrose into glucose, giving a larger readout in glucose meter.

Figure 2A:
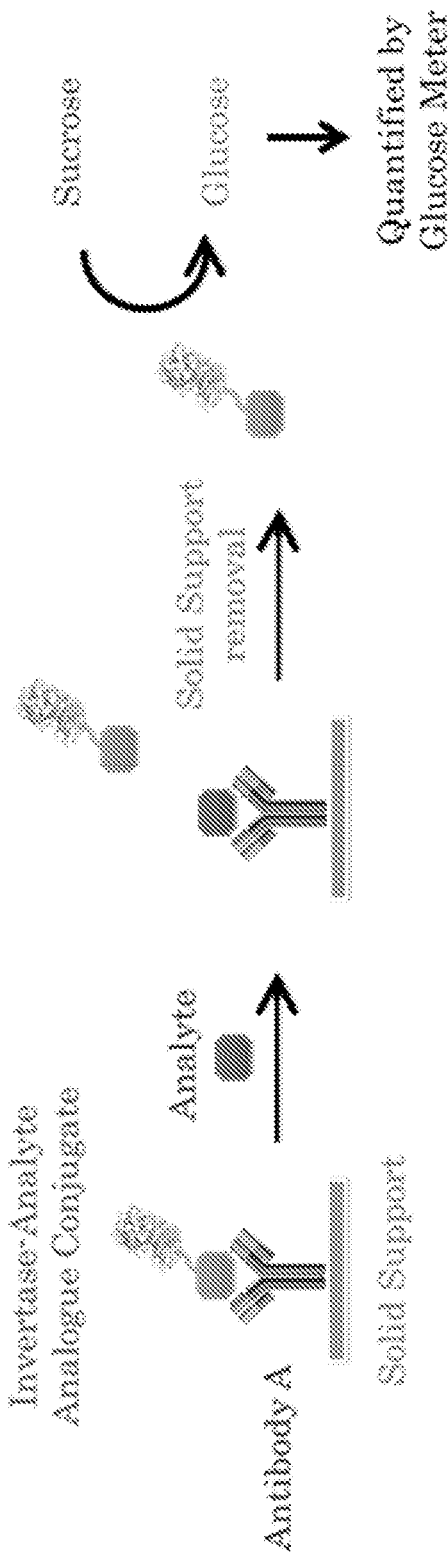
FIGS. 2A and 2B are schematic drawings showing exemplary mechanism of target agent (analyte) detection using a glucose meter based on the interaction between antibody A and antibody B and the target agent.
Figure 2B:
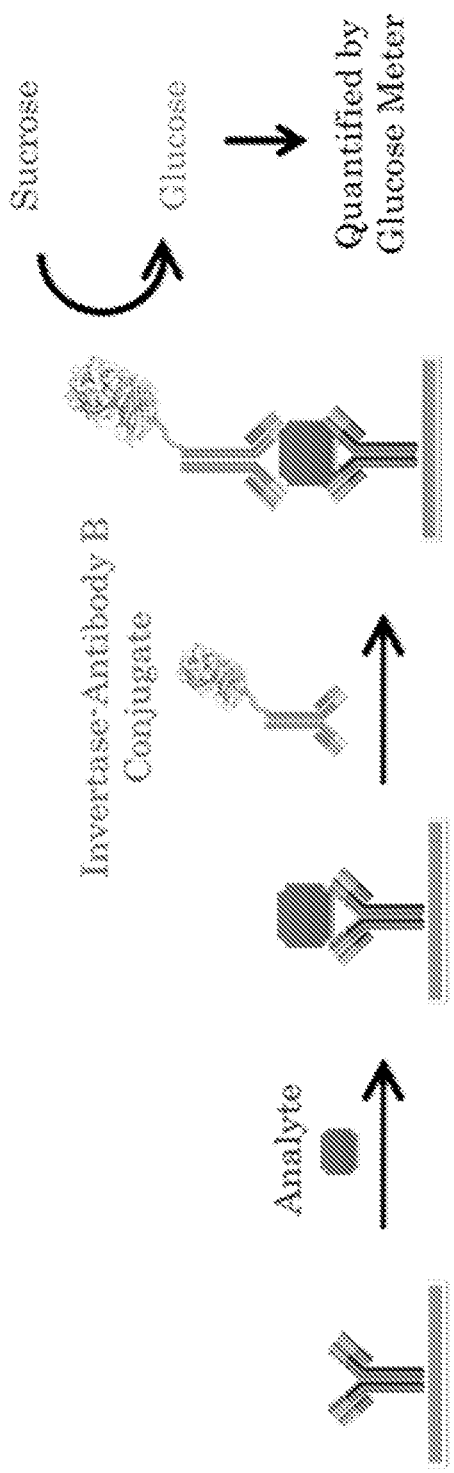

As shown in FIGS. 2A and 2B, the recognition molecules in FIGS. 1A and 1B can be antibodies (e.g., antibody A and antibody B). By either method shown in FIG. 2A or 2B, any target agent that has antibodies can be quantified by a glucose meter. As shown in FIGS. 2A and 2B, antibody A and antibody B both can bind the analyte (target agent); they can be the same antibody or different antibodies that are specific for the same analyte.

FIG. 2A shows the release-based approach. Antibody A is immobilized on the solid support using routine conjugation methods. The enzyme-analogue conjugate (e.g., invertase-antibody conjugate) is added and will bind to antibody A. The enzyme-analogue conjugate can be prepared using routine methods. A sample containing analyte (e.g., suspected of containing the target agent) is contacted with the solid support under conditions that permit the target agent to specifically bind to antibody A, thereby displacing the enzyme-analogue conjugate due to competition. The amount of enzyme-analogue conjugate released can be proportional to the concentration of target agent in the sample. After removal of the solid support, the enzyme-antibody conjugate can convert the enzyme substrate (e.g., sucrose) into glucose, which is detected by a glucose meter, and the readout is proportional to the target agent concentration in the sample tested.

FIG. 2B shows the binding-based approach. Antibody A is immobilized on the solid support using routine methods. A sample containing analyte (e.g., suspected of containing the target agent) is contacted with the solid support under conditions that permit the target agent to specifically bind to antibody. Enzyme-antibody B conjugate (e.g., invertase-antibody B conjugate) is added and will bind to the analyte (target agent) bound to antibody A, forming a sandwich structure. The enzyme-antibody B conjugate can be prepared using routine methods. The amount of enzyme-antibody B conjugate bound can be proportional to the concentration of target agent in the sample. After applying an enzyme substrate (e.g., sucrose) solution to the solid support, the bound enzyme-antibody B conjugate can convert the enzyme substrate (e.g., sucrose) into glucose, which is detected by a glucose meter, and the readout is proportional to the target agent concentration in the sample tested.

As shown in FIGS. 3A and 3B, the recognition molecules in FIGS. 1A and 1B can be functional nucleic acids, such as an aptamer, DNAzyme, or aptazyme (e.g., functional nucleic acid (FNA) A and B). As shown in FIGS. 3A and 3B, FNA A and FNA B both can bind the analyte (target agent); they can be the same FNA or different FNAs that are specific for the same analyte.

FIG. 3A shows the release-based approach. FNA A is immobilized on the solid support using routine immobilization methods. The enzyme-analogue conjugate (e.g., invertase-analyte analogue conjugate) is added and will bind to FNA A. The enzyme-analogue conjugate can be prepared using routine methods. A sample containing analyte (e.g., suspected of containing the target agent) is contacted with the solid support under conditions that permit the target agent to specifically bind to FNA A, thereby displacing the enzyme-analogue conjugate due to competition. The amount of enzyme-analogue conjugate released can be proportional to the concentration of target agent in the sample. After removal of the solid support, the enzyme-antibody conjugate can convert the enzyme substrate (e.g., sucrose) into glucose, which is detected by a glucose meter, and the readout is proportional to the target agent concentration in the sample tested.

FIG. 3B shows the binding-based approach. FNA A is immobilized on the solid support using routine methods. A sample containing analyte (e.g., suspected of containing the target agent) is contacted with the solid support under conditions that permit the target agent to specifically bind to FNA A. Enzyme-FNA B conjugate (e.g., invertase-FNA B conjugate) is added and will bind to the analyte (target agent) bound to FNA A, forming a sandwich structure. The enzyme-FNA B conjugate can be prepared using routine methods. The amount of enzyme-FNA B conjugate bound can be proportional to the concentration of target agent in the sample. After applying an enzyme substrate (e.g., sucrose) solution to the solid support, the bound enzyme-FNA B conjugate can convert the enzyme substrate (e.g., sucrose) into glucose, which is detected by a glucose meter, and the readout is proportional to the target agent concentration in the sample tested.

Because the target analyte can be any species that can be recognized by the recognition molecules A and B shown in FIGS. 1A and 1B, the disclosure is not limited to the use of a particular recognition component. For example, in addition to antibodies (FIGS. 2A and 2B), and functional nucleic acids (FIGS. 3A and 3B), they may include peptides, proteins, polymers and even small molecules that recognize targets analytes. For example, as shown in FIGS. 4A and 4B, nucleic acids can be detected by hybridization between nucleic acids. In this example, the target agent is a nucleic acid, and recognition molecule A and recognition molecule B of FIGS. 1A and 1B are replaced by nucleic acids that can hybridize with the analyte. One will also recognize that a combined approach can also be used, such as replacing recognition molecule A and recognition molecule B (FIGS. 1A and 1B) with an antibody and a functional nucleic acid, respectively (or vice versa).

As shown in FIGS. 4A and 4B, the recognition molecules in FIGS. 1A and 1B can be nucleic acids (e.g., DNA), and the analyte (target agent) can also be a nucleic acid. As shown in FIGS. 4A and 4B, nucleic acid A and nucleic acid B both can bind the analyte (target agent); they can be the same nucleic acid or different nucleic acid that are specific for the same nucleic acid target agent.

FIG. 4A shows the release-based approach. DNA A is immobilized on the solid support using routine immobilization methods. The enzyme-analogue conjugate (e.g., invertase-analyte analogue conjugate) is added and will bind to DNA A. The enzyme-analogue conjugate can be prepared using routine methods. A sample containing analyte (e.g., suspected of containing the target agent) is contacted with the solid support under conditions that permit the target agent to specifically bind to DNA A, thereby displacing the enzyme-analogue conjugate due to competition. The amount of enzyme-analogue conjugate released can be proportional to the concentration of target agent in the sample. After removal of the solid support, the enzyme-antibody conjugate can convert the enzyme substrate (e.g., sucrose) into glucose, which is detected by a glucose meter, and the readout is proportional to the target agent concentration in the sample tested.

FIG. 4B shows the binding-based approach. DNA A is immobilized on the solid support using routine methods. A sample containing analyte (e.g., suspected of containing the target agent) is contacted with the solid support under conditions that permit the target agent to specifically bind to DNA A. Enzyme-DNA B conjugate (e.g., invertase-DNA B conjugate) is added and will bind to the analyte (target agent) bound to DNA A, forming a sandwich structure. The enzyme-DNA B conjugate can be prepared using routine methods. The amount of enzyme-DNA B conjugate bound can be proportional to the concentration of target agent in the sample. After applying an enzyme substrate (e.g., sucrose) solution to the solid support, the bound enzyme-DNA B conjugate can convert the enzyme substrate (e.g., sucrose) into glucose, which is detected by a glucose meter, and the readout is proportional to the target agent concentration in the sample tested.

FIG. 5 shows a specific example of the disclosed sensors. The sensor design is based on both analyte-induced release of DNA from functional DNA duplex immobilized on magnetic beads as signal initiator and DNA-invertase conjugate as signal amplifier. Upon the binding of a specific target to the DNA, the single strand DNA (ssDNA) that is partially complementary to the aptamer or the substrate of the DNAzyme is released because of the structure-switching of the aptamer or the catalytic reaction by the DNAzyme. Since the ssDNA is covalently conjugated with invertase, the invertase is then released with the ssDNA. The released invertase can subsequently catalyze the hydrolysis of sucrose into fructose and glucose, which is further detected by a PGM and can be used to quantify the concentration of the analyte in the sample.

Solid Supports

The solid support which forms the foundation of the sensor can be formed from known materials, such as any water immiscible material. In some examples, suitable characteristics of the material that can be used to form the solid support surface include: being amenable to surface activation such that upon activation, the surface of the support is capable of covalently attaching a recognition molecule that can bind to the target agent with high specificity, such as an oligonucleotide or a protein; being chemically inert such that at the areas on the support not occupied by the molecule can bind to the target agent with high specificity are not amenable to non-specific binding, or when non-specific binding occurs, such materials can be readily removed from the surface without removing the molecule can bind to the target agent with high specificity.

A solid phase can be chosen for its intrinsic ability to attract and immobilize an agent, such as recognition molecule that can bind to the target agent with high specificity. Alternatively, the solid phase can possess a factor that has the ability to attract and immobilize an agent, such as a recognition molecule. The factor can include a charged substance that is oppositely charged with respect to, for example, the recognition molecule itself or to a charged substance conjugated to the recognition molecule. In another embodiment, a specific binding member may be immobilized upon the solid phase to immobilize its binding partner (e.g., a recognition molecule). In this example, therefore, the specific binding member enables the indirect binding of the recognition molecule to a solid phase material.

The surface of a solid support may be activated by chemical processes that cause covalent linkage of an agent (e.g., a recognition molecule specific for the target agent) to the support. However, any other suitable method may be used for immobilizing an agent (e.g., a recognition molecule) to a solid support including, without limitation, ionic interactions, hydrophobic interactions, covalent interactions and the like. The particular forces that result in immobilization of a recognition molecule on a solid phase are not important for the methods and devices described herein.

In one example the solid support is a particle, such as a bead. Such particles can be composed of metal (e.g., gold, silver, platinum), metal compound particles (e.g., zinc oxide, zinc sulfide, copper sulfide, cadmium sulfide), non-metal compound (e.g., silica or a polymer), as well as magnetic particles (e.g., iron oxide, manganese oxide). In some examples the bead is a latex or glass bead. The size of the bead is not critical; exemplary sizes include 5 nm to 5000 nm in diameter. In one example such particles are about 1 µm in diameter.

In another example, the solid support is a bulk material, such as a paper, membrane, porous material, water immiscible gel, water immiscible ionic liquid, water immiscible polymer (such as an organic polymer), and the like. For example, the solid support can comprises a membrane, such as a semi-porous membrane that allows some materials to pass while others are trapped. In one example the membrane comprises nitrocellulose. In a specific example the solid support is part of a lateral flow device that includes a region containing the sensors disclosed herein.

In some embodiments, porous solid supports, such as nitrocellulose, are in the form of sheets or strips, such as those found in a lateral flow device. The thickness of such sheets or strips may vary within wide limits, for example, at least 0.01 mm, at least 0.1 mm, or at least 1 mm, for example from about 0.01 to 5 mm, about 0.01 to 2 mm, about 0.01 to 1 mm, about 0.01 to 0.5 mm, about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

In one example, the solid support is composed of an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof).

In yet other examples, the solid support is a material containing, such as a coating containing, any one or more of or a mixture of the ingredients provided herein.

A wide variety of solid supports can be employed in accordance with the present disclosure. Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

The solid support can be any format to which the molecule specific for the test agent can be affixed, such as microtiter plates, ELISA plates, test tubes, inorganic sheets, dipsticks, lateral flow devices, and the like. One example includes a linear array of molecules specific for the target agent, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range.

In one example the format is a bead, such as a silica bead. In another example the format is a nitrocellulose membrane. In another example the format is filter paper. In yet another example the format is a glass slide. In one example, the solid support is a polypropylene thread. One or more polypropylene threads can be affixed to a plastic dipstick-type device; polypropylene membranes can be affixed to glass slides.

In one example the solid support is a microtiter plate. For example sensors can be affixed to the wells of a microtiter plate (for example wherein some wells can contain a sensor to detect target X, while other wells can contain a sensor to detect target Y; or several wells might include the same sensor, wherein multiple samples can be analyzed simultaneously). The test sample potentially containing an analyte of interest can be placed in the wells of a microtiter plate containing a sensor disclosed herein, and the presence of the target detected using the methods provided herein in. One advantage of the microtiter plate format is that multiple samples can be tested simultaneously (together with controls) each in one or more different wells of the same plate; thus, permitting high-throughput analysis of numerous samples.

Figure 24:
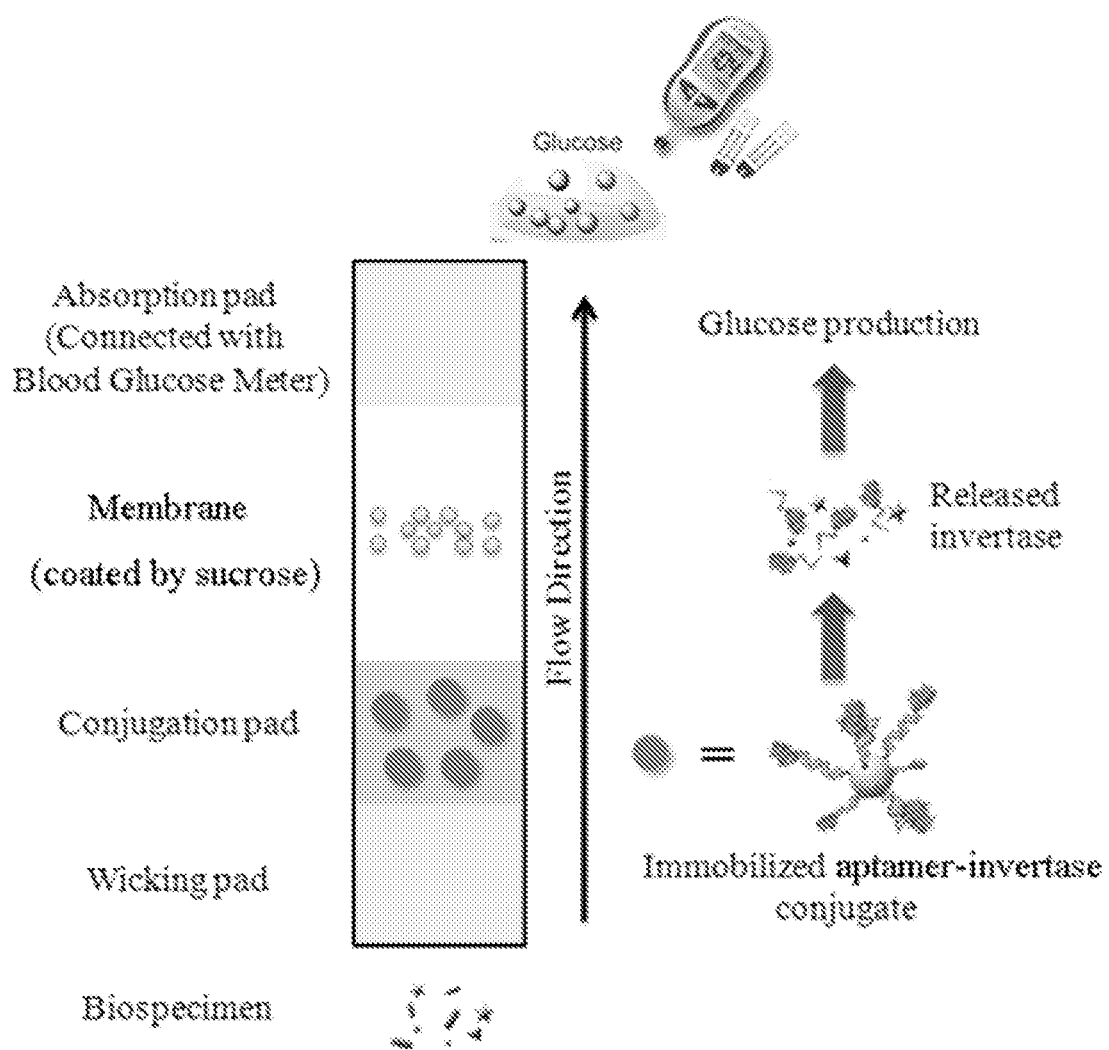
FIG. 24 is a schematic drawing show a lateral flow device modified with aptamer-invertase conjugate for the detection of a target agent in a sample.

In some examples, the disclosed sensor is attached to more than one solid support. For example, as illustrated in FIG. 24 for example, a sensor containing a recognition molecule-enzyme complex can be attached to a bead, which can then be attached to a conjugation pad of a lateral flow device.

Each of the supports and devices discussed herein (e.g., ELISA, lateral flow device) can be, in some embodiments, formatted to detect multiple analytes by the addition of recognition molecules specific for the other analytes of interest. For example, certain wells of a microtiter plate can include recognition molecules specific for the other analytes of interest. Some lateral flow device embodiments can include secondary, tertiary or more capture areas containing recognition molecules specific for the other analytes of interest.

Lateral Flow Devices

In one example, the solid support is a lateral flow device, which can be used to determine the presence and/or amount of one or more target agents in a fluid sample. A lateral flow device is an analytical device having a test strip, through which flows a test sample fluid that is suspected of (or known to) containing a target agent. Lateral flow devices are useful to simplify and automate user sample interface and processing. One example of a lateral flow device is a pregnancy strip. Based on the principles of a pregnancy strip, lateral flow devices that incorporate the disclosed sensors can be developed. In some examples, by using such as lateral flow devices, samples can be directly contacted with or applied to the lateral flow device, and no further liquid transfer or mixing is required. Such devices can be used to detect target agents, for example qualitatively or quantitatively.

Lateral flow devices are commonly known in the art, and have a wide variety of physical formats. Any physical format that supports and/or houses the basic components of a lateral flow device in the proper function relationship is contemplated by this disclosure. In one example, the lateral flow devices disclosed in U.S. Pat. No. 7,799,554, Liu et al. (*Angew. Chem. Int. Ed.* 45:7955-59, 2006), Apilux et al. (*Anal. Chem.* 82:1727-32, 2010), Dungchai et al. (*Anal. Chem.* 81:5821-6, 2009), or Dungchai et al. (*Analytica Chemica Acta* 674:227-33, 2010) (all herein incorporated by reference) are used, such as one made using the Millipore Hi-Flow Plus Assembly Kit. There are a number of commercially available lateral flow type tests and patents disclosing methods for the detection of large analytes (MW greater than 1,000 Daltons) (see for example U.S. Pat. Nos. 5,229,073; 5,591,645; 4,168,146; 4,366,241; 4,855,240; 4,861,711; and 5,120,643; European Patent No. 0296724; WO 97/06439; and WO 98/36278). There are also lateral flow type tests for the detection of small-analytes (MW 100-1,000 Daltons) (see for example U.S. Pat. Nos. 4,703,017; 5,451,504; 5,451,507; 5,798,273; and 6,001,658).

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810; both of which are incorporated herein by reference.

Devices described herein generally include a strip of absorbent material (such as a microporous membrane), which can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific recognition molecule(s) and/or other reagents (such as an enzyme substrate that can be converted to glucose by an enzyme, such as sucrose) required for the detection and/or quantification of the particular analyte being tested for. Thus these zones can be viewed as functional sectors or functional regions within the test device.

These devices typically include a sample application area and one or more separate target agent capture areas (conjugation pad) in which an immobilized sensor disclosed herein is provided which sensor includes a recognition molecule having a specific binding affinity for a target agent. For example, a lateral flow device containing at least two separate target agent capture areas (such as 2, 3, 4, 5, 6, 7, 8, 9, 10, 11, 12, 13, 14, 15 or more) can be used to detect a plurality of different target agents in a single sample. Any liquid (such as a fluid biological sample) applied in the sample application area flows along a path of flow from the sample application area to the capture area. Upon binding of the target agent to the recognition molecule, the enzyme that can catalyze the conversion of a substance to glucose is released (for examples of such enzymes and substances see Table 2). The enzyme flows to a downstream membrane containing the appropriate substance. The substance (such as sucrose) is converted to glucose which flows to a downstream absorbent pad, which can act as a liquid reservoir. The resulting glucose on the lateral flow strip can be detected with a PGM, for example by insertion of the device into a PGM.

In one example where a lateral flow device can detect multiple targets, the device includes a single wicking pad or sample application area, and multiple conjugation pads, membranes and absorption pads (such that each conjugation pad is associated with a particular membrane and absorption pad). For example, each conjugation pad can include a different recognition molecule specific for a particular target agent. Thus, the glucose produced as a result of the target agent and present on each absorption pad can be used to detect the presence of a particular target agent.

To make PGMs capable of detecting a broad range of non-glucose targets in many different samples, a lateral flow device can be generated that includes a recognition molecule, which can be conjugated to an enzyme (such as invertase) that can catalyze the conversion of a substance (such as sucrose) into glucose. In one example, the recognition molecule is a nucleic acid aptamer (such as a DNA aptamer) with high specificity for the target. In another example, the recognition molecule is an antibody that is specific for the target. Ideally, recognition molecules are able to recognize targets with high sensitivity and selectivity. Such molecules are known, and can also be readily obtained using known methods. The enzyme (such as invertase) that can catalyze the conversion of a substance (such as sucrose) into glucose can be conjugated to the recognition molecule, resulting in for example, an aptamer-enzyme conjugate (such as an aptamer-invertase conjugate) or an Ab-enzyme conjugate (such as an Ab-invertase conjugate). In a specific example, the recognition molecule is a DNA aptamer specific for a pathogen, such as the hepatitis B surface antigen (HBsAg) or the Tat protein for HIV, and is conjugated to invertase. Such aptamers can be generated using known methods.[49] Other exemplary recognition molecules and enzymes that can catalyze the conversion of a substance (such as sucrose) into glucose are provided herein.

The lateral flow device can include a wicking pad, conjugation pad, membrane, absorption pad, and combinations thereof. Such pads can abut one another or overlap, and can be attached to a backing. Exemplary materials that can be used for the components of a lateral flow device are shown in Table 1. However, one of skill in the art will recognize that the particular materials used in a particular lateral flow device will depend on a number of variables, including, for example, the analyte to be detected, the sample volume, the desired flow rate and others, and can routinely select the useful materials accordingly.

TABLE 1

Exemplary materials for a lateral flow device

| Component | Exemplary Material |
|---|---|
| Wicking Pad | Glass fiber |
| | Woven fibers |
| | Screen |
| | Non-woven fibers |
| | Cellulosic filters |
| | Paper |
| Conjugation Pad | Glass fiber |
| | Polyester |
| | Paper |
| | Surface modified polypropylene |
| Membrane | Nitrocellulose (including pure nitrocellulose and modified nitrocellulose) |
| | Nitrocellulose direct cast on polyester support |
| | Polyvinylidene fluoride |
| | Nylon |
| Absorption Pad | Cellulosic filters |
| | Paper |

The sample known or suspected of containing one or more target agents is applied to or contacted with the wicking pad (which is usually at the proximal end of the device, but can for example be at the center of the device for example when multiple conjugation pads are included to detect multiple targets), for instance by dipping or spotting. A sample is collected or obtained using methods well known to those skilled in the art. The sample containing the test agent to be detected may be obtained from any source. The sample may be diluted, purified, concentrated, filtered, dissolved, suspended or otherwise manipulated prior to assay to optimize the results. The fluid sample migrates distally through all the functional regions of the strip. The final distribution of the fluid in the individual functional regions depends on the adsorptive capacity and the dimensions of the materials used.

The wicking pad ensures that the sample moves through the device in a controllable manner, such that it flows in a unilateral direction. The wicking pad initially receives the sample, and can serve to remove particulates from the sample. Among the various materials that can be used to construct a sample pad (see Table 1), a cellulose sample pad may be beneficial if a large bed volume (e.g., 250 µl/cm$^2$) is a factor in a particular application. In one example, the wicking pad is made of Millipore cellulose fiber sample pads (such as a 10 to 25 mm pad, such as a 15 mm pad). Wicking pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

After contacting the sample to the wicking pad, the sample liquid migrates from bottom to the top because of capillary force (or from the center outwards). The sample then flows to the conjugation pad, which serves to, among other things, hold the recognition molecule-enzyme conjugate. The recognition molecule-enzyme conjugate can be immobilized to the conjugation pad by spotting (for example the recognition molecule-enzyme conjugate, such as an invertase/aptamer conjugate, can be suspended in water or other suitable buffer and spotted onto the conjugation pad and allowed to dry). The conjugation pad can be made of known materials (see Table 1), such as glass fiber, such as one that is 10 to 25 mm, for example 13 mm. When the sample reaches the conjugation pad, target agent present in the sample can bind to the recognition molecule-enzyme immobilized to the conjugation pad, resulting in the release of the enzyme (such as the recognition molecule-enzyme complex) from the conjugation pad. The recognition molecule-enzyme conjugate is released because the recognition molecule (e.g., aptamer or Ab) has a higher affinity to the target agent than the immobilized surface (for example, the surface is modified by the target agent's analogue of lower binding affinity). In a particular disclosed embodiment, the recognition molecule-enzyme associated with the conjugation pad is an immobilized DNA aptamer-invertase conjugate or an immobilized Ab-invertase conjugate, for example immobilized to a bead.

The released enzyme (such as the recognition molecule-enzyme complex) then flows to the membrane coated by an agent that the enzyme conjugated to the recognition molecule can convert to glucose (e.g., sucrose). Then, the released enzyme (e.g., invertase) catalyzes the production of glucose from sucrose (or other compound the enzyme can convert to glucose) in the membrane coated by sucrose (or other agent that the enzyme conjugated to the enzyme can convert to glucose, see Table 2). The membrane portion can be made of known materials (see Table 1), such as a HiFlow Plus Cellulose Ester Membrane, such as one that is 10 to 40 mm, for example 25 mm. Methods that can be used to attach the sucrose or other substance to the membrane include spotting (for example the sucrose or other substance can be suspended in water or other suitable buffer and spotted onto the membrane and allowed to dry).

Finally, the glucose produced in the membrane moves with the flow and reaches the absorption pad, where it is then detected by a connected PGM. The absorbent pad acts to draw the sample across the conjugation pad and membrane by capillary action and collect it. This action is useful to insure the sample solution will flow from the sample or wicking pad unidirectionally through conjugation pad and the membrane to the absorption pad. Any of a variety of materials is useful to prepare an absorbent pad, see, for example, Table 1. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad. In one example the absorption is one that is 10 to 25 mm, for example 15 mm.

The amount of glucose detected by the PGM, enzyme or recognition molecule-enzyme complex released, and target agent are proportional to each other, thus the target agent can be quantified by the read out of glucose meter. The original glucose concentration in the sample can be subtracted from the result for more accurate quantification of the target agent. Because of high selectivity of the recognition molecule (e.g., aptamer or Ab) for its target, interference by other components in the sample is minimal.

A specific exemplary lateral flow device is shown in FIG. 24. The lateral flow device includes a bibulous lateral flow strip, which can be present in housing material (such as plastic or other material). The lateral flow strip is divided into a proximal wicking pad, a conjugation pad (containing an immobilized aptamer-invertase conjugate), a membrane coated with sucrose, and a distal absorption pad. The flow path along strip passes from proximal wicking pad, through conjugation pad, into the membrane coated with sucrose, for eventual collection in absorption pad.

In operation of the particular embodiment of a lateral flow device illustrated in FIG. 24, a fluid sample containing a target of interest (or suspected of containing such), such as a metal target agent, is applied to the wicking pad, for example dropwise or by dipping the end of the device into the sample. If the sample is whole blood, an optional developer fluid can be added to the blood sample to cause hemolysis of the red blood cells and, in some cases, to make an appropriate dilution of the whole blood sample. From the wicking pad, the sample passes, for instance by capillary action, to the conjugation pad. In the conjugation pad, the target of interest binds the immobilized aptamer-invertase conjugate. For example, if the recognition molecule is specific for IFN-γ, IFN-γ in the sample will bind to the immobilized IFN-γ aptamer-invertase conjugate contained in the conjugation pad. After this binding, the invertase of the conjugate is released, and can subsequently flow to the membrane where the invertase can interact with sucrose present on the membrane, thereby producing glucose. The resulting glucose can subsequently flow to the absorption pad, which can be read by a glucose meter, wherein the presence of glucose indicates the presence of target agent in the sample tested.

Recognition Molecules that Permit Detection of the Target Agent

The recognition molecule that specifically binds to the target agent, and thus permits detection of the target agent, can be a nucleic acid molecule, protein, peptide nucleic acid, polymer, small organic moleucle, an antibody, and the like. For example, the molecule that specifically binds to the target agent can be any substance that specifically binds to the target agent, and upon such binding, the molecule undergoes changes such as folding, binding or releasing, which in some examples causes release of an enzyme conjugated to the molecule.

In one example the molecule that specifically binds to the target agent is an antibody (such as a monoclonal or polyclonal antibody or fragment thereof) or antigen. Antibodies that are specific for a variety of target agents are commercially available, or can be generated using routine methods.

In one example the molecule that specifically binds to the target agent is protein that binds with high specificity to the target agent.

In yet another example, the molecule that specifically binds to the target agent is a nucleic acid or other analogue, such as a peptide nucleic acid (PNA), locked nucleic acid (LNA), or any chemically modified nucleotide analogue. For example, the nucleic acid molecule can be composed of DNA or RNA, such as one that includes naturally occurring and/or modified bases. In an example when the target is a nucleic acid molecule (such as DNA or RNA) the recognition nucleic acid molecule can have a sequence that is complementary to the sequence of the target nucleic acid molecule, such that the target nucleic acid and recognition molecule can hybridize to one another. In one example, the nucleic acid molecule is a ribozyme which can detect a corresponding cofactor or target agent. A ribozyme is an RNA molecule with catalytic activity, for example RNA splicing activity. When ribozymes function, they often require a cofactor, such as metal ions (e.g., $Mg^{2+}$) for their enzymatic activity. Such a cofactor can be the target agent detected based on ribozyme activity. Thus, as cofactors support ribozyme activity and ribozyme activity can be an indicator of the presence of the cofactor, or target agent.

Functional DNA

Besides proteins, nucleic acids have also been found to have catalytic activities in recent years. The catalytic active nucleic acids can be catalytic DNA/RNA, also known as DNAzymes/RNAzymes, deoxyribozymes/ribozymes, and DNA enzymes/RNA enzymes. Catalytic active nucleic acids can also contain modified nucleic acids. Nucleic acids may be selected to bind to a wide range of analytes with high affinity and specificities. These binding nucleic acids are known as aptamers.

Aptamers are nucleic acids (such as DNA or RNA) that recognize targets with high affinity and specificity. Aptazymes (also called allosteric DNA/RNAzymes or allosteric (deoxy) ribozymes) are DNA/RNAzymes regulated by an effector (the target molecule). They typically contain an aptamer domain that recognizes an effector and a catalytic domain. The effector can either decrease or increase the catalytic activity of the aptazyme through specific interactions between the aptamer domain and the catalytic domain. Therefore, the activity of the aptazyme can be used to monitor the presence and quantity of the effector. In addition, general strategies to design DNA aptazymes, by introducing aptamer motifs close to the catalytic core of DNAzymes, are available (Wang et al., *J. Mol. Biol.*, 318:33-43, 2002). High cleavage activity requires the presence of effector molecules that upon binding to the aptamer motif, can allosterically modulate the activity of the catalytic core part of the aptazyme.

In vitro selection methods can be used to obtain aptamers for a wide range of target molecules with exceptionally high affinity, having dissociation constants as high as in the picomolar range (Brody and Gold, *J. Biotechnol.* 74: 5-13, 2000; Jayasena, *Clin. Chem.*, 45:1628-1650, 1999; Wilson and Szostak, *Annu. Rev. Biochem.* 68: 611-647, 1999). For example, aptamers have been developed to recognize metal ions such as Zn(II) (Ciesiolka et al., *RNA* 1: 538-550, 1995) and Ni(II) (Hofmann et al., *RNA*, 3:1289-1300, 1997); nucleotides such as adenosine triphosphate (ATP) (Huizenga and Szostak, *Biochemistry*, 34:656-665, 1995); and guanine (Kiga et al., *Nucleic Acids Research*, 26:1755-60, 1998); co-factors such as NAD (Kiga et al., *Nucleic Acids Research*, 26:1755-60, 1998) and flavin (Lauhon and Szostak, *J. Am. Chem. Soc.*, 117:1246-57, 1995); antibiotics such as viomycin (Wallis et al., *Chem. Biol.* 4: 357-366, 1997) and streptomycin (Wallace and Schroeder, *RNA* 4:112-123, 1998); proteins such as HIV reverse transcriptase (Chaloin et al., *Nucleic Acids Research*, 30:4001-8, 2002) and hepatitis C virus RNA-dependent RNA polymerase (Biroccio et al., J. *Virol.* 76:3688-96, 2002); toxins such as cholera whole toxin and staphylococcal enterotoxin B (Bruno and Kiel, *BioTechniques*, 32: pp. 178-180 and 182-183, 2002); and bacterial spores such as the anthrax (Bruno and Kiel, *Biosensors & Bioelectronics*, 14:457-464, 1999). Compared to antibodies, DNA/RNA based aptamers are easier to obtain and less expensive to produce because they are obtained in vitro in short time periods (days vs. months) and with limited cost. In addition, DNA/RNA aptamers can be denatured and renatured many times without losing their biorecognition ability.

Typically, a DNA/RNAzyme- or aptazyme-based sensor has three parts:
 (1) a nucleic acid enzyme (e.g., DNA/RNAzymes and aptazymes) and a co-factor, such as a metal ion that catalyzes substrate cleavage;
 (2) a nucleic acid substrate for the nucleic acid enzyme, wherein interior portions of the substrate sequence is complementary to portions of the enzyme sequence; and
 (3) species attached to polynucleotides that are complementary to the 3'- and 5'-termini of the substrate.

In one example, the nucleic acid molecule is a functional nucleic acid, such as an aptamer, DNAzyme, or aptazyme. Aptamers are a double-stranded DNA or single-stranded RNA that binds to a specific target, such as a target agent provided herein. For example, the adenosine aptamer binds adenosine as its corresponding target. In yet another example, the molecule that specifically binds to the target agent is a DNAzyme or catalytic DNA or DNA enzymes. DNAzymes are DNA molecules that have enzymatic activities. They are similar to ribozymes, but consist of DNA instead of RNA. Therefore DNAzymes are also called deoxyribozymes, catalytic DNA, or DNA enzymes. Like ribozymes, DNAzymes require a co-factor, such as a metal ion, to have catalytic activity. Thus, DNAzymes can also be used to detect target agent metal ions. Aptazymes are the combination of aptamer and DNAzymes or ribozymes. Aptazymes work when the target agent binds to the aptamers which either triggers DNAzyme/ribozyme activities or inhibits DNAzyme/ribozyme activities.

In one example the molecule that specifically binds to the target agent is a functional DNA.[14] Functional DNAs, including DNAzymes[15,16] (also named deoxyribozymes, catalytic DNAs or DNA enzymes) and DNA aptamers,[17,18] are selected from pools of DNA (usually 2~25 kDa) with ~$10^{15}$ random sequences via a process known as in vitro selection[16] or Systematic Evolution of Ligands by EXponential enrichment (SELEX).[18] These DNAzymes and aptamers exhibit specific catalytic activity and strong binding affinity, respectively, to various targets. The targets can range from metal ions and small organic molecules to biomolecules and even viruses or cells.[14,19] Therefore, functional DNAs can serve as the source of recognition of a target agent in the sensor.

Methods of identifying a functional DNA that is specific for a particular target agent are routine in the art and have been described in several patents (all herein incorporated by reference). For example U.S. Pat. Nos. 7,192,708; 7,332,283; 7,485,419; 7,534,560; and 7,612,185, and US Patent Publication Nos. 20070037171 and 20060094026, describe methods of identifying functional DNA molecules that can bind to particular ions, such as lead and cobalt. In addition, specific examples are provided. Although some of the examples describe functional DNA molecules with fluorophores, such labels are not required for the sensors described herein.

In addition, since the secondary structures of functional DNAs are predictable, it is straightforward to incorporate signal transduction parts into them and transform the interaction between functional DNAs and their targets into physically detectable signals. Many functional DNA sensors[14,20-28] for a broad range of analytes have been developed using various analytical techniques, such as colorimetry,[10,29-33] fluorescence,[34-38] electrochemistry,[39-44] and magnetic resonance.[45] However, until now, laboratory-based devices were required for quantitative detection in these designs.

Enzymes that can Convert a Substance into Glucose

Any enzyme that can convert a molecule (enzyme substrate) into glucose (6-(hydroxymethyl)oxane-2,3,4,5-tetrol; which can then be detected using a PGM), can be used in the sensors and methods provided herein. Although particular examples herein are provided using invertase, one skilled in the art will appreciate that other enzymes can be used. For example, any glucosidase (alpha or beta) can be used to produce glucose from the corresponding enzyme substrates. Particular examples are shown in the Table 2 below.

TABLE 2

Exemplary enzymes of the present disclosure

| Enzyme | Exemplary GenBank # | Enzyme Substrate | Product Detectable by Glucose Meter |
|---|---|---|---|
| Sucrase (EC 3.2.1.26) | Proteins: CBL50959.1; NP_001119607.1; AAA22723.1 Nucleic acids: NM_001126135.2; FN692037 REGION: 1525811..1526818; M15662 | Sucrose | Glucose |
| Sucrase-isomaltase (EC 3.2.1.10) | Proteins: AAA60551.1; NP_001074606.1; BAG16411.1 Nucleic Acids: NM_001114189.1; NM_001081137.1; AB428422 | Sucrose | Glucose |
| Maltase (EC 3.2.1.20) | Proteins: AAY57566.1; EDP48477.1; XP_748872.1 Nucleic Acids: DQ019991; NM_001178647 | Maltose | Glucose |
| Trehalase (EC 3.2.1.28) | Proteins: YP_001177075.1; CAA81270.1; NP_001129613.1; ZP_05439621.1 Nucleic Acids: Z26494 REGION: 7666..10008; NM_001136141; NC_012947 REGION: 240443..242092 | Trehalose | Glucose |
| Cellulase (EC 3.2.1.4) | Proteins: AAA23226.1; AAB60304.1; ACQ91268.1 Nucleic Acids: L06942; U37702; FJ941842 | Cellulose | Glucose |
| Amylase (EC 3.2.1.1; 3.2.1.2; 3.2.1.3) | Proteins: AAA22227.1; CAB61483.1 Nucleic Acids: M57457; AB020313 | Starch | Glucose |

To apply these enzymes in the sensors described herein, the invertase described in the examples below can be replaced by one of these enzymes and the sucrose replaced by the corresponding enzyme substrates listed above.

Although exemplary GENBANK® numbers are listed herein, the disclosure is not limited to the use of these sequences. Many other enzyme sequences are publicly available, and can thus be readily used in the disclosed methods. In one example, an enzyme having at least 70%, at least 75%, at least 80%, at least 85%, at least 90%, at least 95%, at least 98%, or at least 100% sequence identity to any of the GENBANK® numbers are listed herein that retains the ability to catalyze the conversion of an enzyme substrate into glucose, is used in the sensors disclosed herein. In addition, such enzymes that can be used with the disclosed sensors are available from commercial sources, such as Sigma-Aldrich (St. Louis, Mo.).

Conjugating the Enzyme or Solid Support to the Recognition Molecule

Methods of conjugating a recognition molecule that can specifically bind to the target agent (such as an antibody, polymer, protein or nucleic acid) to the enzyme or to the solid support (such as a conjugation pad) are conventional. The conjugation method used can be any chemistry that can covalently or non-covalently incorporate enzyme with other molecules. In some examples, a recognition molecule-enzyme complex is attached to a solid support, such as a conjugation pad of a lateral flow device, simply by suspending the recognition molecule-enzyme complex in a solution, applying the solution to the pad, and allowing the solution to dry.

In one example the method uses a reaction that forms covalent bonds including but not limited to those between amines and isothiocyanates, between amines and esters, between amines and carboxyls, between thiols and maleimides, between thiols and thiols, between azides and alkynes, and between azides and nitriles. In another example, the method uses a reaction that forms non covalent interactions including but not limited to those between antibodies and antigens, between aptamer and corresponding targets, and between organic chelators and metal ions.

In a specific example, invertase, an enzyme capable of efficiently catalyzing the hydrolytic reaction of sucrose, is conjugated to DNA by maleimide-thiol or isothiocyanate-amine reaction; then, the DNA-invertase conjugate is immobilized to magnetic beads via DNA hybridization with functional DNA on the beads. In the presence of a specific analyte, the DNA-invertase conjugate can be released from the functional DNA duplex on the magnetic beads through analyte-induced catalytic reaction of DNAzyme or structure switching of aptamer. The released DNA-invertase conjugate can efficiently catalyze the conversion of sucrose into glucose, which is subsequently quantified by a PGM and correlated with the concentration of the analyte in the sample.

Target Agents

The disclosed sensors can be designed to detect any target agent of interest. Thus, the methods and devices provided herein can be used to detect any target agent of interest, such as the specific examples provided herein. As described above, selecting an appropriate recognition molecule that permits detection of the target agent, allows one to develop a sensor that can be used to detect a particular target agent. Exemplary target agents are provided below; however one skilled in the art will appreciate that other target agents can be detected with the disclosed sensors and devices (such as the lateral flow devices provided herein) using the disclosed methods.

Metals

In one example the target agent is a metal (e.g., elements, compounds, or alloys that have high electrical conductivity), such as a heavy metal or a nutritional metal. Metals occupy the bulk of the periodic table, while non-metallic elements can only be found on the right-hand-side of the Periodic Table of the Elements. A diagonal line drawn from boron (B) to polonium (Po) separates the metals from the nonmetals. Most elements on this line are metalloids, sometimes called semi-conductors. Elements to the lower left of this division line are called metals, while elements to the upper right of the division line are called non-metals.

Heavy metals include any metallic chemical element that has a relatively high density and is toxic, highly toxic or poisonous at low concentrations. Examples of heavy metals include mercury (Hg), cadmium (Cd), arsenic (As), chromium (Cr), thallium (Tl), uranium (U), plutonium (Pu), and lead (Pb).

Nutritional metal ions include those important in animal nutrition and may be necessary for particular biological functions, include calcium, iron, cobalt, magnesium, manganese, molybdenum, zinc, cadmium, and copper.

Pathogens/Microbes

Any pathogen or microbe can be detected using the sensors and methods provided herein. For example, particular antimicrobial antigens and nucleic acid molecules (such as DNA or RNA), as well as bacterial spores, can be detected. In some examples, a particular microbial cell is detected, or a particular virus. In some examples, intact microbes are detected, for example by detecting a target surface protein (such as a receptor) using sensors that include for example antibodies or DNA aptamers specific for the target protein. In other examples, a conserved DNA or RNA specific to a target microbe is detected, for example by obtaining nucleic acids from a sample (such as from a sample known or suspected of containing the microbe), wherein the resulting nucleic acids (such as DNA or RNA or both) are then contacted with the sensors disclosed herein (which include the complementary nucleic acid sequence that can hybridize to the target nucleic acid).

Exemplary pathogens include, but are not limited to, viruses, bacteria, fungi, nematodes, and protozoa. A non-limiting list of pathogens that can be detected using the sensors provided herein are provided below.

For example, viruses include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepativiridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); Calciviridae (which includes Norovirus and Sapovirus); and Coronaviruses (examples of which include SARS coronaviruses, such as the Urbani strain).

Exemplary negative-strand RNA viruses include, but are not limited to: Orthomyxoviruses (such as the influenza virus), Rhabdoviruses (such as Rabies virus), and Paramyxoviruses (examples of which include measles virus, respiratory syncytial virus, and parainfluenza viruses).

Viruses also include DNA viruses. DNA viruses include, but are not limited to: Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19).

Another group of viruses includes Retroviruses. Examples of retroviruses include, but are not limited to: human immunodeficiency virus type 1 (HIV-1), such as subtype C; HIV-2; equine infectious anemia virus; feline immunodeficiency virus (FIV); feline leukemia viruses (FeLV); simian immunodeficiency virus (SIV); and avian sarcoma virus.

In one example, the sensor can distinguish between an infectious versus a non-infectious virus.

Pathogens also include bacteria. Bacteria can be classified as gram-negative or gram-positive. Exemplary gram-negative bacteria include, but are not limited to: *Escherichia coli* (e.g., K-12 and O157:H7), *Shigella dysenteriae*, and *Vibrio cholerae*. Exemplary gram-positive bacteria include, but are not limited to: *Bacillus anthracis, Staphylococcus aureus*, pneumococcus, gonococcus, and streptococcal meningitis.

Protozoa, nemotodes, and fungi are also types of pathogens. Exemplary protozoa include, but are not limited to, *Plasmodium, Leishmania, Acanthamoeba, Giardia, Entamoeba, Cryptosporidium, Isospora, Balantidium, Trichomonas, Trypanosoma, Naegleria*, and *Toxoplasma*. Exemplary fungi include, but are not limited to, *Coccidiodes immitis* and *Blastomyces dermatitidis*.

In one example, bacterial spores are detected. For example, the genus of *Bacillus* and *Clostridium* bacteria produce spores that can be detected. Thus, *C. botulinum, C. perfrin-* gens, *B. cereus*, and *B. anthracis* spores can be detected (for example detecting anthrax spores). One will also recognize that spores from green plants can also be detected using the methods and devices provided herein.

Proteins

The disclosed sensors also permit detection of a variety of proteins, such as cell surface receptors, cytokines, antibodies, hormones, as well as toxins. In particular examples, the recognition molecule that can specifically bind to the protein target is a protein (such as an antibody) or nucleic acid (such as a functional nucleic acid)

In one example the protein is a cytokine. Cytokines are small proteins secreted by immune cells that have effects on other cells. Examples include interleukins (IL) and interferons (IFN), and chemokines, such as IL-1, IL-2, IL-4, IL-6, IL-8, IL-10, IFN-γ, IFN-β, transforming growth factor (TGF-β), and tumor necrosis factor (TNF)-α.

In one example the protein is a hormone. A hormone is a chemical messenger that transports a signal from one cell to another. Examples include plant and animal hormones, such as endocrine hormones or exocrine hormones. Particular examples include follicle stimulating hormone (FSH), human chorionic gonadotropin (hCG), thyroid stimulating hormone (TSH), growth hormone, progesterone, and the like.

In yet another example the protein is a toxin. Toxins are poisonous substances produced by cells or organisms, such as plants, animals, microorganisms (including, but not limited to, bacteria, viruses, fungi, rickettsiae or protozoa). Particular examples include botulinum toxin, ricin, diphtheria toxin, Shiga toxin, Cholera toxin, and anthrax toxin. In another example, the toxin is an environmental toxin.

In another example, the protein is one found on the surface of a target microbe or cell, such as a bacterial cell, virus, spore, or tumor cell. Such proteins, such as receptors, may be specific for the microbe or cell (for example HER2, IGF1R, EGFR or other tumor-specific receptor noted below in "nucleic acids"). In on example the protein is prostate-specific antigen (PSA, for example GenBank® Accession No. NP_001025218).

Nucleic Acids

The disclosed sensors also permit detection of nucleic acid molecules, such DNA and RNA, such as a DNA or RNA sequence that is specific for a particular pathogen or cell of interest. For example, target pathogens can have conserved DNA or RNA sequences specific to that pathogen (for example conserved sequences are known in the art for HIV, bird flu and swine flu), and target cells may have specific DNA or RNA sequences unique to that cell, or provide a way to distinguish a target cell from another cell (such as distinguish a tumor cell from a benign cell).

In some examples, a target sequence is selected that is associated with a disease or condition, such that detection of hybridization between the target nucleic acid and a sensor provided herein can be used to infer information (such as diagnostic or prognostic information for the subject from whom the sample is obtained) relating to the disease or condition.

In specific non-limiting examples, a target nucleic acid sequence associated with a tumor (for example, a cancer) is selected. Numerous chromosome abnormalities (including translocations and other rearrangements, reduplication (amplification) or deletion) have been identified in neoplastic cells, especially in cancer cells, such as B cell and T cell leukemias, lymphomas, breast cancer, colon cancer, neurological cancers and the like.

Exemplary target nucleic acids include, but are not limited to: the SYT gene located in the breakpoint region of chromosome 18q11.2 (common among synovial sarcoma soft tissue tumors); HER2, also known as c-erbB2 or HER2/neu (a representative human HER2 genomic sequence is provided at GENBANK® Accession No. NC_000017, nucleotides 35097919-35138441) (HER2 is amplified in human breast, ovarian, gastric, and other cancers); p16 (including D9S1749, D9S1747, p16(INK4A), p14(ARF), D9S1748, p15(INK4B), and D9S1752) (deleted in certain bladder cancers); EGFR (7p12; e.g., GENBANK® Accession No. NC_000007, nucleotides 55054219-55242525), MET (7q31; e.g., GENBANK® Accession No. NC_000007, nucleotides 116099695-116225676), C-MYC (8q24.21; e.g., GENBANK® Accession No. NC_000008, nucleotides 128817498-128822856), IGF1R (15q26.3; e.g., GENBANK® Accession No. NC_000015, nucleotides 97010284-97325282), D5S271 (5p15.2), KRAS (12p12.1; e.g. GENBANK® Accession No. NC_000012, complement, nucleotides 25249447-25295121), TYMS (18p11.32; e.g., GENBANK® Accession No. NC_000018, nucleotides 647651-663492), CDK4 (12q14; e.g., GENBANK® Accession No. NC_000012, nucleotides 58142003-58146164, complement), CCND1 (11q13, GENBANK® Accession No. NC_000011, nucleotides 69455873-69469242), MYB (6q22-q23, GENBANK® Accession No. NC_000006, nucleotides 135502453-135540311), lipoprotein lipase (LPL) (8p22; e.g., GENBANK® Accession No. NC_000008, nucleotides 19840862-19869050), RB1 (13q14; e.g., GENBANK® Accession No. NC_000013, nucleotides 47775884-47954027), p53 (17p13.1; e.g., GENBANK® Accession No. NC_000017, complement, nucleotides 7512445-7531642), N-MYC (2p24; e.g., GENBANK® Accession No. NC_000002, complement, nucleotides 15998134-16004580), CHOP (12q13; e.g., GENBANK® Accession No. NC_000012, complement, nucleotides 56196638-56200567), FUS (16p11.2; e.g., GENBANK® Accession No. NC_000016, nucleotides 31098954-31110601), FKHR (13p14; e.g., GENBANK® Accession No. NC_000013, complement, nucleotides 40027817-40138734), aALK (2p23; e.g., GENBANK® Accession No. NC_000002, complement, nucleotides 29269144-29997936), Ig heavy chain, CCND1 (11q13; e.g., GENBANK® Accession No. NC_000011, nucleotides 69165054-69178423), BCL2 (18q21.3; e.g., GENBANK® Accession No. NC_000018, complement, nucleotides 58941559-59137593), BCL6 (3q27; e.g., GENBANK® Accession No. NC_000003, complement, nucleotides 188921859-188946169), AP1 (1p32-p31; e.g., GENBANK® Accession No. NC_000001, complement, nucleotides 59019051-59022373), TOP2A (17q21-q22; e.g., GENBANK® Accession No. NC_000017, complement, nucleotides 35798321-35827695), TMPRSS (21q22.3; e.g., GENBANK® Accession No. NC_000021, complement, nucleotides 41758351-41801948), ERG (21q22.3; e.g., GENBANK® Accession No. NC_000021, complement, nucleotides 38675671-38955488); ETV1 (7p21.3; e.g., GENBANK® Accession No. NC_000007, complement, nucleotides 13897379-13995289), EWS (22q12.2; e.g., GENBANK® Accession No. NC_000022, nucleotides 27994017-28026515); FLI1 (11q24.1-q24.3; e.g., GENBANK® Accession No. NC_000011, nucleotides 128069199-128187521), PAX3 (2q35-q37; e.g., GENBANK® Accession No. NC_000002, complement, nucleotides 222772851-222871944), PAX7 (1p36.2-p36.12; e.g., GENBANK® Accession No. NC_000001, nucleotides 18830087-18935219), PTEN (10q23.3; e.g., GENBANK® Accession No. NC_000010, nucleotides 89613175-89718512), AKT2 (19q13.1-q13.2; e.g., GENBANK®

Accession No. NC_000019, complement, nucleotides 45428064-45483105), MYCL1 (1p34.2; e.g., GENBANK® Accession No. NC_000001, complement, nucleotides 40133685-40140274), REL (2p13-p12; e.g., GENBANK® Accession No. NC_000002, nucleotides 60962256-61003682) and CSF1R (5q33-q35; e.g., GENBANK® Accession No. NC_000005, complement, nucleotides 149413051-149473128).

In examples where the target molecule is a nucleic acid molecule, the sample to be tested can be treated with agents that permit disruption of the cells or pathogen. The nucleic acid molecules can be extracted or isolated, and then exposed to a sensor disclosed herein, such as one having the complementary DNA-conjugated to invertase (or other enzyme listed in Table 2). That is, the sensor includes a DNA molecule as the recognition molecule having a sequence that is complementary to the target DNA or RNA sequence, such that the complementary nucleic acid sequence can hybridize to the target nucleic acid, thereby permitting detection of the target nucleic acid.

Recreational and Other Drugs

The disclosed sensors also permit detection of a variety of drugs, such as pharmaceutical or recreational drugs. For example, the presence of caffeine, cocaine, opiates and opioids (such as oxycodone), cannabis (for example by detecting tetrahydrocannabinol (THC)), heroin, methamphetamines, crack, ethanol, or tobacco (for example by detecting nicotine), can be detected using the disclosed sensors and devices. In particular examples, the recognition molecule that can specifically bind to the drug target is a protein is a nucleic acid (such as a functional nucleic acid)

Cells

The disclosed sensors also permit detection of a variety of cells, such as tumor or cancer cells, as well as other diseased cells. In on example, the sensor can distinguish between a tumor cell and a normal cell of the same cell type, such as a normal breast cell from a cancerous breast cell. Tumors are abnormal growths which can be either malignant or benign, solid or liquid (for example, hematogenous). In some examples, cells are detected by using a sensor that includes a recognition molecule specific for a surface protein, such as a receptor on the surface of the cell. In other examples, cells are detected by using a sensor that includes a recognition molecule specific for a nucleic acid found in the tumor cell.

Examples of hematological tumors include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (including low-, intermediate-, and high-grade), multiple myeloma, Waldenstrom's macroglobulinemia, heavy chain disease, myelodysplastic syndrome, mantle cell lymphoma and myelodysplasia.

Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Thus, in some examples the sensors and devices provided herein permit detection of such tumor cells using the disclosed methods.

Kits

The disclosure also provides kits that include one or more of the sensors disclosed herein, for example sensors that are part of a lateral flow device. For example, a kit can include at least 2 different sensors permitting detection of at least two different target agents, such as at least 3, at least 4, at least 5, or at least 10 different sensors. In a specific example, a kit can include at least 2 different lateral flow devices permitting detection of at least two different target agents, such as at least 3, at least 4, at least 5, or at least 10 different lateral flow devices.

The kits can the sensor or lateral flow device and a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can retain, for example, one or more biological samples to be tested, positive and/or negative control samples or solutions (such as, a positive control sample containing the target agent), diluents (such as, phosphate buffers, or saline buffers), a PGM, and/or wash solutions (such as, Tris buffers, saline buffer, or distilled water).

Such kits can include other components, such as a buffer, a chart for correlating detected glucose level and amount of target agent present, the substance that the enzyme can convert into glucose, or combinations thereof. For example, the kit can include a vial containing one or more of the sensors disclosed herein and a separate vial containing the substance that the enzyme can convert into glucose. Exemplary substances that the enzyme can convert into glucose include but are not limited to sucrose, maltose, trehalose, cellulose, and starch. In one example, the kit also includes an unnatural precursor of these sugars, such as O-methylated glucose. For example, O-methylated glucose can be present in a glucose meter, and after the enzyme reaction, O-methylated glucose is converted to glucose, and can be detected by glucose meter.

Other kit embodiments include syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing a biological sample. Kits may also optionally contain implements useful for introducing samples onto a lateral flow device, including, for example, droppers, Dispo-pipettes, capillary tubes, rubber bulbs (e.g., for capillary tubes), and the like. Still other kit embodiments may include disposal means for discarding a used device and/or other items used with the device (such as patient samples, etc.). Such disposal means can include, without limitation, containers that are capable of containing leakage from discarded materials, such as plastic, metal or other impermeable bags, boxes or containers.

In some examples, a kit will include instructions for the use of a sensor or lateral flow device. The instructions may provide direction on how to apply sample to the sensor or device, the amount of time necessary or advisable to wait for results to develop, and details on how to read and interpret the results of the test. Such instructions may also include standards, such as standard tables, graphs, or pictures for comparison of the results of a test. These standards may optionally include the information necessary to quantify target analyte using the sensor or device, such as a standard curve relating amount of glucose detected to an amount of target analyte therefore present in the sample.

Methods of Detecting Target Agents Using the Sensor

Methods of using the sensors and devices disclosed herein to detect a target agent are provided herein. In one example, the method includes contacting one or more sensors with a sample under conditions sufficient to allow the target agent that may be present in the sample to bind to the recognition molecule (which is immobilized to the solid support, such as a lateral flow device). The disclosed sensors, including lateral flow devices, can be used in methods for detecting a target agent, for example to diagnose a disease or infection, or to detect exposure to a particular metal or drug.

In some examples, such binding can release the enzyme (such as the enzyme analyte analogue conjugate) from the solid support (for example due to competitive binding between the target agent and an enzyme analyte analogue conjugate). The solid support is separated or otherwise removed from the released enzyme. The released enzyme is then contacted with the substance that the enzyme can convert into glucose, thereby generating glucose. The resulting glucose is then detected, for example with a PGM, wherein detection of glucose indicates the presence of the target agent in the sample, and an absence of detected glucose indicates the absence of the target agent in the sample.

In other examples, binding of the target agent to the recognition molecule is followed by incubating the enzyme (such as an enzyme analyte analogue conjugate) under conditions sufficient to allow binding of the enzyme to the target agent bound to the recognition molecule. This results in the formation of a "sandwich" type structure, wherein the recognition molecule is bound to the solid support and the target agent, and the enzyme is bound (directly or indirectly, for example via an enzyme analyte analogue conjugate) to the target agent (and in some examples also the recognition molecule). In this example, the solid support need not be separated or otherwise removed from the enzyme. The bound enzyme is then contacted with the substance that the enzyme can convert into glucose, thereby generating glucose. The resulting glucose is then detected, for example with a PGM, wherein detection of glucose indicates the presence of the target agent in the sample, and an absence of detected glucose indicates the absence of the target agent in the sample.

In some examples, for example when the sensor is part of a lateral flow device, the method can include contacting the lateral flow device with a sample under conditions sufficient to allow the target agent in the sample to flow through the lateral flow device and bind to the recognition molecule present on the lateral flow device. The recognition molecule can be attached to the enzyme (such as invertase or other enzyme in Table 2) that converts a substance into glucose. Thus, the target agent is allowed to bind to the recognition molecule-enzyme complex, thereby forming a target agent-recognition molecule complex, wherein formation of the target agent-recognition molecule complex results in the release of the enzyme that can convert the substance into glucose. The enzyme is then allowed to interact with the substance (such as sucrose or other enzyme substrate listed in Table 2) that the enzyme can convert into glucose, thereby generating glucose. The resulting glucose is detected, wherein detection of glucose indicates the presence of the target agent in the sample, and an absence of detected glucose indicates the absence of the target agent in the sample.

The method can further include quantifying the target agent, wherein a level of glucose detected indicates an amount of target agent present.

In some examples, the enzyme comprises invertase, sucrase, or sucrase-isomaltase and the substance that the enzyme can convert into glucose comprises sucrose, or the enzyme comprises maltase and the substance that the enzyme can convert into glucose comprises maltose, or the enzyme comprises trehalase and the substance that the enzyme can convert into glucose comprises trehalose, or the enzyme comprises cellulase and the substance that the enzyme can convert into glucose comprises cellulose, or the enzyme comprises amylase and the substance that the enzyme can convert into glucose comprises starch.

Samples

Any biological or environmental specimen that may contain (or is known to contain or is suspected of containing) a target agent can be used. Biological samples are usually obtained from a subject and can include genomic DNA, RNA (including mRNA), protein, or combinations thereof. Examples include a tissue or tumor biopsy, fine needle aspirate, bronchoalveolar lavage, pleural fluid, spinal fluid, saliva, sputum, surgical specimen, lymph node fluid, ascites fluid, peripheral blood (such as serum or plasma), urine, saliva, buccal swab, and autopsy material. Techniques for acquisition of such samples are well known in the art (for example see Schluger et al. *J. Exp. Med.* 176:1327-33, 1992, for the collection of serum samples). Serum or other blood fractions can be prepared in the conventional manner. Samples can also include fermentation fluid and tissue culture fluid.

Environmental samples include those obtained from an environmental media, such as water, air, soil, dust, wood, plants or food.

In other examples, a sample includes a control sample, such as a sample known to contain or not contain a particular amount of the target agent.

In one example the sample is a food sample, such as a meat, fruit, or vegetable sample. For example, using the methods provided herein, adulterants in food products can be detected, such as a pathogen or toxin or other harmful product.

Once a sample has been obtained, the sample can be used directly, concentrated (for example by centrifugation or filtration), purified, liquefied, diluted in a fluid, or combinations thereof. In some examples, proteins or nucleic acids or pathogens are extracted from the sample, and the resulting preparation (such as one that includes isolated DNA and/or RNA) analyzed using the methods provided herein.

EXAMPLE 1

Materials and Methods

Streptavidin-coated magnetic beads, PD-10 size-exclusion columns, and Amicon-100K centrifugal filters were purchased from Bangs Laboratories Inc. (Fishers, Ind.), GE Healthcare Life Science Ltd. (Piscataway, N.J.) and Millipore Inc. (Billerica, Mass.), respectively. Invertase from baker's yeast (*S. cerevisiae*) of grade VII, human recombined interferon-γ (IFN-γ), sulfosuccinimidyl-4-(N-maleimidomethyl) cyclohexane-1-carboxylate (sulfo-SMCC), 1,4-phenylene diisothiocyanate (PDITC), Tris(2-carboxyethyl)phosphine hydrochloride (TCEP) and other chemicals for buffers and solvents were purchased from Sigma-Aldrich Inc. (St. Louis, Mo.). The following oligonucleotides were purchased from Integrated DNA Technologies Inc. (Coralville, Iowa):

```
Biotin-modified DNA (Biotin-DNA):
                                                (SEQ ID NO: 1)
TCACAGATGAGTAAAAAAAAAAAA-biotin'

Thiol-modified DNA (Thiol-DNA):
                                                (SEQ ID NO: 2)
HS-AAAAAAAAAAAAGTCTCCCGAGAT-FAM'

Amine-modified DNA (Amine-DNA)
                                                (SEQ ID NO: 3)
H2N-AAAAAAAAAAAACCCAGGTTCTCT-FAM'

Cocaine aptamer (Coc-Apt):
                                                (SEQ ID NO: 4)
TTTTTTACTCATCTGTGAATCTCGGGAGACAAGGATAAATCCTTCAATGAAGTGGGTCTCCC Cocaine aptamer control (Coc-Apt with underlined part removed):
                                                (SEQ ID NO: 5)
TTTTTTACTCATCTGTGAATCTCGGGAGAC Adenosine aptamer (Ade-Apt):
                                                (SEQ ID NO: 6)
TTTTTTACTCATCTGTGAAGAGAACCTGGGGGAGTATTGCGGAGGAAGGT Adenosine aptamer control (Ade-Apt with underlined part removed):
                                                (SEQ ID NO: 7)
TTTTTTACTCATCTGTGAAGAGAACCTGGG Biotin-modified DNA for IFN-γ (Biotin-DNA for IFN-γ):
                                                (SEQ ID NO: 8)
biotin-AAAAAAAAAAAATCACAGATGAGTAGT Thiol-modified DNA for IFN-γ:
                                                (SEQ ID NO: 9)
5'-HS-AAAAAAAAAAAACAACCAACCCCA-FAM IFN-γ aptamer (IFN-γ Apt):
                                                (SEQ ID NO: 10)
TGGGGTTGGTTGTGTTGGGTGTTGTGTAAAAAAAAAAAAAACTACTCATCTGTGA UO2^2+-dependent DNAzyme (39E):
                                                (SEQ ID NO: 11)
CACGTCCATCTCTGCAGTCGGGTAGTTAAACCGACCTTCAGACATAGTGAGT Substrate of UO2^2+-dependent DNAzyme (39S):
                                                (SEQ ID NO: 12)
ACTCATCTGTGAACTCACTATrAGGAAGAGATGGACGTGATCTCGGGAGAC
(the rA means the nucleotide is a RNA nucleotide, while other
nucleotides are DNA nucleotides)
```

Buffers used:
Buffer A: 0.1 M sodium phosphate (PBS) buffer, pH 7.3, 0.1 M NaCl
Buffer B: 0.1 M sodium borate buffer, pH 9.2
Buffer C: 0.01 M 4-(2-hydroxyethyl)-1-piperazineethanesulfonic acid (HEPES), pH 7.4, 0.1 M KCl, 0.001 M $MgCl_2$, 0.05% Tween-20
Buffer D: 0.05 M 2-(N-morpholino)ethanesulfonic acid (MES) buffer, pH 5.5, 0.2 M NaCl
Synthesis of DNA-Invertase Conjugate (Scheme 2)[56]
(1) Conjugate Using Heterobifunctional Linker Sulfo-SMCC To 30 μL 1 mM Thiol-DNA in Millipore water, 2 μL 1 M PBS buffer at pH 5.5 and 2 μL 30 mM TCEP in Millipore water were added and mixed. The mixture was kept at room temperature for 1 hour, and then purified by PD-10 column using Buffer A. This procedure was used to reduce disulfide bond and recover the active thiol group of Thiol-DNA (protected by disulfide bond as received from commercial source).

For invertase conjugation, 400 μL 20 mg/mL invertase in Buffer A was mixed with 1 mg sulfo-SMCC. After vortex for 5 minutes, the solution was placed on a shaking bead for 1 hour at room temperature. The mixture was centrifuged and the insoluble excess sulfo-SMCC was removed. The clear solution was then purified by PD-10 column using Buffer A.

The purified solution of sulfo-SMCC-activated invertase was mixed with the above solution of thiol-modified DNA. The volume of the solution mixture was reduced to ⅕ in vacuo. The resulting solution was kept at room temperature for 48 hours. To remove unreacted free Thiol-DNA, the solution was purified by Amicon-100K for 7 times using Buffer A.
(2) Conjugate Using Homobifunctional Linker PDITC To 60 μL 1 mM Amine-DNA in Millipore water, 30 μL Buffer B was added and mixed. This solution was further mixed with 20 mg PDITC dissolved in 1 mL DMF. The resulting solution was placed on a shaking bed and kept at room temperature in dark for 2 hours. After that, the solution was mixed with 6 mL Millipore water and 6 mL 1-butanol. By centrifuging for 15 min, the upper organic phase was discarded. The aqueous phase was then extracted with 4 mL 1-butanol for 3 times, and purified by PD-10 column using Buffer A to afford PDITC-activated Amine-DNA solution. The yield of PDITC activation to DNA was over 90% according to MALTI-TOF mass spectrum after desalting. A portion of 10 mg invertase was added to the activated DNA solution in Buffer A, and the volume of the solution was reduced to ⅕ in vacuo. The resulting solution was kept at 40° C. for 5 hours and room temperature for 24 hours, respectively. To remove unreacted PDITC-activated Amine-DNA, the solution was purified by Amicon-100K for 7 times using Buffer A.

Figure 6:
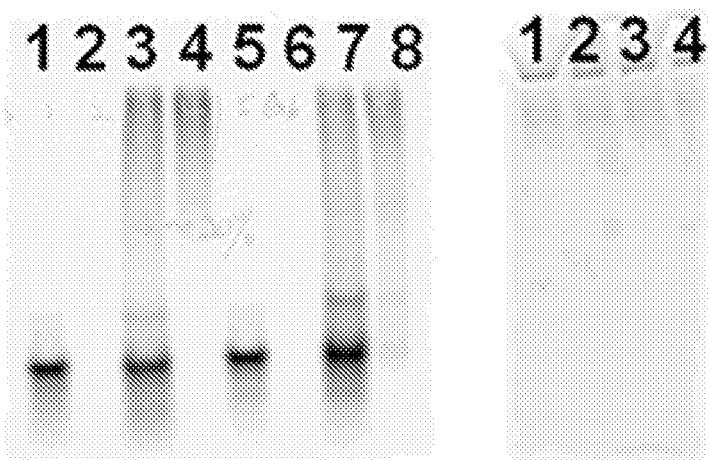
FIG. 6 is a digital image showing PAGE (4~20% gradient gel) images for the conjugation products. Left: fluorescence image of 1: Thiol-DNA and invertase without linker; 2: invertase; 3: Thiol-DNA and invertase with linker; 4: 3 after removal of DNA; 5: Amine-DNA and invertase without linker; 6: invertase; 7: Amine-DNA and invertase with linker; 8: 7 after removal of DNA. Right: protein-staining image of 1: Thiol-DNA and invertase without linker; 2: invertase; 3: Thiol-DNA and invertase with linker; 4: 3 after removal of DNA.

FIG. 6 shows the PAGE images of the above conjugation products. The DNAs were modified with FAM (fluorescein) so that DNA and DNA-invertase conjugate could be imaged by fluorescence. In another gel, invertase and DNA-invertase conjugate was stained by Coomassiebrilliantblue. DNA-invertase conjugate exhibited a broad fluorescent band (because the number of DNA conjugated to each protein can vary) that migrated very slowly, while free invertase was invisible in this fluorescent image. However, in the protein-stained image, very little difference was observed between DNA-invertase conjugate and free invertase except for the very faint tails (hardly visible in FIG. 6) for the conjugate. This could be ascribed to the molecular weight of invertase (135~270 kDa) was too large for migration in PAGE even if the protein was conjugated to DNA (7 kDa).

Preparation of the Sensors for Detection Using Commercially Available Personal Glucose Meter Thiol-DNA and Amine-DNA conjugated invertase synthesized as mentioned above were used for the preparation of sensors in Buffer A for cocaine and adenosine, respectively; while for interferon-γ (IFN-γ) and $UO_2^{2+}$, Thiol-DNA conjugated invertase was used. For IFN-γ sensor, the Thiol-DNA conjugated invertase was buffer-exchanged to Buffer C using Amicon-100K twice. For $UO_2^{2+}$ sensor, to avoid the strong interaction between $UO_2^{2+}$ and phosphate anions, the Thiol-DNA conjugated invertase was buffer-exchanged to Buffer D by Amicon-100K for 3 times.

A portion of 1 mL streptavidin-coated magnetic beads (MBs) solution was placed close to a magnetic rack for 1 minute. The clear solution was discarded at replaced by 1 mL of Buffer A, C or D (Buffer A, C and D were used for cocaine/adenosine aptamer, IFN-γ aptamer and $UO_2^{2+}$ DNAzyme sensors, respectively). This buffer exchange procedure was repeated twice. Then, 12 μL 0.5 mM Biotin-DNA in Millipore water was added to the MBs solution and well mixed for 0.5 hour at room temperature. After that, the MBs were washed 2 times using buffer to remove excess Biotin-DNA. Later, 12 μL 0.5 mM functional DNA (Coc-Apt, Ade-Apt, or mixture of equal amount of 39S and 39E) in Millipore water was added to the MBs solution and well mixed for 0.5 hour at room temperature. After 3 times washing using buffer to remove excess DNA, DNA-invertase conjugated (concentrated to 20 μL using Amicon-100K) was added to the solution and well mixed at room temperature for 0.5 hour. Excess DNA-invertase conjugate was washed off by buffer for 3 times and can be recycled by condensing the washing solutions using Amicon-100K. The DNA-invertase conjugate-immobilized MBs were then dispersed in 1 mL Buffer A or C, and the MBs contained in each 40 μL of this solution after removal of buffer was used for the detection of one sample. The preparation can be easily scaled up using the materials of the same mass ratio. For detections of 20% human serum samples (serum diluted using buffer), the MBs were washed twice using 20% human serum before use.

Procedures for Cocaine, Adenosine and $UO_2^{2+}$ Detection Using Commercially Available Personal Glucose Meter For detection using aptamer sensors, 40 μL Buffer A (for cocaine and adenosine sensors) or C (for IFN-γ sensor) containing proper amount of analyte was added to DNA-invertase conjugate-immobilized MBs prepared as above and well mixed for 25 minutes. After that, the solution was separated using a magnetic rack, and 20 μL of the supernatant was transferred into 20 μL 1 M sucrose in Buffer A. After standing at room temperature for 30 minutes (for cocaine and adenosine sensors) or 2 hours (for IFN-γ sensor), 5 μL of the solution was measured using a commercially available personal glucose meter. For cocaine detection in 20% human serum, the reaction time was increased from 30 minutes to 1 hour. For IFN-γ detection in 20% human serum, the time is kept as 2 hours.

For $UO_2^{2+}$ detection, 40 μL Buffer D containing proper amount of $UO_2^{2+}$ was added to DNA-invertase conjugate-immobilized MBs prepared as above and well mixed for 30 minutes. After that, the solution was separated using a magnetic rack. About 0.1 μL 3 M NaOH was added to 20 μL of the supernatant to adjust the pH to 7 (This is important because glucose meter can only detect a solution of pH close to 7). The transferred supernatant was then mixed with 20 μL 1 M sucrose in Buffer A with 2 mM EDTA. After standing at room temperature for 1.5 hours, 5 μL of the solution was measured using a commercially available personal glucose meter.

Figure 7:
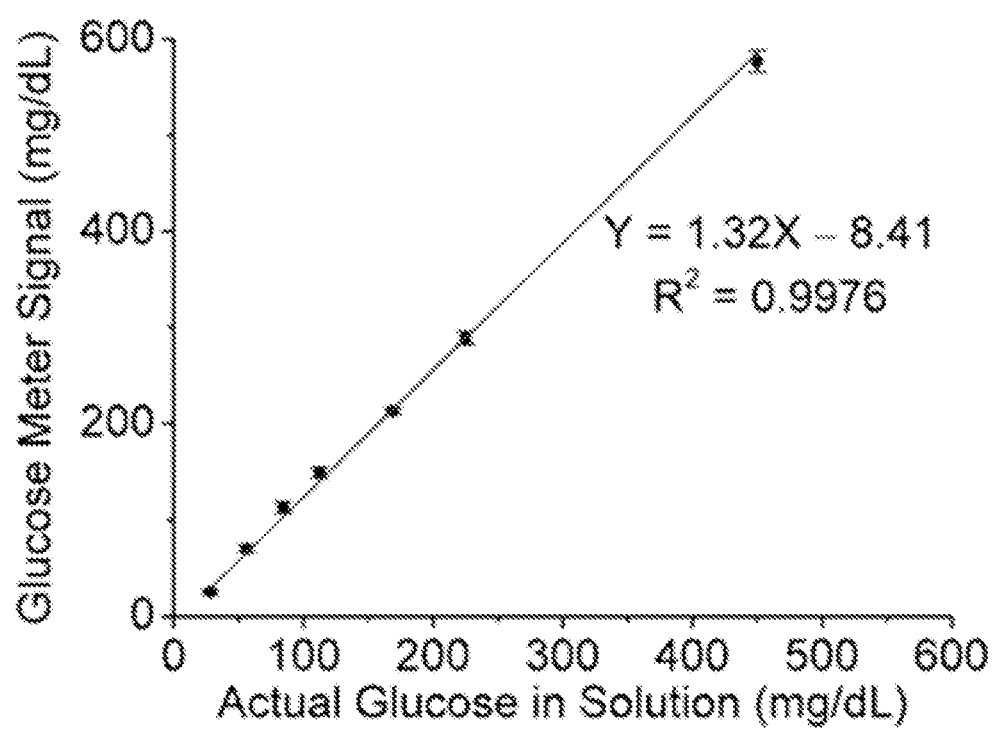
FIG. 7 is a graph showing the correlation between actual glucose concentration in solution and that detected by glucose meter.

Correlation Between Actual Glucose Concentration in Solution and Signal Detected by a PGM The glucose concentration read out in a PGM may not be the actual glucose concentration in the solution. To address this issue, a control experiment was carried out by measuring samples with different amounts of glucose in Buffer A using a PGM. The signal obtained in the PGM correlated well with the actual glucose concentration in the buffer, showing a linear response that is about 32% higher than the actual value in the range of 20~480 mg/dL (FIG. 7).

EXAMPLE 2

Conjugation of Invertase with ssDNA

This example describes methods of conjugating invertase to single-stranded (ss) DNA. One skilled in the art will appreciate that other enzymes that can catalyze the conversion of a substance into glucose, such as cellulose which converts cellulose into glucose, can be used in place of invertase.

Invertase (from baker's yeast), also named as β-fructofuranosidase, is an enzyme that can catalyze the hydrolysis of sucrose.[50] It was used for signal amplification because nanomolar levels of this enzyme are able to efficiently convert as high as millimolar level of sucrose into fructose and glucose within a reasonable time scale at room temperature and requires no laboratory-based devices. In addition, only the produced fructose and glucose are detectable using the widely available personal glucose meter (PGM), while sucrose is completely "silent" in a PGM and does not produce any signal or interference because of its non-reductive character. Therefore, invertase can be used for signal amplification in the design of sensors that can display a "turn-on" response (e.g., in response to the presence of a target agent) in a PGM.

To control the release of invertase upon the interaction between functional DNAs and their target, the enzyme was conjugated with DNA. Although invertase has been widely used as an industrial enzyme and developed as reusable catalysts by chemical immobilization on solid supports, there is are few reports on conjugating this enzyme with other functional molecules, such as DNA.[51-53] Because the active site of invertase is composed of aspartate and glutamate,[54,55] the reactive amine groups of invertase were chosen as the reaction sites for conjugation to preserve the catalytic activity of the enzyme after reaction. Sulfosuccinimidyl-4-(N-maleimidomethyl)cyclohexane-1-carboxylate (sulfo-SMCC) and 1,4-phenylene diisothiocyanate (PDITC) were used to conjugate thiol- and amine-modified DNAs with invertase under mild conditions, respectively.[56]

As illustrated in FIGS. 8A and 8B, in the heterobifuntional linker (sulfo-SMCC) method, invertase was activated by Sulfo-SMCC through the reaction between amine and NHS ester, and then covalently conjugated with thiol-modified DNA via thiol-maleimide reaction; while in the homobifunctional linker method, amine-modified DNA was activated by PDITC and then reacted with the reactive amine groups of invertase. In the presence of excess DNA, both methods yielded sufficient amount of DNA-invertase conjugate according to PAGE (see FIG. 6). The exact yield was not calculated because the number of DNA conjugated on each protein is hard to control during the conjugation reaction. After removal of un-conjugated free DNA, the resulting products containing DNA-invertase conjugate and free invertase can be directly used for sensor preparation, during which the free invertase will be washed off and has no effect on the performance of the sensors.

EXAMPLE 3

Immobilization of Functional DNAs and DNA-Invertase Conjugate to Magnetic Beads This example describes methods of immobilizing the invertase-ssDNA molecules generated in Example 2 to magnetic beads. One skilled in the art will appreciate that other supports can be used in place of the magnetic beads, such as a membrane, glass substrate, or other type of bead, such as a gold bead, and methods of immobilizing to such surfaces is well known in the art.

Magnetic beads (MBs) have been widely used in many biological applications such as isolation, preconcentration, and assays.[57,58] Such beads are easy to use and can be removed from a sample using a magnetic rack, without the need for centrifugation, precipitation, or filtration procedures. For sensors that can be used on-site and household with no laboratory-based devices, MBs can be used.

Streptavidin-coated MBs were employed because they are highly efficient for the immobilization of biotin-modified DNA.[59,60] The binding strength between streptavidin and biotin is as high as $K_d=10^{-15}$ $M^{-1}$, so that the immobilized DNA can survive the mild conditions for sensing applications and minimize nonspecific release.

The immobilization of functional DNAs and DNA-invertase conjugates on streptavidin-coated MBs via DNA hybridization are shown in FIG. 5 and FIGS. 9A-9D. First, a biotin-modified single strand DNA (Biotin-DNA) was immobilized via streptavidin-biotin interaction. This Biotin-DNA could then capture aptamers or the DNAzyme-substrate duplex onto the surface. Finally, DNA-invertase conjugate was hybridized to the functional DNAs on MBs.

Upon the addition of specific targets, the DNA-invertase conjugate is released because of the interactions between functional DNAs and their targets. After removal of MBs, the released DNA-invertase conjugate in solution efficiently catalyzes the conversion of subsequently added sucrose into fructose and glucose, amplifying the signal to the level detectable by a PGM. The presence of the Biotin-DNA improves the sensor design as it has been observed that the performance of the sensors in FIGS. 9A-9D were much better than those using biotin-modified functional DNAs without the linker Biotin-DNA for immobilization. The space provided by the hybridized Biotin-DNA may facilitate the functional DNAs to "stand up" and better preserve their activity on MBs.

EXAMPLE 4

Performance of Functional DNA Sensors Monitored by Personal Glucose Meter (PGM)

This example describes methods used to detect various target agents with the sensors described in Example 3. One skilled in the art will appreciate that similar methods can be used with other sensors to detect other target agents.

As shown in FIG. 5, the analyte-induced release of DNA-invertase conjugate by functional DNAs is a general platform for the development of both aptamer and DNAzyme sensors that can quantitatively detect specific targets using a PGM. Here, we applied this methodology to cocaine aptamer,[13,32,43] adenosine aptamer,[13,38,46,61] interferon-γ (IFN-γ) aptamer,[62-64] and $UO_2^{2+}$-dependent DNAzyme,[49,65,66] to detect the corresponding analytes, respectively.

(1) Cocaine Aptamer-Based Sensor

Figure 9A:
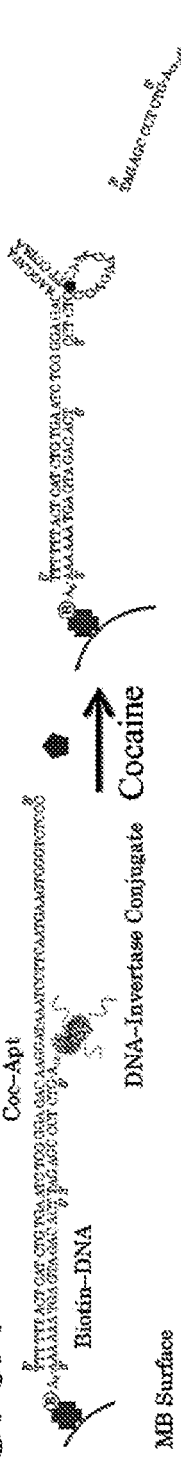
FIGS. 9A-9D are schematic drawings showing the immobilization of DNA-invertase conjugates via hybridization with (A) cocaine aptamer (SEQ ID NO: 4), (B) adenosine aptamer (SEQ ID NO: 6), (C) IFN-γ aptamer (SEQ ID NO: 6) and (D) $UO_2^{2+}$ DNAzyme (SEQ ID NO: 11) on streptavidin-coated MBs and subsequent release of DNA-invertase conjugates in the presence of these analytes.
Figure 10B:
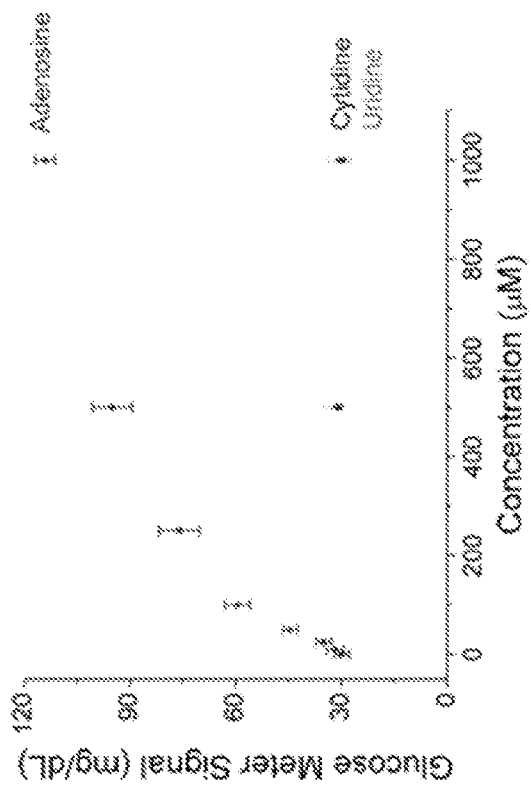
FIGS. 10A-10B are graphs showing performance of (A) cocaine and (B) adenosine sensors in buffer using glucose meter.
Figure 10A:
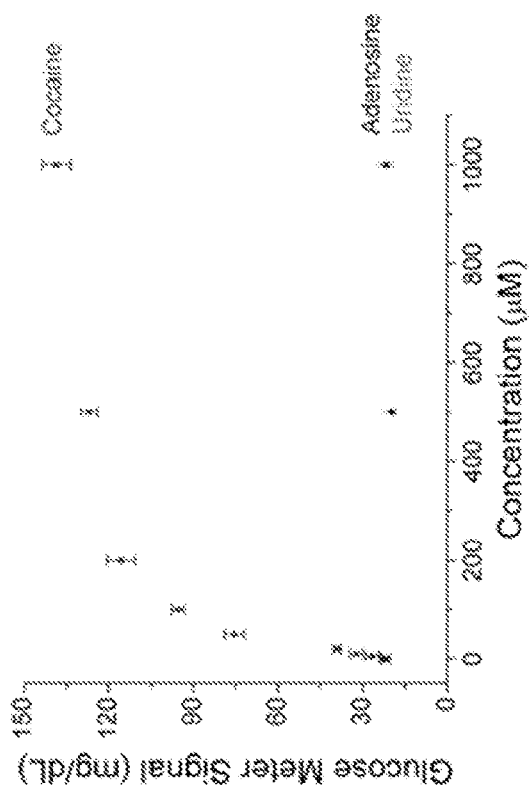

The Biotin-DNA immobilized on MBs via a streptavidin-biotin interaction and the DNA-invertase conjugate obtained through maleimide-thiol reaction were connected by the cocaine DNA aptamer extended with 18 and 12 nucleotides at each end for efficient hybridization, respectively (FIG. 9A). The design allowed a target-specific structure-switching[37,38] of the aptamer in the presence of cocaine and result in the release of DNA-invertase conjugate for signal amplification (FIG. 9A). Upon the addition of 1 mM cocaine and subsequent removal of MBs, the solution yielded 7-fold more glucose from added sucrose by the released DNA-invertase conjugate compared to that in the absence of cocaine, according to the results obtained from a PGM (FIG. 10A). This enhanced catalytic activity was due to the analyte-induced release of DNA-invertase conjugate. Indeed, the final concentration of glucose detected by the PGM was dependent on the concentration of cocaine in the sample, with higher level of glucose produced in the presence of more cocaine until reaching the plateau. The relationship between cocaine concentration and signal displayed in PGM are shown in FIG. 10A. A detection limit as low as 5.3 μM cocaine was achieved based on $3\sigma_b$/slope ($\sigma_b$, standard deviation of the blank samples) from the data in the titration curve, showing the high sensitivity of the sensor. In contrast, other compounds such as adenosine and uridine could not induce the enhancement of glucose production even in the millimolar range, indicating the high selectivity of cocaine aptamer is preserved in the sensor design.

Figure 12:
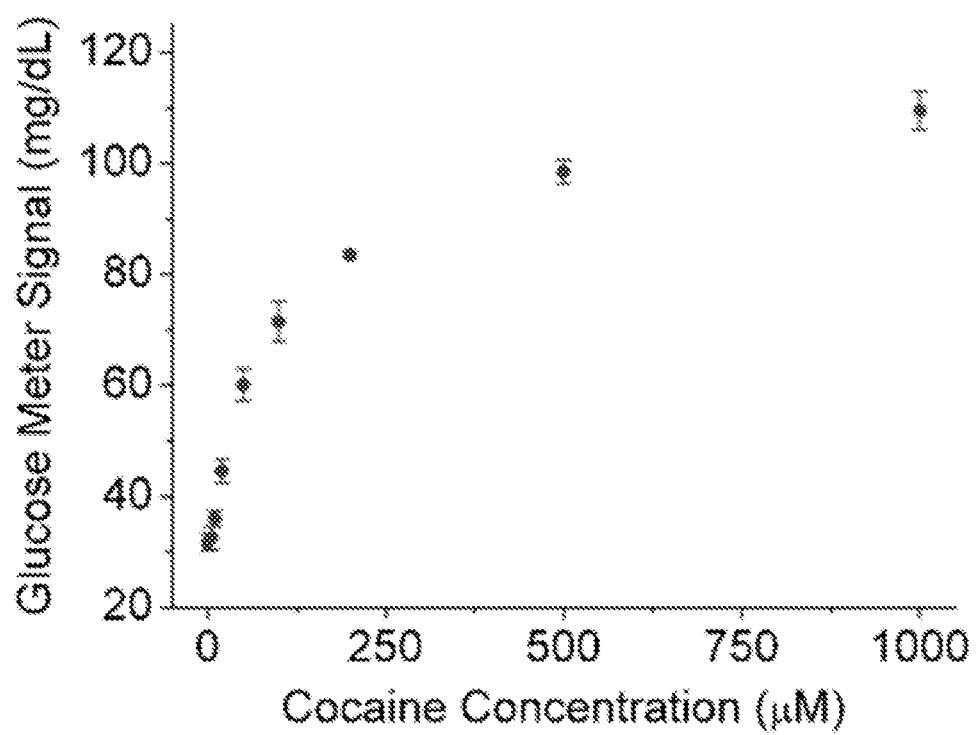
FIG. 12 is a graph showing the performance of the cocaine sensor in 20% human serum samples using glucose meter.

To confirm the role of the cocaine aptamer in the performance of the sensor, control experiments using aptamer-trunked DNA as linker rather than cocaine aptamer without truncation were carried out and showed no enhancement of glucose production even in the presence of 1 mM cocaine, while 7-fold enhancement was observed in the case of normal cocaine aptamer (FIG. 11). In addition, to test the immunity of complex sample matrix, the sensor was also applied to detect cocaine in 20% human serum. As shown in FIG. 12, the concentration of glucose detected by a PGM corresponded well with that of cocaine in the serum samples. A detection limit of 10 μM was achieved.

It is noted that the whole quantitative assay can be accomplished within 1.5 hour and requires only a widely available PMG without any other instrumentation. Thus, the sensor is suitable for on-site and household quantitative applications.

(2) Adenosine Aptamer-Based Sensor

Figure 9B:
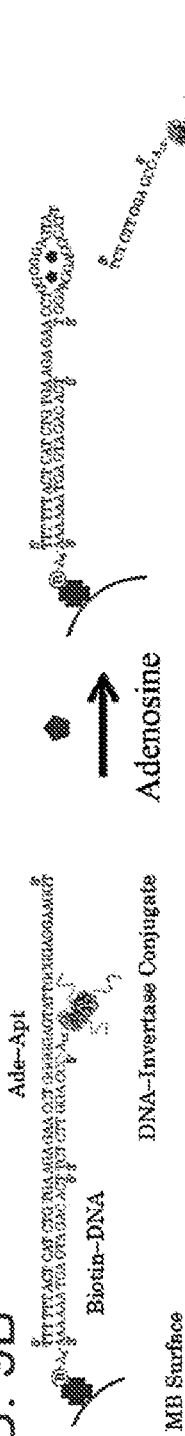

By a similar design as cocaine aptamer-based sensor above, an adenosine aptamer was used as the linker between the immobilized Biotin-DNA and DNA-invertase conjugate for the design of adenosine sensor (FIG. 9B). Unlike in the cocaine sensor, here the DNA-invertase conjugate was synthesized via the reaction of an amine-reactive homobifunctional linker, PDITC, with both reactive amine groups on invertase and DNA. The use of a different conjugation method demonstrates the compatibility of other conjugation methods in the sensor design.

In the presence of 1 mM adenosine, the resulting solution after removal of MBs exhibited 3-fold enhancement on enzymatic activity in converting sucrose into glucose as measured by a PGM (FIG. 10B), likely through the structure-switching[37,38] mechanism of aptamer that released DNA-invertase conjugate from MBs to solution (FIG. 9B). The titration curve using samples containing increasing amounts of adenosine (0~1 mM) showed a correspondingly growing concentration of glucose detected by a PGM (FIG. 10B). The detection limit of the sensor was estimated to be 20 μM adenosine by the definition of $3\sigma_b$/slope. The selectivity of this sensor to adenosine is very high, as other nucleotides such as uridine and cytidine did not show any effect on the production of glucose. Guanosine was not investigated due to the solubility issue on preparing stock solutions. The presence of adenosine aptamer was found to have an essential role in the performance of the sensor because no response over blank was observed in PGM if the underlined part of the aptamer was removed (FIG. 11).

Similar to the cocaine sensor, this sensor could quantitatively detect the concentration of adenosine in solution within 1 hour by using only a PGM. Thus it can serve as an efficient sensor for on-site and household analysis.

(3) Interferon-Gamma (IFN-γ) Aptamer-Based Sensor

Figure 9C:
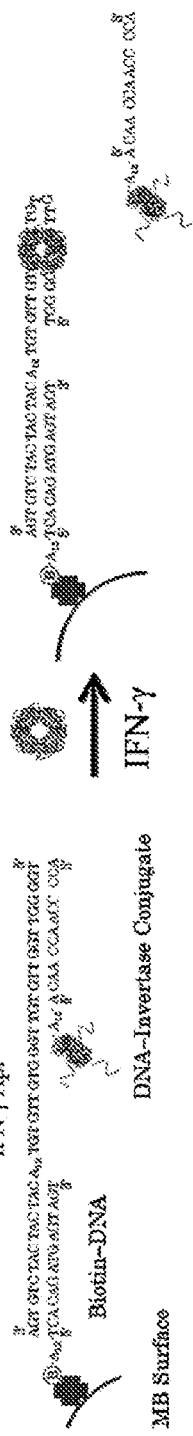
Figure 13A:
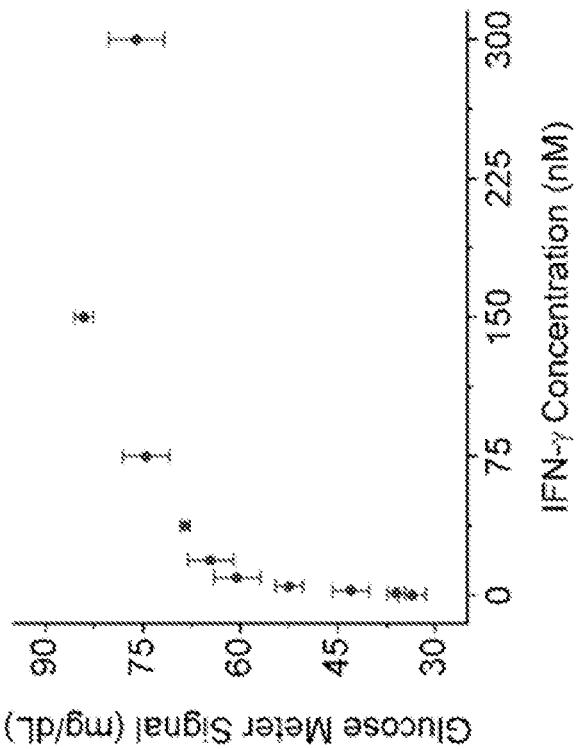
FIGS. 13A and 13B are graphs showing the performance of the IFN-γ sensor in (A) buffer and (B) 20% human serum using glucose meter.

In addition to small organic molecules such as adenosine and cocaine, the large protein molecule IFN-γ was investigated as the target of the aptamer-based sensor design described herein. The design is similar to the aptamer-based sensors shown above, but with an additional $A_{12}$ linker between the Biotin-DNA and the IFN-γ binding part of the aptamer, to minimize the interference of Biotin-DNA to the binding between large IFN-γ molecule and the aptamer (FIG. 9C). In buffer solution, the sensor also showed an increasing glucose produced by the released DNA-invertase conjugate in the presence of increasing amount of IFN-γ (FIG. 13A). About a 3-fold enhancement of signal in a PGM over blank was observed in the presence of 200 nM IFN-γ. As low as 2.8 nM IFN-γ could be detected. This sensitivity is similar to the binding affinity of the aptamer,[62-64] suggesting the design has well preserved the activity of the aptamer.

Figure 13B:
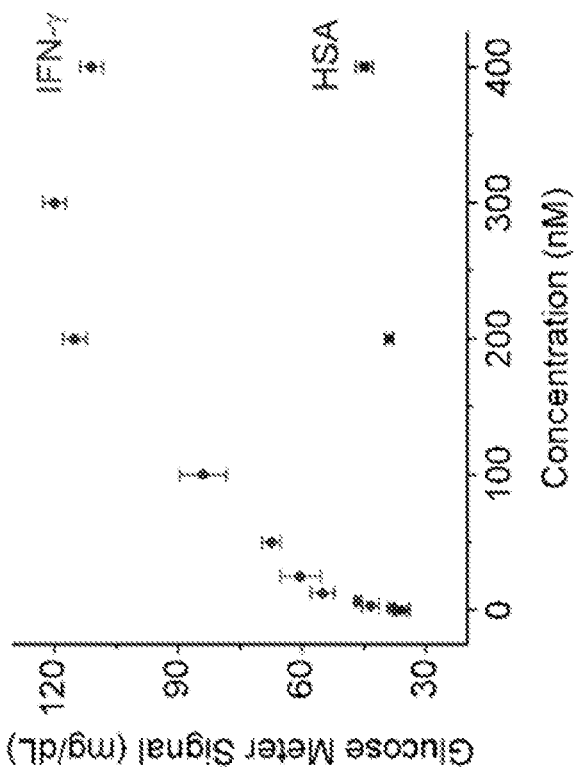

In contrast, HSA, a non-target protein of the aptamer, showed negligible on the concentration of glucose detected by a PGM. Further, the detection of IFN-γ in 20% human serum by the sensor was also investigated to show the performance of the sensor in the complex sample matrix with numerous serum proteins (FIG. 13B). The signal in a PGM reached plateau at a lower concentration of IFN-γ in 20% serum compared to that obtained in buffer. This may be due to the easier release of DNA-invertase conjugate upon IFN-γ binding because the DNA hybridization may be weaker in diluted serum solution. Nevertheless, the detection limit is similar, as 3.2 nM IFN-γ according to the definition of $3\sigma_b$/slope.

Because of the important role of IFN-γ in human immunity and the diagnosis of relevant diseases such as tuberculosis, the sensor design in this work using only a PGM without any other instrumentation can find applications in point-of-care or household quantification of IFN-γ as disease marker.

(4) $UO_2^{2+}$-Dependent DNAzyme-Based Sensor

Figure 9D:
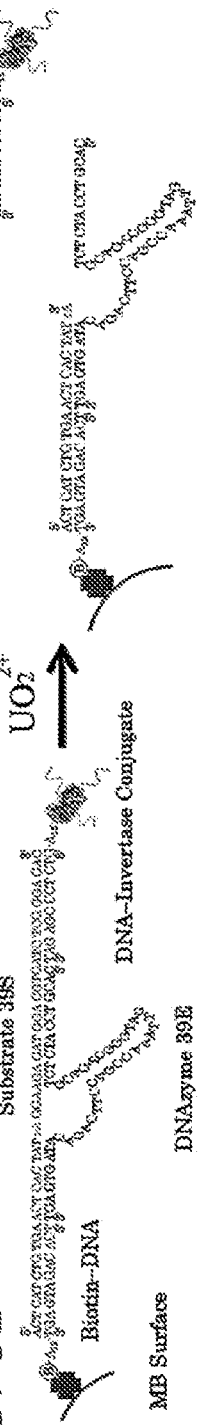
Figure 14B:
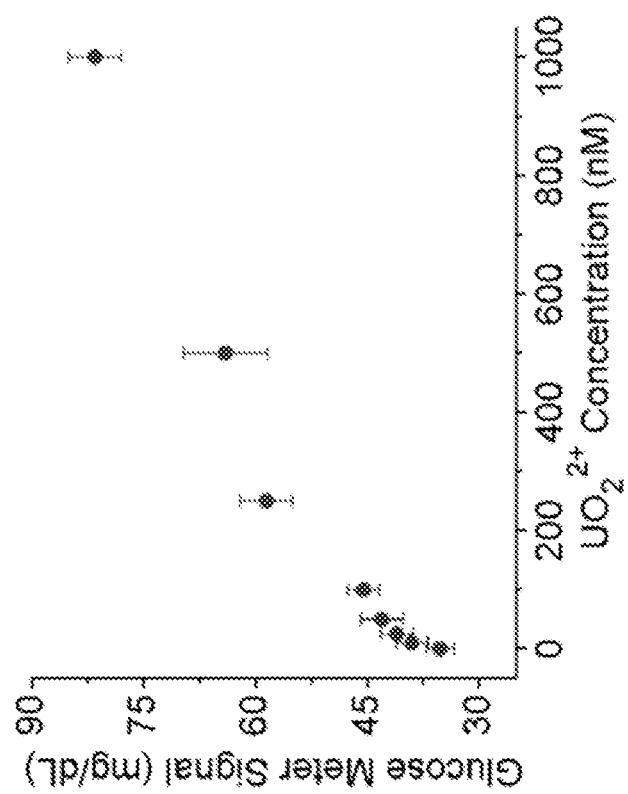
FIGS. 14A and 14B are graphs showing the performance of the $UO_2^{2+}$ sensor using glucose meter (A) and its selectivity (B). Selectivity: 1: 50 nM $UO_2^{2+}$; 2: 1 μM $UO_2^{2+}$; 3: 1 μM $Pb^{2+}$; 4: 1 μM $Cd^{2+}$; 5: 100 μM $Ca^{2+}/Mg^{2+}$; 6: 1 μM $Zn^{2+}/Cu^{2+}$; 7: 1 μM $Co^{2+}/Ni^{2+}$; 8: 1 μM $VO^+$; 9: 1 μM $Th^{4+}$. The signal in glucose meter is shown as mg/dL.
Figure 14A:
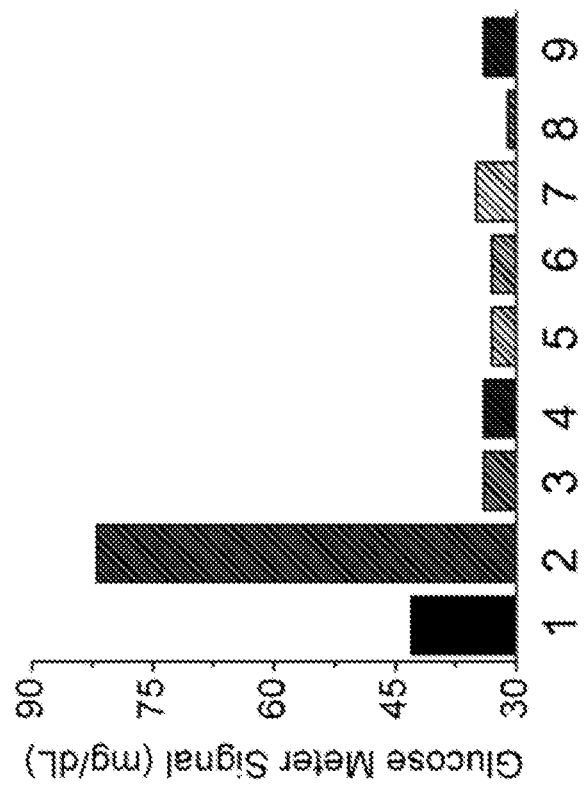

Different from the sensor designs based on aptamers described above, to ensure efficient release of DNA-invertase conjugate from MBs for a DNAzyme-based sensor, the Biotin-DNA immobilized on MBs and the DNA-invertase conjugate were connected by the substrate (39S) of $UO_2^{2+}$-dependent DNAzyme (39E) via 12 base pair hybridization, respectively (FIG. 9D). Further addition of 39E to hybridize with 39S could not cause the cleavage of 39S and subsequent release of DNA-invertase conjugate unless $UO_2^{2+}$ was present.[49,65,66] As expected, upon the addition of $UO_2^{2+}$ up to 1 μM, the resulting solution after magnetic removal of MBs were nearly 2-fold more active in catalyzing glucose production than blank without $UO_2^{2+}$. With increasing amount of $UO_2^{2+}$ (0~1 μM) in the samples, more glucose was detected by a PGM correspondingly (FIG. 14A). A detection limit of 9.8 nM $UO_2^{2+}$ was obtained based on the definition of $3\sigma_b$/slope.

Here, a relatively longer response time was needed for the $UO_2^{2+}$ (2 hours) sensor than the aptamer-based sensors (within 1 hour) possibly because the release of DNA-invertase conjugate was less efficient. This may be the result of either the binding of $UO_2^{2+}$ to streptavidin or the reduced activity of DNAzyme immobilized on MBs. Nevertheless, the sensor still exhibited good selectivity to $UO_2^{2+}$ over other related metal ions (FIG. 14B), suggesting the specificity of the original DNAzyme 39E was preserved in the sensor design. These results revealed that, in addition to aptamers, the design could also be applied to DNAzyme-based sensors and achieve portable, low cost and quantitative detection of metal ions using only a PGM for potential on-site and household applications.

EXAMPLE 5

Detection of DNA by Personal Glucose Meter (PGM)

This example describes the generation and testing of a sensor that includes functional DNA to detect target hepatitis B virus DNA as generally illustrated in FIG. 4B. One skilled in the art will appreciate that similar methods can be used to generate other functional DNA-based sensors to detect other target nucleic acids.

Streptavidin-coated magnetic beads (MB, 1 μm in diameter) and Amicon centrifugal filters were purchased from Bangs Laboratories Inc. (Fishers, Ind.) and Millipore Inc. (Billerica, Mass.), respectively. Grade VII invertase from baker's yeast (*S. cerevisiae*), sulfosuccinimidyl-4-(N-maleimidomethyl)cyclohexane-1-carboxylate (sulfo-SMCC), Tris(2-carboxyethyl)phosphine hydrochloride (TCEP), bovine serum albumin (BSA) and other chemicals for buffers and solvents were from Sigma-Aldrich, Inc. (St. Louis, Mo.). The following oligonucleotides were obtained from Integrated DNA Technologies, Inc. (Coralville, Iowa):

```
Biotin-DNA:
                                         (SEQ ID NO: 1)
5'-TCACAGATGAGTAAAAAAAAAAAA-Biotin-3'

Thiol-DNA:
                                         (SEQ ID NO: 2)
5'-HS-AAAAAAAAAAAAGTCTCCCGAGAT-3'

Target DNA:
                                         (SEQ ID NO: 13)
5'-ACTCATCTGTGAATCTCGGGAGACTTTTTT-3'

Target DNA G mismatch:
                                         (SEQ ID NO: 14)
ACTCATGTGTGAATCTCGGGAGACTTTTTT Target DNA A mismatch:
                                         (SEQ ID NO: 15)
ACTCATATGTGAATCTCGGGAGACTTTTTT Target DNA T mismatch:
                                         (SEQ ID NO: 16)
ACTCATTTGTGAATCTCGGGAGACTTTTTT Target DNA 2 mismatch:
                                         (SEQ ID NO: 17)
ACTCAAGTGTGAATCTCGGGAGACTTTTTT Biotin-DNA for hepatitis B virus (HBV):
                                         (SEQ ID NO: 18)
Biotin-AAAAAAAAAAAAACCTTTAACCTAA Thiol-DNA for HBV:
                                         (SEQ ID NO: 18)
TCCTCCCCCAACTCCTCCCAAAAAAAAAAAA-SH Target DNA for HBV:
                                         (SEQ ID NO: 19)
TGGGAGGAGTGGGGGGAGGAGATTAGGTTAAAGGT Target DNA for HBV A mismatch:
                                         (SEQ ID NO: 20)
TGGGAGGAGTGGGGGGAGGAGATTAGGTAAAAGGT Target DNA for HBV G mismatch:
                                         (SEQ ID NO: 21)
TGGGAGGAGTGGGGGGAGGAGATTAGGTGAAAGGT'

Target DNA for HBV C mismatch:
                                         (SEQ ID NO: 22)
TGGGAGGAGTGGGGGGAGGAGATTAGGTCAAAGGT
```

Buffers used:
Buffer A: 0.1 M NaCl, 0.1 M sodium phosphate buffer, pH 7.3, 0.05% Tween-20
Buffer B: 0.25 M NaCl, 0.15 M sodium phosphate buffer, pH 7.3, 0.05% Tween-20

DNA-Invertase Conjugation

To 30 μL of 1 mM Thiol-DNA or Thiol-DNA for HBV in Millipore water, 2 μL of 1 M sodium phosphate buffer at pH 5.5 and 2 μL of 30 mM TCEP in Millipore water were added and mixed. This mixture was kept at room temperature for 1 hour and then purified by Amicon-10K using Buffer A without Tween-20 by 8 times. For invertase conjugation, 400 μL of 20 mg/mL invertase in Buffer A without Tween-20 was mixed with 1 mg of sulfo-SMCC. After vortexing for 5 minutes, the solution was placed on a shaker for 1 hour at room temperature. The mixture was then centrifuged and the insoluble excess sulfo-SMCC was removed. The clear solution was then purified by Amicon-100K using Buffer A without Tween-20 by 8 times. The purified solution of sulfo-SMCC-activated invertase was mixed with the above solution of thiol-DNA. The resulting solution was kept at room temperature for 48 hours. To remove unreacted thiol-DNA, the solution was purified by Amicon-100K for 8 times using Buffer A without Tween-20.

DNA Detection Using PGM

A portion of 2 mL 1 mg/mL streptavidin-coated MBs were buffer exchanged to Buffer A twice, and then dispersed in 2 mL Buffer A. Biotin-DNA was added to the solution to achieve a final concentration of 5 μM and the mixture was well mixed for 30 min at room temperature. After that, the MBs were separated from the mixture by a magnetic rack. The MBs were further washed by Buffer A for 3 times and then separated from each portion of the 50 μL 1 mg/mL MBs in Buffer A. To each of the MBs residues, 100 μL DNA sample of various concentration of DNA in Buffer A was added and the mixture was well mixed for 2 hours at room temperature. After washing the MBs residue by 3 times using Buffer A containing 2 mg/mL BSA to remove unbound DNA and block non-specific binding sites by BSA, 100 μL 5 mg/mL DNA-invertase conjugate in Buffer A was added and the mixture was well mixed for 30 min at room temperature. After washing the MBs residue by 5 times using Buffer A, 100 μL 0.5 M sucrose in Buffer A was added to the MBs residue and then well mixed for 16 h at room temperature. A portion of 5 μL of the final solution was tested by a glucose meter.

HBV DNA Fragment Detection Using PGM

A portion of 2 mL 1 mg/mL streptavidin-coated MBs were buffer exchanged to Buffer B twice, and then dispersed in 2 mL Buffer B. Biotin-DNA for HBV was added to the solution to achieve a final concentration of 5 μM and the mixture was well mixed for 30 min at room temperature. After that, the MBs were separated from the mixture by a magnetic rack. The MBs were further washed by Buffer B for 3 times and then separated from each portion of the 50 μL 1 mg/mL MBs in Buffer B. To each of the MBs residues, 100 μL DNA sample of various concentration of DNA in Buffer B was added and the mixture was well mixed for 1 hour at room temperature. After washing the MBs residue by 3 times using Buffer B containing 2 mg/mL BSA to remove unbound DNA and block non-specific binding sites by BSA, 100 μL 5 mg/mL DNA-invertase conjugate in Buffer B was added and the mixture was well mixed for 30 min at room temperature. After washing the MBs residue by 5 times using Buffer B, 25 μL 1 M sucrose in Buffer B was added to the MBs residue and then well mixed for 3 h at room temperature. A portion of 5 μL of the final solution was tested by a glucose meter.

Principle of the Detection

Figure 15:
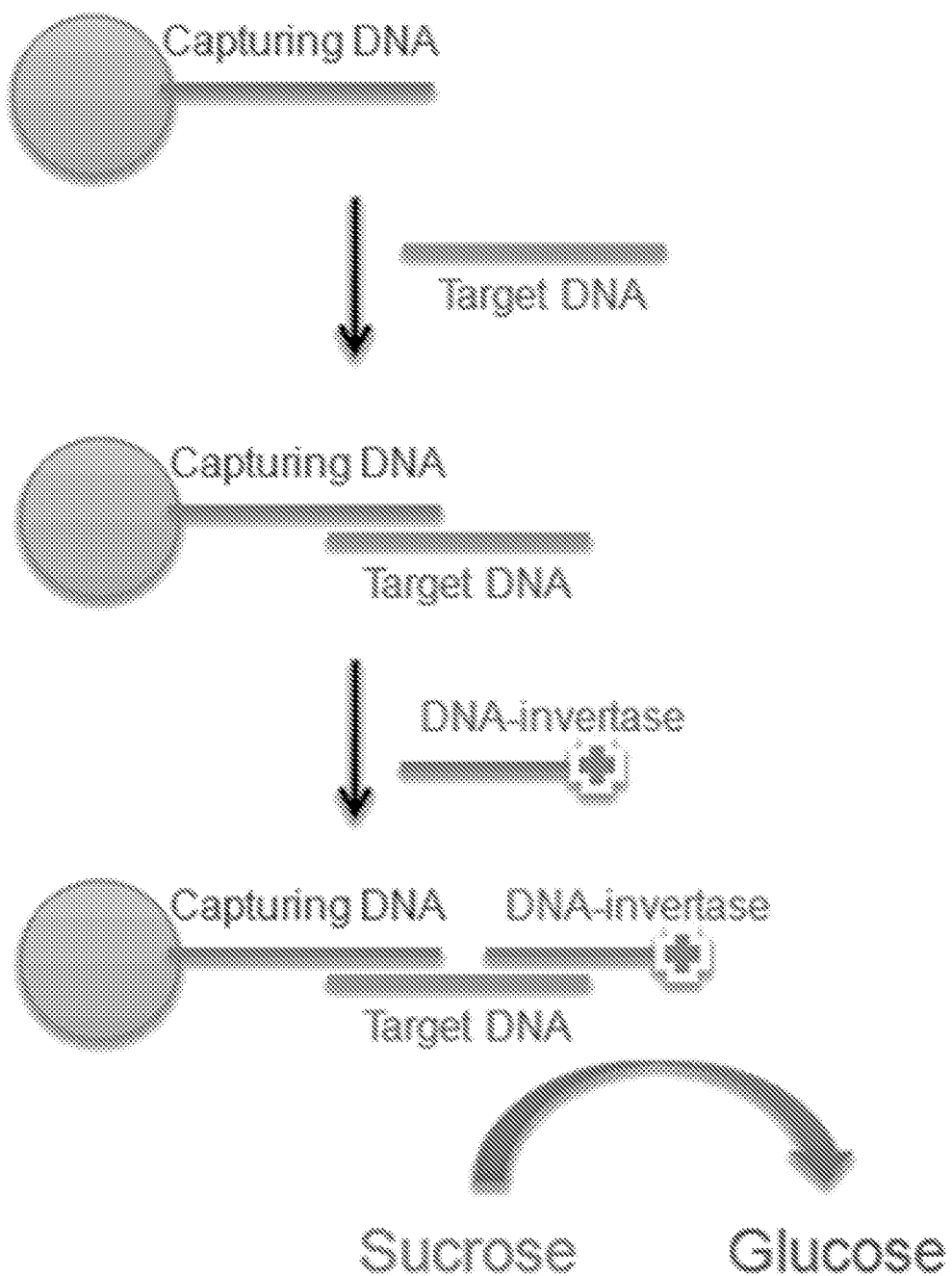
FIG. 15 is a schematic drawing showing the mechanism of target DNA detection by a personal glucose meter (PGM) through the DNA-invertase conjugate approach.

A challenge for DNA detection using a personal glucose meter (PGM) is establishing a link between the DNA concentration in the sample and the glucose concentration detected by the PGM. To overcome this challenge, the DNA-invertase conjugate was utilized as the link (FIG. 15). First, the capturing DNA conjugated to the invertase is capable of recognizing target DNA via DNA hybridization. Second, the invertase enzyme can efficiently catalyze the hydrolysis of sucrose into glucose, which can be detected by the PGM and transform into the concentration of target DNA.

Detection of a 12-mer Target DNA by PGM

Figure 16A:
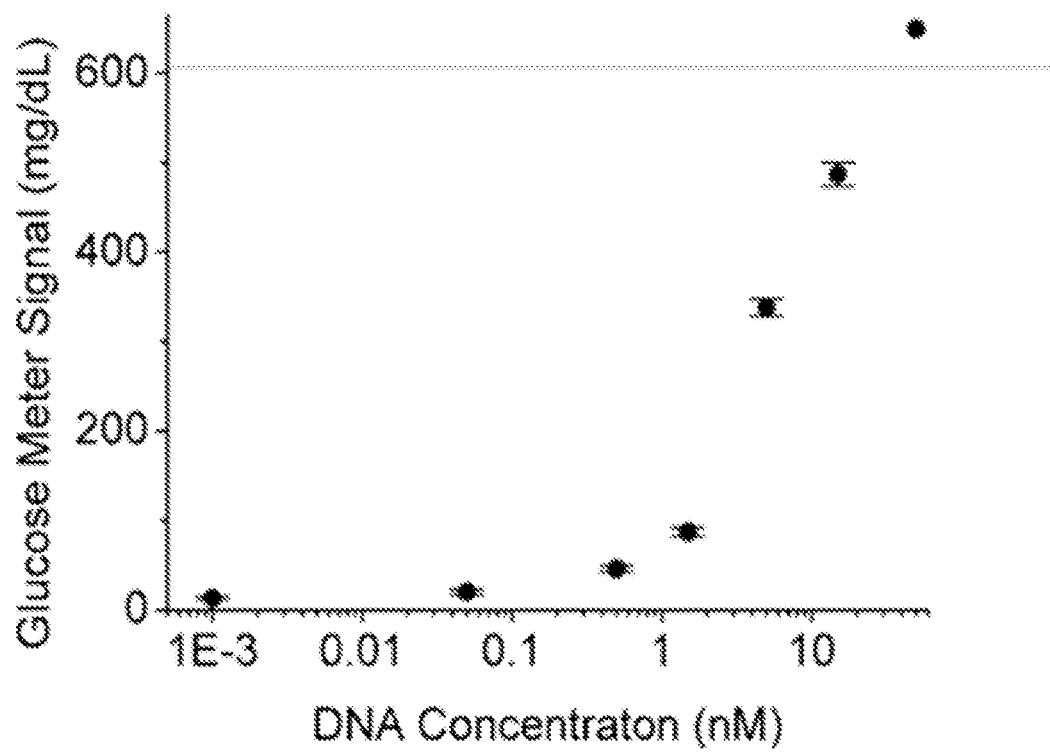
FIG. 16A is a graph showing the detection of target DNA using a PGM. The detection was conducted in 0.1 M sodium phosphate buffer, pH 7.3, 0.1 M NaCl, 0.05% Tween-20. The line in the figure indicates the upper limit of the PGM (600 mg/dL glucose).
Figure 16B:
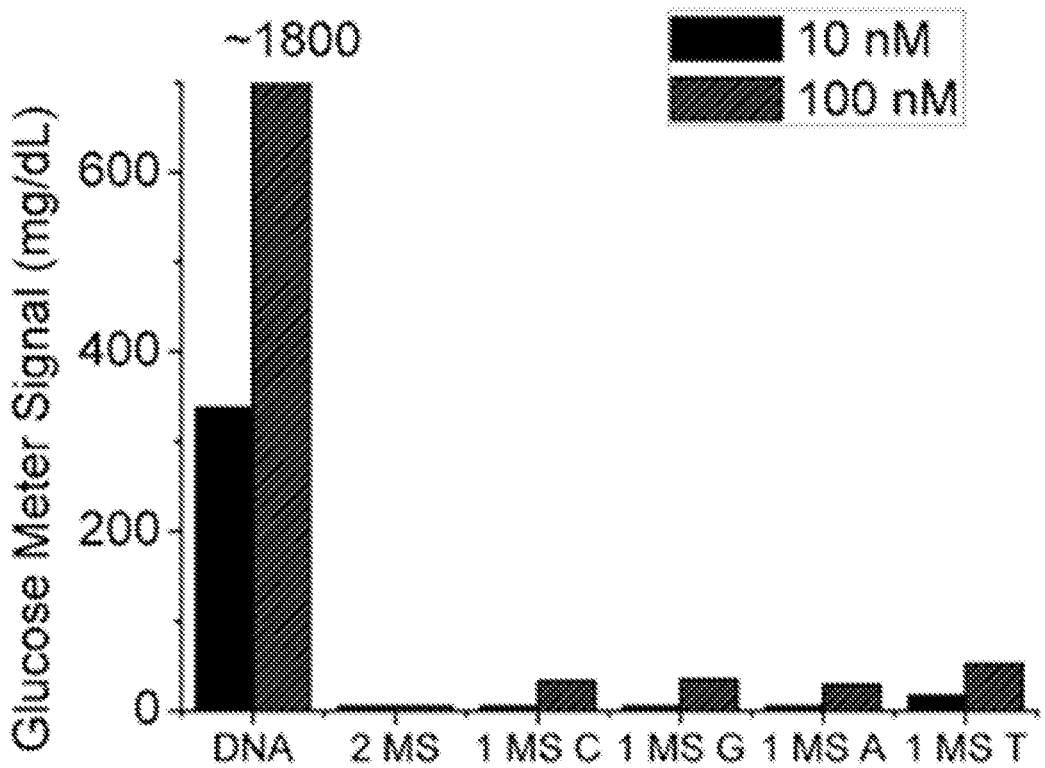
FIG. 16B is a bar graph showing the Single mismatch selectivity of the DNA detection using a PGM. The detection was conducted in 0.1 M sodium phosphate buffer, pH 7.3, 0.1 M NaCl, 0.05% Tween-20.

As shown in FIG. 16, DNA detection using a PGM was achieved through the DNA-invertase conjugate approach. In the presence of low concentration of target DNA, little DNA-invertase conjugate could be bound to the surface of the MBs. Thus only a very low glucose meter signal was detected. However, with increasing amounts of target DNA in the sample, the DNA-invertase conjugate was immobilized to the MBs more efficiently, resulting in a higher amount of glucose production by the enzymatic reaction. More than 40-fold enhancement of glucose production was observed in the presence of 10 nM target DNA. A detection limit of about 50 pm was achieved under these experimental conditions. Due to the large surface area of the MBs, the capacity of DNA binding is large and the dynamic range of the detection was found to be at least between $10^{-12}$~$10^{-8}$ M target DNA.

In addition, the detection showed very good selectivity to the target DNA. As shown in FIG. 17, with either 1 or 2 mismatches in the target DNA under the same condition, the DNA sample produced little glucose signal detected by the PGM. The excellent sequence-specificity is ascribed to the 12-bp DNA hybridization between the target DNA and Biotin-DNA.

Detection of Hepatitis B Virus (HBV) DNA Fragment by PGM

The same approach was used to detect the concentration of the hepatitis B Virus (HBV) DNA fragment in the sample by a PGM. To make the glucose production by the DNA-invertase conjugate faster, longer sequence of DNA hybridization between target DNA and DNA-invertase conjugate (20 bp vs. 12 bp), higher ionic strength of buffer, and more concentrated sucrose and final MBs solutions were used to enhance the affinity of target DNA fragment binding to the surface and the concentration of DNA-invertase conjugate in the final solution. As a result, the response in the PGM could be obtained within 3 hours for the HBV DNA fragment detection here compared to 16 hours for the 12-mer target DNA mentioned above.

Figure 17A:
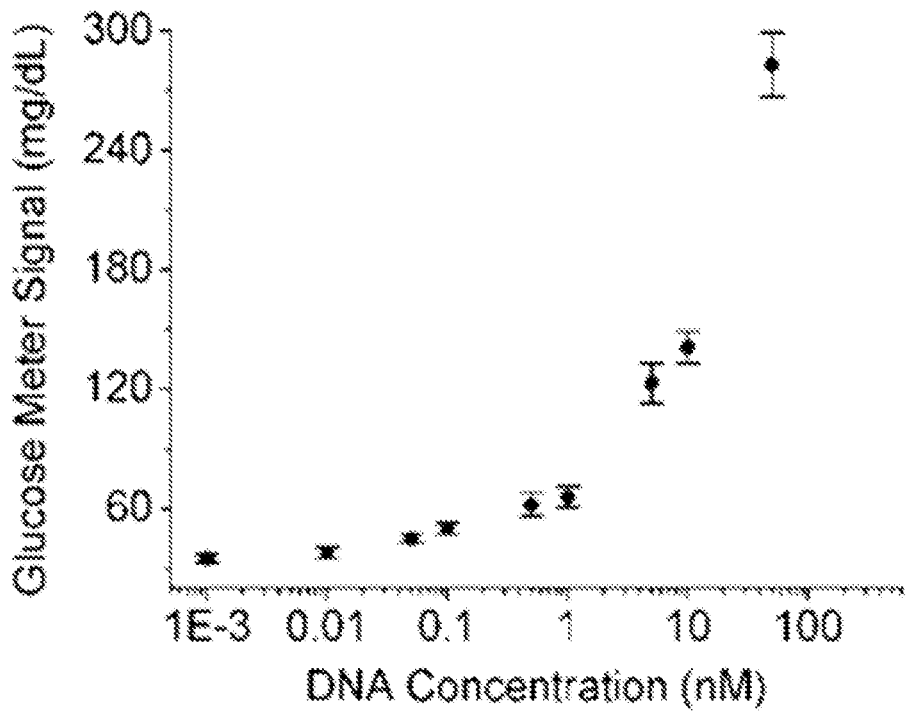
FIGS. 17A and B are graphs showing the detection of an HBV DNA fragment using a PGM. The detection was conducted in 0.15 M sodium phosphate buffer, pH 7.3, 0.25 M NaCl, 0.05% Tween-20. (A) HBV DNA fragment detection; (B) Single mismatch selectivity of the detection.
Figure 17B:
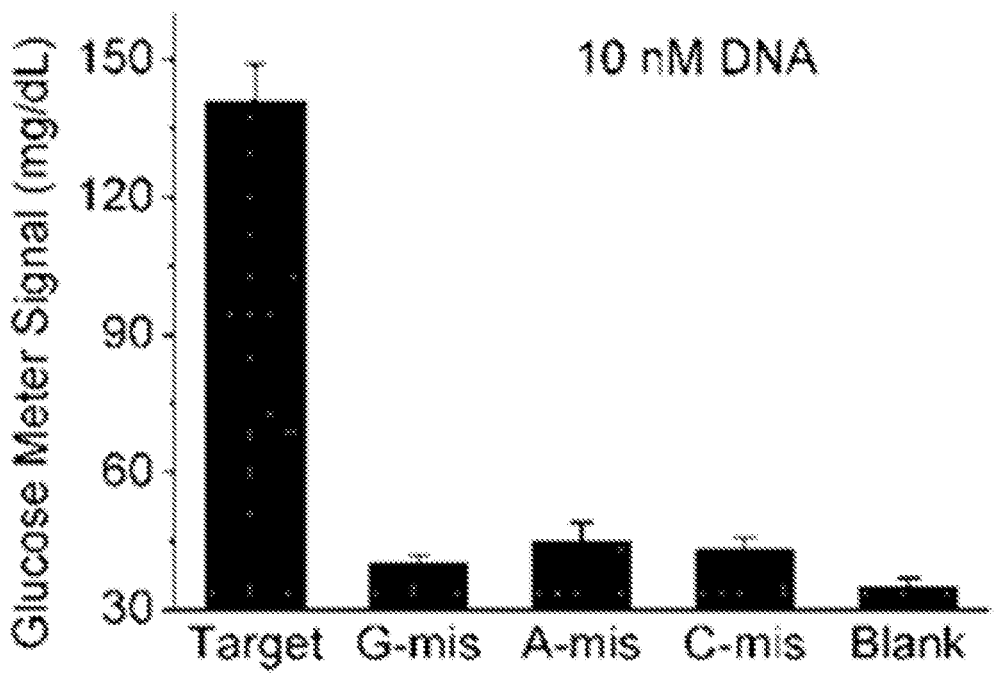

As shown in FIG. 17A, about 30-fold enhancement of glucose production could be achieved in the presence of 50 nM HBV DNA fragment. A detection limit of 40 pm was calculated according to the definition by IUPAC. The detection is also sequence-specific. In the presence of 1 mismatch, the HBV DNA fragment sample could only produce very mild glucose signal detectable by the glucose meter compared to fully-matched one under the same condition (FIG. 17B).

EXAMPLE 6

Detection of Biotin by Personal Glucose Meter (PGM)

This example describes the generation and testing of a sensor that includes antibodies to detect the target biotin as generally illustrated in FIG. 2A. One skilled in the art will appreciate that similar methods can be used to generate other antibody-based sensors to detect other target molecules.

Streptavidin-coated magnetic beads (MB), Amicon centrifugal filters, Grade VII invertase from baker's yeast (*S. cerevisiae*), and other materials were obtained as described in Example 5. The following oligonucleotides were obtained from Integrated DNA Technologies, Inc. (Coralville, Iowa):

```
                                         (SEQ ID NO: 23)
    Amine-DNA:  5'-NH2-AGAGAACCTGGGTTTTTT-3'

(SEQ ID NO: 24)
    Thiol-DNA:  5'-HS-AAAAAAAAAAAACCCAGGTTCTCT-3'
```

Buffer A: 0.1 M NaCl, 0.2 M sodium phosphate buffer, pH 7.3, 0.05% Tween-20
Conjugation Chemistry
(1) DNA-Desthiobiotin Conjugation To 0.4 mL of 0.2 mM Amine-DNA in Buffer A without Tween-20, 5 mg N-Hydroxysuccinimido-DL-desthiobiotin dissolved in 50 μL ethanol was added and the mixture was well mixed at room temperature for 4 hours. Then, the DNA-desthiobiotin conjugate was purified by Amicon-10K for 8 times using Buffer A without Tween-20.

(2) DNA-Invertase Conjugation

To 30 μL of 1 mM Thiol-DNA in Millipore water, 2 μL of 1 M sodium phosphate buffer at pH 5.5 and 2 μL of 30 mM TCEP in Millipore water were added and mixed. This mixture was kept at room temperature for 1 hour and then purified by Amicon-10K using Buffer A without Tween-20 by 8 times. For invertase conjugation, 400 μL of 20 mg/mL invertase in Buffer A without Tween-20 was mixed with 1 mg of sulfo-SMCC. After vortexing for 5 minutes, the solution was placed on a shaker for 1 hour at room temperature. The mixture was then centrifuged and the insoluble excess sulfo-SMCC was removed. The clear solution was then purified by Amicon-100K using Buffer A without Tween-20 by 8 times. The purified solution of sulfo-SMCC-activated invertase was mixed with the above solution of thiol-DNA. The resulting solution was kept at room temperature for 48 hours. To remove unreacted thiol-DNA, the solution was purified by Amicon-100K for 8 times using Buffer A without Tween-20.

Figure 18:
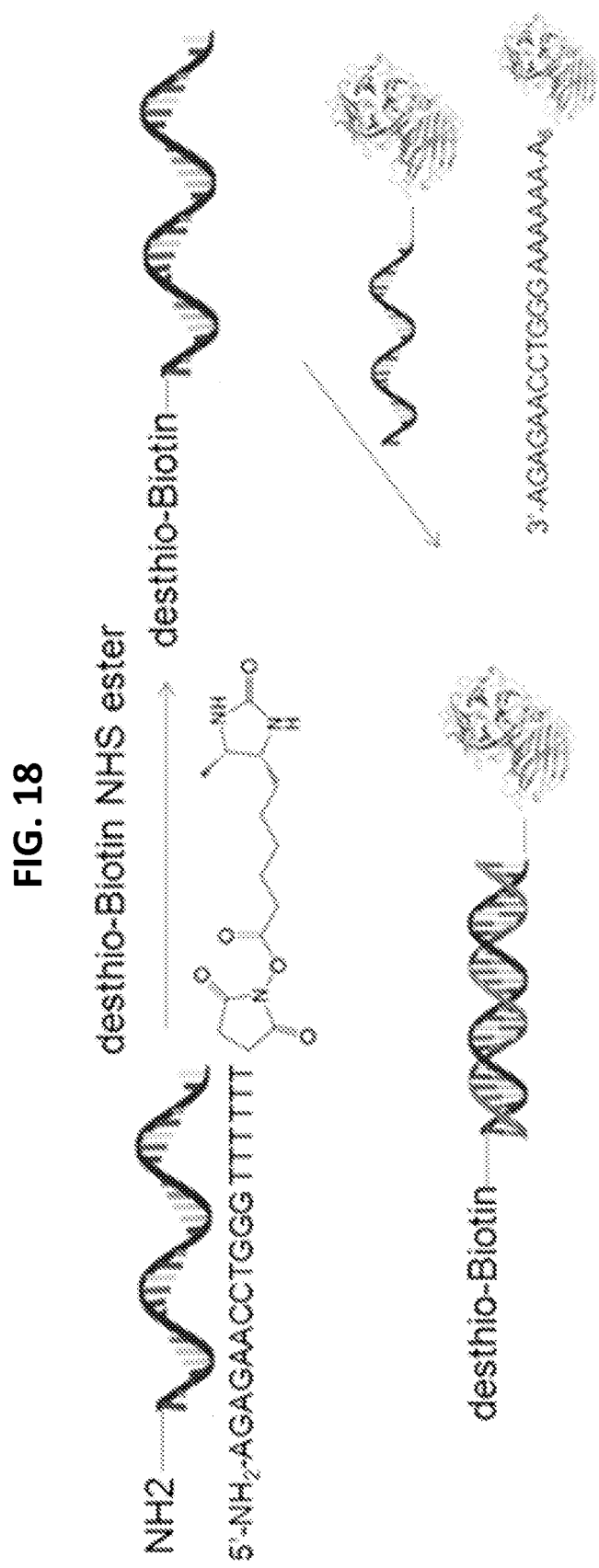
FIG. 18 is a schematic drawing showing desthiobiotin-invertase conjugation through assembly from DNA-desthiobiotin and DNA-invertase conjugations.

(3) Desthiobiotin-Invertase Conjugation:

Desthiobiotin-invertase conjugate was prepared through the assembly from the hybridization of DNA-desthiobiotin and DNA-invertase conjugations in buffer A, as shown in FIG. 18.

Procedure for the Biotin Detection Using a PGM

A portion of 1 mL 1 mg/mL streptavidin-coated MBs were buffer exchanged to Buffer A twice, and then dispersed in 1 mL Buffer A. DNA-desthiobiotin conjugate was added to the solution to achieve a final concentration of 5 μM and the mixture was well mixed for 1 hour at room temperature. After that, the MBs were further washed by Buffer A for 3 times, dispersed in 1 mL 10 mg/mL DNA-invertase, and then well mixed for 30 min at room temperature. The DNA-invertase solution was recycled and the MBs were washed by 5 times using Buffer A and then dispersed in 1 mL Buffer A. The MBs separated from each portion of the 30 μL 1 mg/mL MBs in Buffer A was used for one assay. To each of the MBs residues, 30 μL biotin sample of various concentration of biotin in Buffer A was added and the mixture was well mixed for 15 minutes at room temperature. After removing MBs by a magnetic rack, the solution containing released invertase was mixed with 30 μL 1 M sucrose for 30 min. A portion of 5 μL of the final solution was tested by a glucose meter.

Principle of Detection

Figure 19:
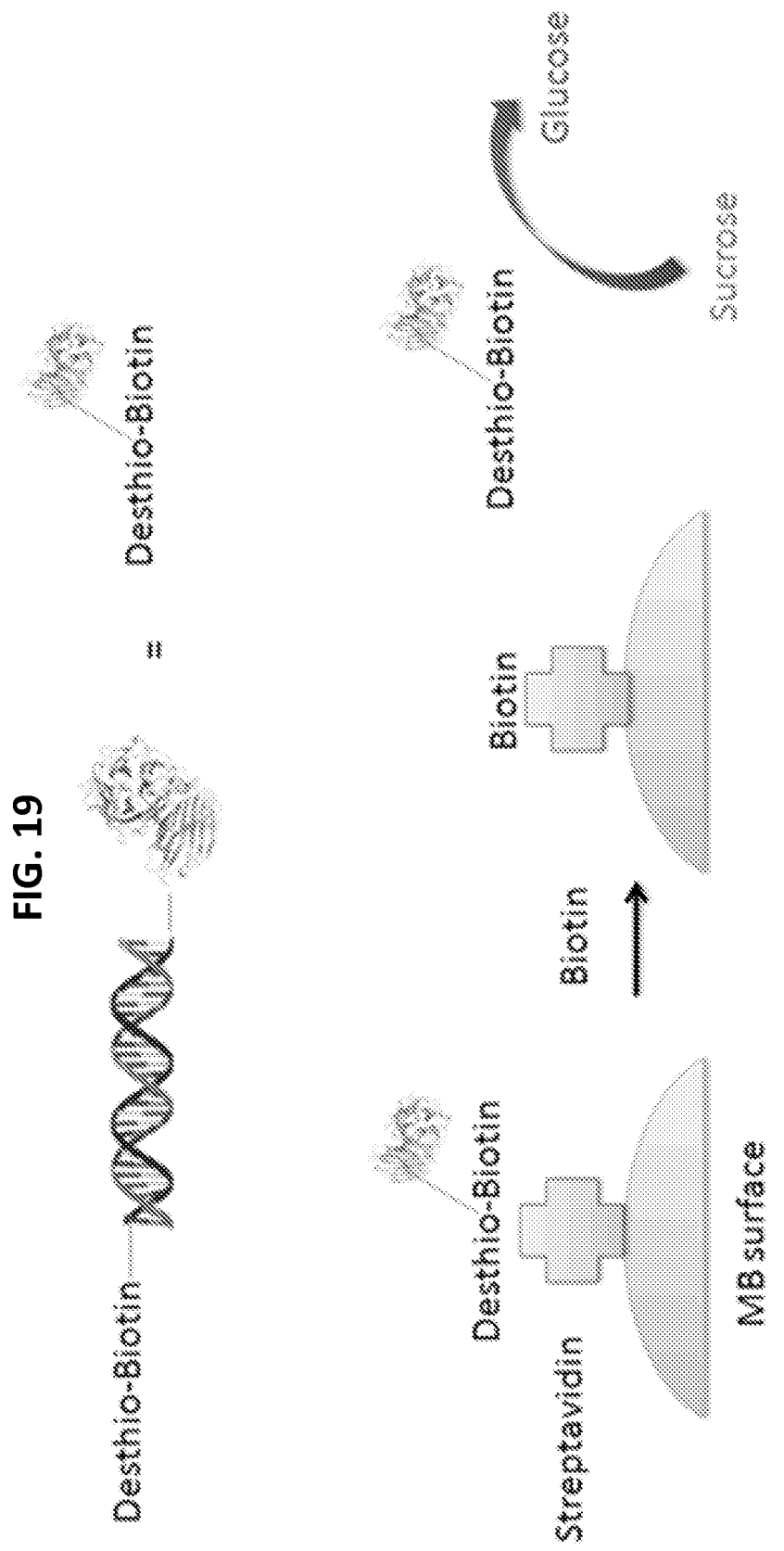
FIG. 19 is a schematic drawing showing the mechanism of biotin detection using a PGM.

As shown in FIG. 19, desthiobiotin-invertase conjugate is first immobilized to streptavidin-coated MBs. Upon the addition of target biotin, the desthiobiotin-invertase conjugate is released from the MBs because biotin has a much stronger affinity to streptavidin than its analogue dethio-biotin. The concentration of biotin in the sample is proportional to that of the released desthiobiotin-invertase conjugate, which further catalyzes the hydrolysis of sucrose to produce glucose. Thus, the read out of glucose concentration by a PGM can be used to calculate the concentration of biotin in the sample.

Result of the Biotin Detection Using a PGM

To release the invertase conjugate from the surface of MBs in the presence of target, the target should exhibit a much stronger affinity to the surface functional groups of the MBs compared to that of the invertase conjugate. Here the pair of biotin and desthiobiotin was used to demonstrate the concept. Desthiobiotin is an analogue of biotin but with several orders of magnitude lower affinity to streptavidin, thus biotin could efficiently release desthiobiotin from streptavidin even if the latter already binds with streptavidin.

Figure 20:
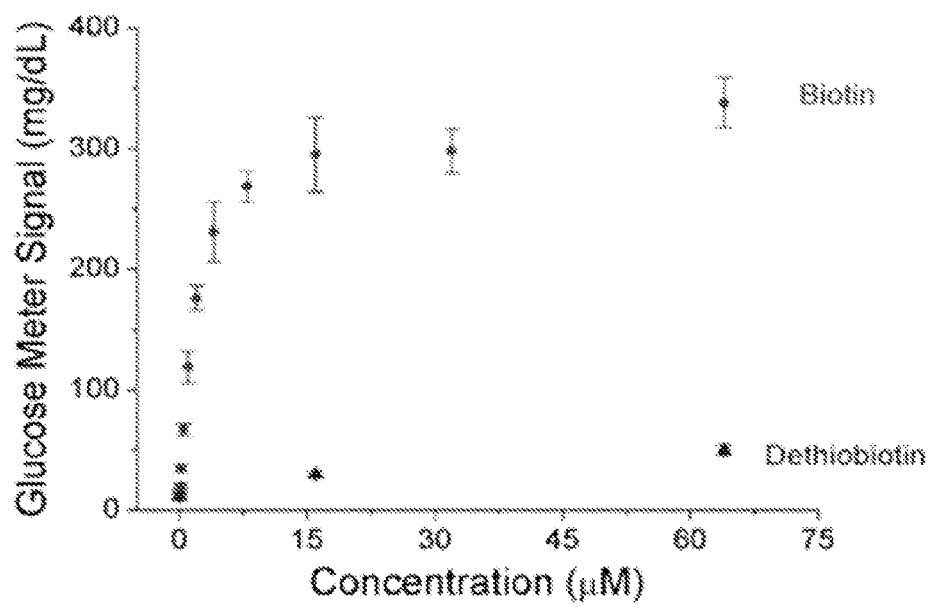
FIG. 20 is a graph showing the results of biotin detection using a PGM.

As shown in FIG. 20, in the presence of increasing amounts of biotin, more enhancement of glucose meter signal is detected by a BGM, because more desthiobiotin-invertase conjugates are released and catalyze higher amount of glucose production from sucrose. In the presence of excess biotin (1564 μM), more than 30-fold enhancement in glucose meter signal was observed. A detection limit of 0.25 μM biotin was obtained based on 3 blank measurements. The assay also showed an excellent specificity toward biotin, because the addition of desthiobiotin only had a very slight effect on the glucose meter signal enhancement. One advantage of the releasing-based immunoassay is that no washing step is required, so the assay is simpler and less time-consuming than its counterpart of binding based assay.

EXAMPLE 7

Detection of Prostate Specific Antigen (PSA) by Personal Glucose Meter (PGM)

This example describes the generation and testing of a sensor that includes antibodies to detect the target PSA as generally illustrated in FIG. 2B. One skilled in the art will appreciate that similar methods can be used to generate other antibody-based sensors to detect other target proteins.

Epoxyl-coated magnetic beads (Dynabeads M-270) conjugation kit for antibody and Amicon centrifugal filters were purchased from Invitrogen Inc. (Carlsbad, Calif.) and Millipore Inc. (Billerica, Mass.), respectively. Grade VII invertase from baker's yeast (*S. cerevisiae*), Prostate specific antigen (PSA) and other chemicals for buffers and solvents were purchased from Sigma-Aldrich, Inc. (St. Louis, Mo.). EZ-Link NHS-PEG4-Biotin and streptavidin was obtained from Pierce Inc. (Rockford, Ill.). Mouse monoclonal anti-human PSA antibody (ab403) was purchased from Abcam Inc. (Cambridge, Mass.). Biotinylated goat anti-human Kallikrein 3 IgG antibody (BAF1344) was from R&D System (Minneapolis, Minn.).

Figure 21:
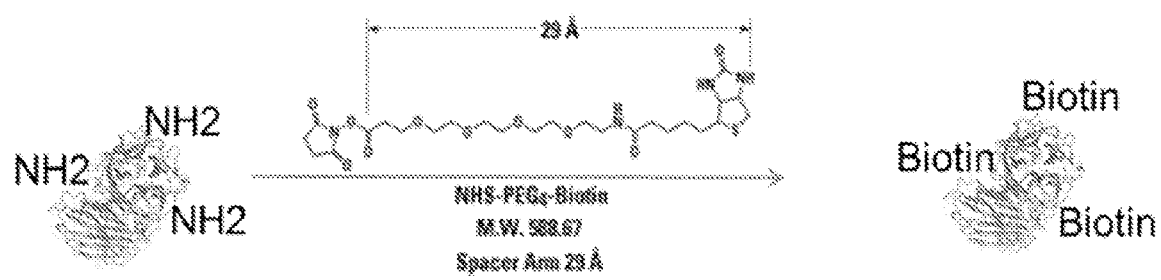
FIG. 21 is a schematic drawing showing biotin-invertase conjugation.
Figure 22:
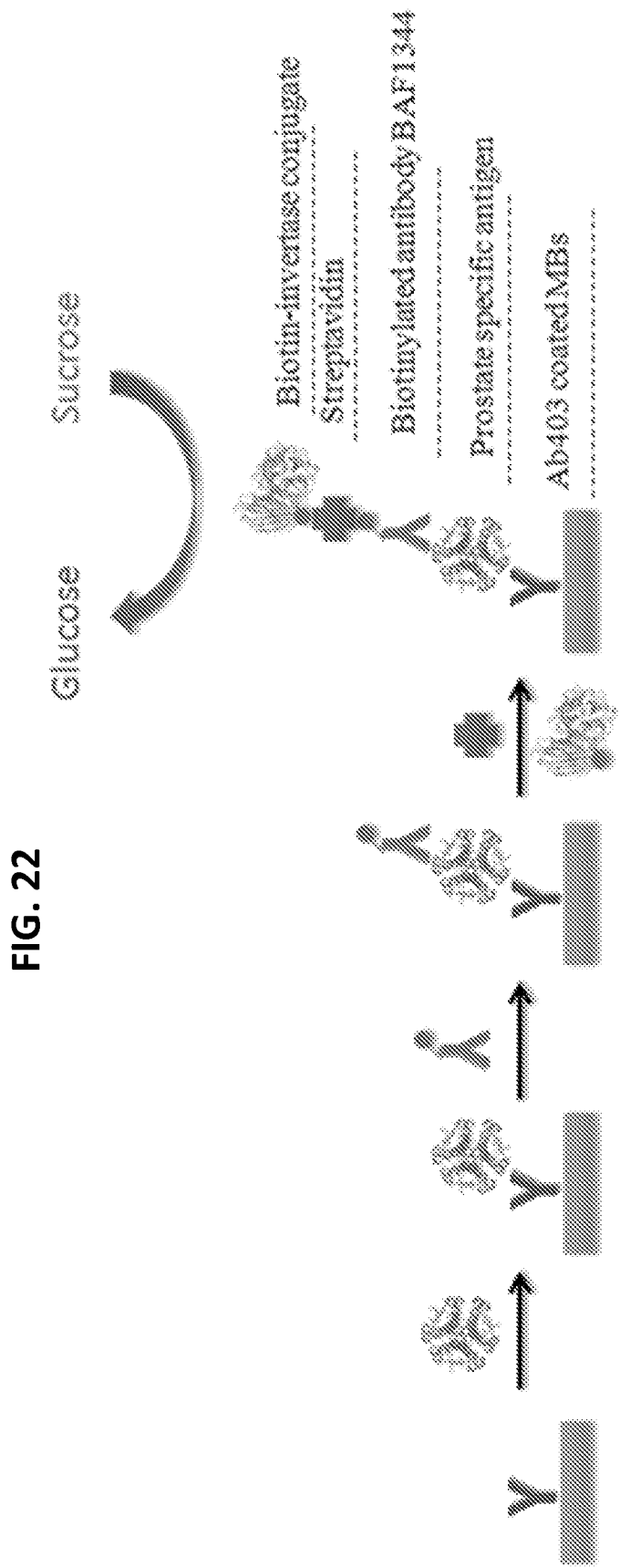
FIG. 22 is a schematic drawing showing the stepwise mechanism of PSA detection by a glucose meter.
Figures 23A, 23B:
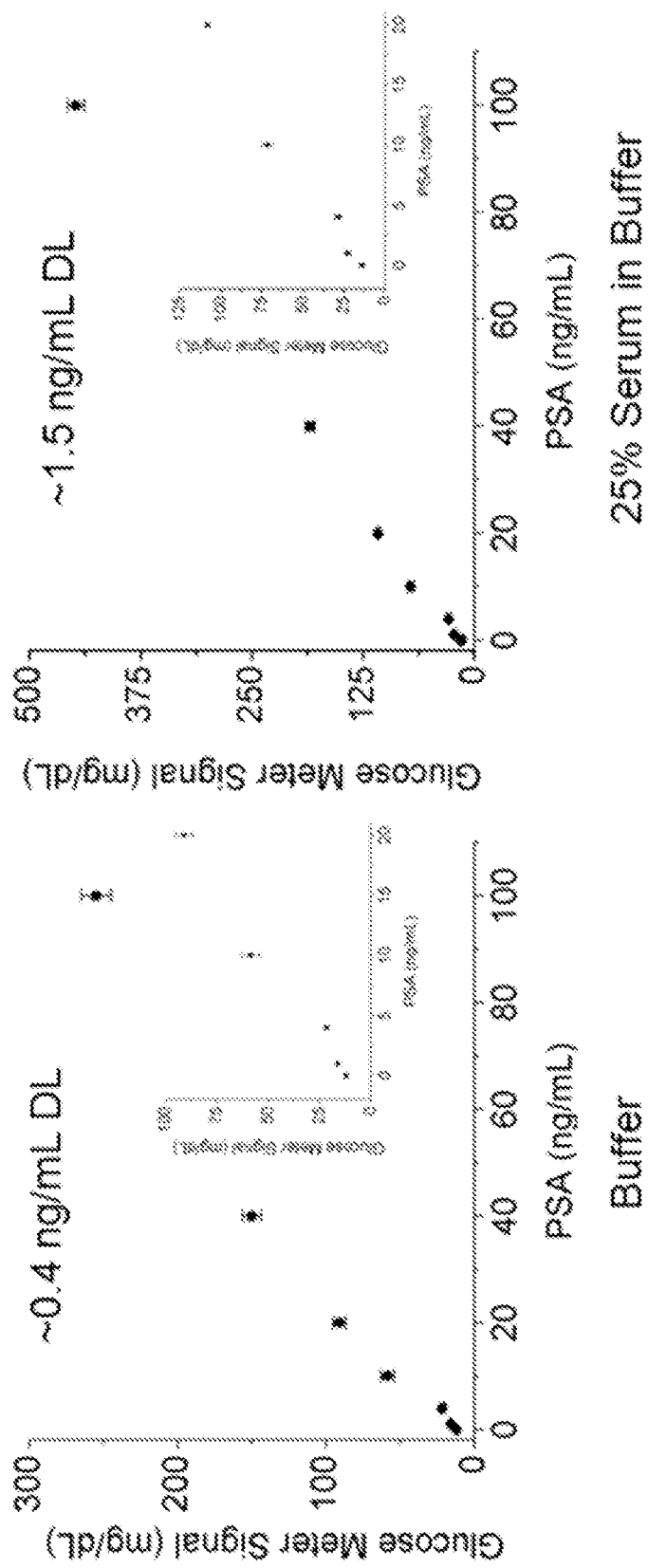
FIGS. 23A and B are graphs showing the quantification of (A) PSA in Buffer B and (B) 25% human serum in Buffer B using a PGM.

Buffer A: 0.1 M NaCl, 0.2 M sodium phosphate buffer, pH 7.3, 0.05% Tween-20
Buffer B: PBS buffer, pH 7.0, 0.1 g/L BSA, 0.025% Tween-20.
Conjugation Chemistry:
(1) Biotin-Invertase Conjugation (FIG. 21):

To 1 mL 20 mg/mL invertase in Buffer A without Tween-20, about 5 mg EZ-Link NHS-PEG4-Biotin was added and the mixture was well mixed at room temperature for 4 h. Then, the Biotin-invertase conjugate was purified by Amicon-100K for 8 times using Buffer A without Tween-20.
(2) Anti-PSA Antibody Conjugation to Magnetic Beads (FIG. 21):

This was done following the protocol provided by the supplier (solution C1, C2, HB, LB and SB were all from the kit provided by the supplier): To a mixture of 200 μL solution C1 and 250 μL solution C2, 5 mg Dynabeads M-270 (after wash by 1 mL solution C1) and 50 mg ab403 antibody were added, well mixed, and kept on a roller at room temperature for 1 day. Then, the Dynabeads M-270 magnetic beads (MBs) were separated by a magnet and the supernatant was removed. The MBs were further dispersed in 800 μL solution HB, and then separated by a magnet and supernatant removed. This step was repeated using equal amount of solution LB, SB and SB instead of HB, respectively. Finally, the MBs were dispersed in 1 mL solution SB to give a concentration of 5 mg/mL.
PSA Detection Using a PGM The PSA antibody conjugated MBs were buffer-changed to Buffer B to reach a final concentration of 3 mg/mL. Each 50 μL of this solution was then used for one assay. After separated by a magnet and with supernatant removed, the MBs were dispersed in different concentrations of PSA in 50 μL Buffer B or 25% human serum in Buffer B and then kept in a roller for 1 h at room temperature. Then, the MBs were separated and the supernatant was removed. The solid residue was added 50 μL 1 mg/L BAF1344 antibody in Buffer B, followed by mixing at room temperature for 0.5 h. The MBs were further separated, dispersed in 50 μL 2 μM streptavidin, and then mixed and left on a roller for 0.5 hour. Later, the MBs were separated again and dispersed in 50 μL 4 μM Biotin-invertase conjugate in Buffer B. After mixing for 0.5 hour at room temperature on a roller, the MBs were separated from the supernatant and washed by Buffer B for 4 times. Finally, 50 μL 0.5 M sucrose in Buffer B was added to the MBs, and 5 μL of the solution was tested by a PGM after 4 h.
Principle of Detection As shown in FIG. 22, the Ab403 anti-PSA antibody coated MBs is first treated by the sample with/without PSA. Then, BAF1344 antibody, which binds PSA at a different site from Ab403, is added to form a sandwich complex. Because the BAF1344 antibody is biotinylated, the subsequent addition of streptavidin and biotin-invertase conjugate finally results in the structure shown on the right of FIG. 22. The immobilized invertase conjugate can catalyze the production of glucose from sucrose, and the amount of glucose detected by a PGM can be used to calculate the concentration of PSA in the sample.
Result of the PSA Detection Using a PGM The PSA detection using the MBs-based detection method was carried out in both Buffer B and 25% human serum (diluted by Buffer B). As shown in FIGS. 23A and 23B, in both cases, increasing amount of PSA in the sample resulted in a higher glucose read out in the PGM, with a close-to-linear relationship at least within the range of 0~100 ng/mL PSA. Detection limits of 0.4 ng/mL and 1.5 ng/mL were obtained for the PSA detections in Buffer B and 25% human serum, respectively. Because high concentrations of BSA and human serum albumin (HSA) are in Buffer B and human serum respectively, the result indicates the detection is very sensitive to PSA and not affected by BSA and HSA as controls. In addition, the ng/mL level detection limit indicates the method can be used to detect PSA for diagnosis of prostate cancer.

EXAMPLE 8

Lateral Flow Device

Figure 5A:
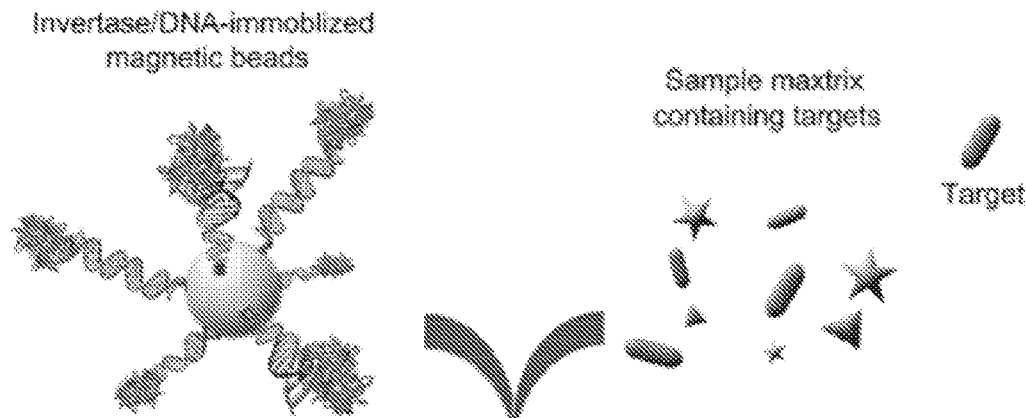
FIGS. 5A-5C are schematic drawings showing an exemplary mechanism of analyte detection using a glucose meter based on the interaction between functional DNA and the corresponding target agent. (A) DNA-invertase conjugate is immobilized to magnetic beads via DNA hybridization with functional DNA that can specifically response to the target of interest. (B) Upon the addition of a sample containing the target agent, the interaction between functional DNA and the target agent perturbs DNA hybridization and causes the release of DNA-invertase conjugate from magnetic beads into solution. (C) After removal of magnetic beads by a magnet, the DNA-invertase conjugate in solution can efficiently catalyze the hydrolysis of sucrose into glucose, which is quantified by a glucose meter. The DNA-invertase conjugate released in solution is proportional to the concentration of the target agent present in the sample. Therefore the read out by the glucose meter can be used to quantify the concentration of target agent.

This example describes an exemplary lateral flow device that can be used to detect a target agent in a test sample using the sensors disclosed herein. One skilled in the art will appreciate that similar devices can be generated by attaching other recognition molecules and by using other enzymes that catalyze the conversion of a substance into glucose. For example, the lateral flow device described in this example uses an aptamer-invertase conjugate (such as shown in FIG. 5A); however, the sensor may use antibodies or other recognition molecules (such as DNA) instead of aptamers.

FIG. 24 shows a lateral flow device that can be read by a BGM for detecting a broad range of non-glucose targets in many different samples, using a lateral flow device containing an aptamer-invertase conjugate. The aptamer-invertase conjugate is prepared by chemical conjugation between the nucleic acid and enzyme.[51] Invertase is an enzyme that can catalyze the conversion of sucrose into glucose.

As shown in FIG. 24, the lateral flow device contains wicking pad, conjugation pad, membrane, and absorption pad. The sample containing or suspected of containing one or more target agents is applied to the wicking pad. If desired, liquid can be added to the sample, or the sample can be concentrated, before applying it to the wicking pad. The wicking pad ensures a controllable (unilateral) flow of the sample. The sample migrates from the bottom to the top of the lateral flow device following the indicated flow direction in FIG. 24 because of capillary force. When the target agent in the sample reaches the conjugation pad, the aptamer-invertase (or other recognition molecule-enzyme that can catalyze the conversion of a substance (such as sucrose) into glucose) conjugated to the conjugation pad recognizes the target agent, and releases the aptamer-invertase from the conjugation pad to the mobile phase because the aptamer has a higher affinity to the target agent than the immobilized surface (for example, the surface is modified by the target agent's analogue of lower binding affinity). Then, the released aptamer-invertase or invertase alone (or other recognition molecule-enzyme that can catalyze the conversion of a substance (such as sucrose) into glucose) moves with the flow and catalyzes the production of glucose from sucrose (or other substance that can be converted into glucose) in the membrane part coated by sucrose. Finally, the produced glucose moves with the flow and reaches the absorption pad, where it is then detected by a connected BGM.

The amount of glucose detected by BGM, aptamer-invertase released and target agent are proportional to each other. This permits quantification of the target agent by the read-out of glucose meter. The original glucose concentration in the sample can be subtracted from the result for the quantification of target agents. Because of high selectivity of the aptamer for its target, interference by other components in the sample is minimal.

Figure 5B:
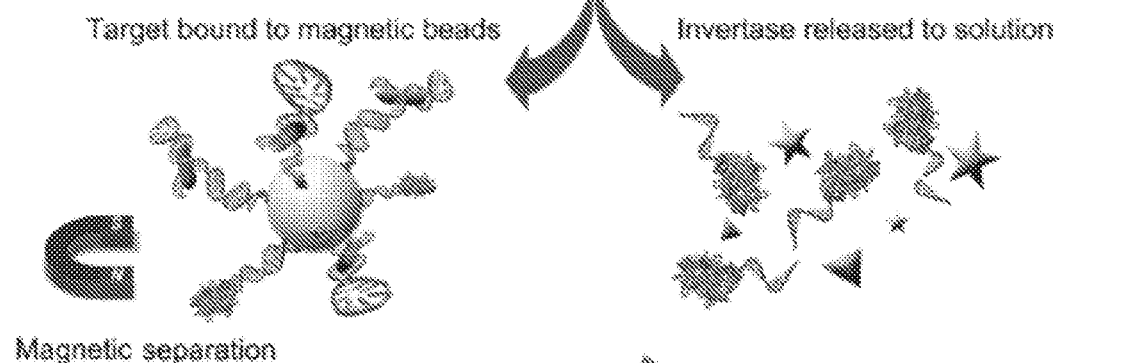
Figure 5C:
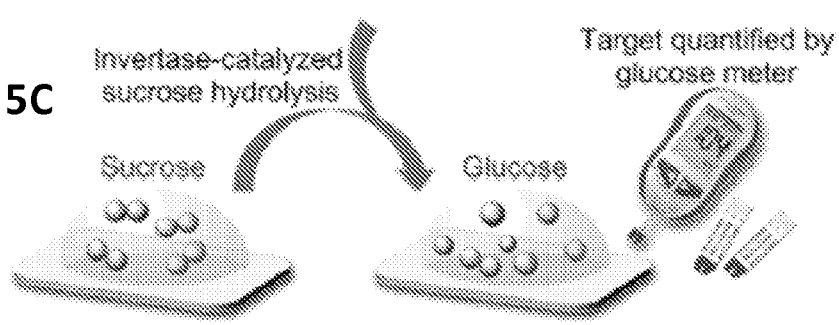

FIGS. 5A-C show more details of the specific interaction between the targets in sample with the aptamer-invertase conjugate in the conjugation pad, which results in the release of the invertase to the mobile phase.

REFERENCES (1) Drummond, T. G.; Hill, M. G.; Barton, J. K. *Nat. Biotechnol.* 2003, 21, 1192-9.
(2) Wang, J.; Musameh, M. *Anal. Chem.* 2003, 75, 2075-2079.
(3) Tan, W. H.; Wang, K. M.; Drake, T. J. *Curr. Opin. Chem. Biol.* 2004, 8, 547-53.
(4) Chen, P. R.; He, C. *Curr. Opin. Chem. Biol.* 2008, 12, 214-221.
(5) Nolan, E. M.; Lippard, S. J. *Chem. Rev.* 2008, 108, 3443-3480.
(6) Que, E. L.; Domaille, D. W.; Chang, C. J. *Chem. Rev.* 2008, 108, 1517-1549.
(7) Que, E. L.; Chang, C. J. *Chem. Soc. Rev.* 2010, 39, 51-60.
(8) Montagnana, M.; Caputo, M.; Giavarina, D.; Lippi, G. *Clin. Chim. Acta* 2009, 402, 7-13.
(9) Lee, T. M. H. *Sensors* 2008, 8, 5535-5559.
(10) Lee, J.-S.; Han, M. S.; Mirkin, C. A. *Angew. Chem., Int. Ed.* 2007, 46, 4093-4096.
(11) Huang, C.-C.; Huang, Y.-F.; Cao, Z.; Tan, W.; Chang, H.-T. *Anal. Chem.* 2005, 77, 5735-5741.
(12) Liu, J.; Lu, Y. *J. Am. Chem. Soc.* 2003, 125, 6642-6643.
(13) Liu, J.; Lu, Y. *Angew. Chem., Int. Ed.* 2006, 45, 90-94.
(14) Liu, J.; Cao, Z.; Lu, Y. *Chem. Rev.* 2009, 109, 1948-1998.
(15) Breaker, R. R.; Joyce, G. F. *Chem. Biol.* 1994, 1, 223-229.
(16) Carmi, N.; Shultz, L. A.; Breaker, R. R. *Chem. Biol.* 1996, 3, 1039-1046.
(17) Ellington, A. D.; Szostak, J. W. *Nature* 1990, 346, 818-822.
(18) Tuerk, C.; Gold, L. *Science* 1990, 249, 505-510.
(19) Lee, J. F.; Hesselberth, J. R.; Meyers, L. A.; Ellington, A. D. *Nucleic Acids Res.* 2004, 32, D95-D100.
(20) Breaker, R. R. *Curr. Opin. Biotechnol.* 2002, 13, 31-39.
(21) Willner, I.; Shlyahovsky, B.; Zayats, M.; Willner, B. *Chem. Soc. Rev.* 2008, 37, 1153-1165.
(22) Li, Y.; Lu, Y. *Functional Nucleic Acids for Sensing and Other Analytical Applications*; Springer: New York, 2009.
(23) Sefah, K.; Phillips, J. A.; Xiong, X. L.; Meng, L.; Van Simaeys, D.; Chen, H.; Martin, J.; Tan, W. H. *Analyst* 2009, 134, 1765-1775.
(24) Song, S.; Wang, L.; Li, J.; Fan, C.; Zhao, J. *TrAC, Trends Anal. Chem.* 2008, 27, 108-117.
(25) Yang, L.; Ellington, A. D. *Fluoresc. Sens. Biosens.* 2006, 5-43.
(26) Navani, N. K.; Li, Y. *Curr. Opin. Chem. Biol.* 2006, 10, 272-281.
(27) Cho, E. J.; Rajendran, M.; Ellington, A. D. *Top. Fluoresc. Spectrosc.* 2005, 10, 127-155.
(28) Rajendran, M.; Ellington, A. D. *Comb. Chem. High Throughput Screening* 2002, 5, 263-270.
(29) Liu, J.; Lu, Y. *J. Fluoresc.* 2004, 14, 343-354.
(30) Zhao, W.; Brook, M. A.; Li, Y. F. *ChemBioChem* 2008, 9, 2363-2371.
(31) Xu, W.; Xue, X.; Li, T.; Zeng, H.; Liu, X. *Angew. Chem., Int. Ed.* 2009, 48, 6849-6852.
(32) Freeman, R.; Sharon, E.; Tel-Vered, R.; Willner, I. *J. Am. Chem. Soc.* 2009, 131, 5028-5029.
(33) Xue, X.; Wang, F.; Liu, X. *J. Am. Chem. Soc.* 2008, 130, 3244-3245.
(34) Ono, A.; Togashi, H. *Angew. Chem., Int. Ed.* 2004, 43, 4300-4302.
(35) Liu, J.; Lu, Y. *Methods Mol. Biol.* 2006, 335, 275-288.
(36) Nutiu, R.; Li, Y. *Methods* 2005, 37, 16-25.
(37) Nutiu, R.; Li, Y. *Angew. Chem., Int. Ed.* 2005, 44, 1061-1065.
(38) Nutiu, R.; Li, Y. *J. Am. Chem. Soc.* 2003, 125, 4771-4778.
(39) Xiao, Y.; Rowe, A. A.; Plaxco, K. W. *J. Am. Chem. Soc.* 2007, 129, 262-263.
(40) Willner, I.; Zayats, M. *Angew. Chem., Int. Ed.* 2007, 46, 6408-6418.
(41) Zuo, X.; Xiao, Y.; Plaxco, K. W. *J. Am. Chem. Soc.* 2009, 131, 6944-6945.
(42) Wu, Z.; Zhen, Z.; Jiang, J.-H.; Shen, G.-L.; Yu, R.-Q. *J. Am. Chem. Soc.* 2009, 131, 12325-12332.
(43) Swensen, J. S.; Xiao, Y.; Ferguson, B. S.; Lubin, A. A.; Lai, R. Y.; Heeger, A. J.; Plaxco, K. W.; Soh, H. T. *J. Am. Chem. Soc.* 2009, 131, 4262-4266.
(44) Zuo, X.; Song, S.; Zhang, J.; Pan, D.; Wang, L.; Fan, C. *J. Am. Chem. Soc.* 2007, 129, 1042-1043.
(45) Yigit, M. V.; Mazumdar, D.; Lu, Y. *Bioconjugate Chem.* 2008, 19, 412-417.
(46) Huizenga, D. E.; Szostak, J. W. *Biochemistry* 1995, 34, 656-665.
(47) Boehm, U.; Klamp, T.; Groot, M.; Howard, J. C. *Annu. Rev. Immunol.* 1997, 15, 749-795.
(48) Pai, M.; Riley, L. W.; Colford, J. M. *Lancet Infect. Dis.* 2004, 4, 761-776.
(49) Liu, J.; Brown, A. K.; Meng, X.; Cropek, D. M.; Istok, J. D.; Watson, D. B.; Lu, Y. *Proc. Nat. Acad. Sci. U.S.A.* 2007, 104, 2056-2061.
(50) Koshland, D. E.; Stein, S. S. *J. Biol. Chem.* 1954, 208, 139-148.
(51) Niemeyer, C. M. *Angew. Chem., Int. Ed.* 2010, 49, 1200-1216.
(52) Niemeyer, C. M. *Nano Today* 2007, 2, 42-52.
(53) Niemeyer, C. M. *Trends Biotechnol.* 2002, 20, 395-401.

(54) Reddy, A.; Maley, F. *J. Biol. Chem.* 1996, 271, 13953-13958.
(55) Reddy, V. A.; Maley, F. *J. Biol. Chem.* 1990, 265, 10817-10820.
(56) Hermanson, G. T. Bioconjugate Techniques; Elsevier: London, 2008.
(57) Danielli, A.; Porat, N.; Ehrlich, M.; Arie, A. *Curr. Pharm. Biotechnol.* 2010, 11, 128-137.
(58) Tamanaha, C. R.; Mulvaney, S. P.; Rife, J. C.; Whitman, L. J. *Biosens. Bioelectron.* 2008, 24, 1-13.
(59) Wang, J.; Xu, D. K.; Kawde, A. N.; Polsky, R. *Anal. Chem.* 2001, 73, 5576-81.
(60) Wang, J.; Kawde, A. N.; Erdem, A.; Salazar, M. *Analyst* 2001, 126, 2020-2024.
(61) Xiang, Y.; Tong, A.; Lu, Y. *J. Am. Chem. Soc.* 2009, 131, 15352-15357.
(62) Lee, P. P.; Ramanathan, M.; Hunt, C. A.; Garovoy, M. R. *Transplantation* 1996, 62, 1297-1301.
(63) Balasubrananian, V.; Nguyen, L. T.; Balasubramanian, S. V.; Ramanathan, M. *Mol. Pharmacol.* 1998, 53, 926-932.
(64) Tuleuova, N.; Jones, C. N.; Yan, J.; Ramanculov, E.; Yokobayashi, Y.; Revzin, A. *Anal. Chem.* 2010, 82, 1851-1857.
(65) Lee, J. H.; Wang, Z.; Liu, J.; Lu, Y. *J. Am. Chem. Soc.* 2008, 130, 14217-14226.
(66) Brown, A. K.; Liu, J.; He, Y.; Lu, Y. *ChemBioChem* 2009, 10, 486-492.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

---

We claim:

1. A lateral flow device, comprising:
   a first solid support to which is attached a first nucleic acid molecule that specifically binds to a target agent but not significantly to other agents;
   an enzyme attached to second nucleic acid molecule, wherein the second nucleic acid molecule is complementary to a portion of the first nucleic acid molecule, thereby generating an enzyme conjugate, wherein the enzyme conjugate is hybridized to the first nucleic acid molecule, wherein the enzyme catalyzes the conversion of a substance into glucose, and wherein in the presence of the target agent the enzyme conjugate is released and separated from the first nucleic acid molecule, and the enzyme converts the substance into glucose; and
   the substance that is converted into glucose by the enzyme, wherein the substance is soluble and attached to a second solid support.

2. The lateral flow device of claim 1, wherein the first solid support comprises a bead and a conjugation pad, wherein the first nucleic acid molecule is attached directly to the bead, and wherein the bead is adsorbed to the conjugation pad.

3. The lateral flow device of claim 1, wherein the first and/or the second solid support comprises nitrocellulose.

4. The lateral flow device of claim 1, wherein the target agent comprises a metal ion, microbe, cytokine, hormone, cell, nucleic acid molecule, spore, protein, recreational drug, or toxin.

5. The lateral flow device of claim 1, wherein:
   the enzyme is an invertase, sucrase, or sucrase-isomaltase and the substance is sucrose,
   the enzyme is a maltase and the substance is maltose,
   the enzyme is a trehalase and the substance is trehalose,
   the enzyme is an amylase and the substance is starch, or
   the enzyme is a cellulase and the substance is cellulose.

6. The lateral flow device of claim 1, wherein:
   the first solid support comprises a conjugation pad;
   the second solid support comprises a membrane; and
   the lateral flow device further comprises:
      a sample or wicking pad; and
      an absorption pad.

7. The lateral flow device of claim 6, wherein the enzyme is invertase and the substance that is converted into glucose is sucrose.

8. The lateral flow device of claim 1, wherein the first nucleic acid is an enzyme strand and the second nucleic acid is a substrate strand of a DNAzyme or aptazyme.

9. The lateral flow device of claim 4, wherein the metal ion is a heavy metal.

10. The lateral flow device of claim 9, wherein the heavy metal is mercury ($Hg^{2+}$), cadmium ($Cd^{2+}$), arsenic ($As^{2+/3+}$), chromium ($Cr^{5+/6+}$), thallium ($Tl^{+/3+}$), uranium ($UO_2^{2+}$), plutonium ($Pu^{3+/4+}$, $PuO^{2+}$, $PuO_2^{2+}$, $PuO_5^{2+}$), or lead ($Pb^{2+}$).

11. The lateral flow device of claim 4, wherein the metal ion is a nutritional metal.

12. The lateral flow device of claim 11, wherein the nutritional metal is calcium ($Ca^{2+}$), iron ($Fe^{3+/4+}$), cobalt ($Co^{2+}$), magnesium ($Mg^{2+}$), manganese ($Mn^{2+}$), molybdenum ($MoO_4^{2+}$), zinc ($Zn^{2+}$), cadmium ($Cd^{2+}$), or copper ($Cu^{+/2+}$).

13. A kit comprising:
   one or more lateral flow devices of claim 1; and
   one or more of a buffer or a chart for correlating detected glucose level and amount of target agent present.

14. A method for detecting a target agent, comprising:
   contacting one or more lateral flow devices of claim 1 with a sample under conditions sufficient to allow the target agent in the sample to flow through the lateral flow device and bind to the first nucleic acid molecule present on the first solid support;
   forming a target agent-nucleic acid complex, wherein formation of the target agent-nucleic acid complex results in the release of the enzyme conjugate from the first nucleic acid molecule;
   allowing the enzyme of the enzyme conjugate to interact with the substance that is converted into glucose, thereby generating glucose; and
   detecting glucose, wherein detection of glucose indicates the presence of the target agent in the sample, and an absence of detected glucose indicates the absence of the target agent in the sample.

15. The method of claim 14, further comprising quantifying the target agent, wherein a level of glucose detected indicates an amount of target agent present.

16. The method of claim 14, wherein
   the enzyme comprises invertase, sucrase, or sucrase-isomaltase and the substance that the enzyme converts into glucose comprises sucrose, or
   the enzyme comprises maltase and the substance that the enzyme converts into glucose comprises maltose, or
   the enzyme comprises trehalase and the substance that the enzyme converts into glucose comprises trehalose, or
   the enzyme comprises cellulase and the substance that the enzyme converts into glucose comprises cellulose, or
   the enzyme comprises amylase and the substance that the enzyme converts into glucose comprises starch.

17. The method of claim 14, wherein the glucose is detected using a personal glucose meter.

18. A lateral flow device, comprising:
   a first region of a solid support to which is attached a first nucleic acid molecule that specifically binds to a target agent but not significantly to other agents;
   an enzyme attached to a second nucleic acid molecule, wherein the second nucleic acid molecule is complementary to a portion of the first nucleic acid molecule, thereby generating an enzyme-conjugate, wherein the enzyme-conjugate is hybridized to the first nucleic acid molecule, wherein the enzyme catalyzes the conversion of a substance into glucose, and wherein in the presence of the target agent the enzyme-conjugate is released and separated from the first nucleic acid molecule, and the enzyme converts the substance into glucose; and
   the substance that is converted into glucose by the enzyme, wherein the substance is soluble and attached to a second region of the solid support.

19. The lateral flow device of claim 18, wherein the first nucleic acid is an enzyme strand and the second nucleic acid is a substrate strand of a DNAzyme or aptazyme.

20. The lateral flow device of claim 18, wherein the target agent comprises a metal ion, microbe, cytokine, hormone, cell, nucleic acid molecule, spore, protein, recreational drug, or toxin.

21. The lateral flow device of claim 18, wherein the solid support comprises a membrane, and wherein the nucleic acid molecule is attached directly to the membrane.

22. The lateral flow device of claim 18, wherein:
   the enzyme is an invertase, sucrase, or sucrase-isomaltase and the substance is sucrose,
   the enzyme is a maltase and the substance is maltose,
   the enzyme is a trehalase and the substance is trehalose,
   the enzyme is an amylase and the substance is starch, or
   the enzyme is a cellulase and the substance is cellulose.

23. A method for detecting a target agent, comprising:
contacting one or more lateral flow devices of claim 18 with a sample under conditions sufficient to allow the target agent in the sample to flow through the lateral flow device and bind to the first nucleic acid molecule present on the solid support;
forming a target agent-nucleic acid complex, wherein formation of the target agent-nucleic acid complex results in the release of the enzyme-conjugate from the first nucleic acid molecule;
allowing the enzyme of the enzyme-conjugate to interact with the substance that is converted into glucose, thereby generating glucose; and
detecting glucose, wherein detection of glucose indicates the presence of the target agent in the sample, and an absence of detected glucose indicates the absence of the target agent in the sample.

24. A lateral flow device, comprising:
a first region of a solid support to which is attached a nucleic acid molecule that specifically binds to a target agent but not significantly to other agents;
an enzyme attached to an analogue of the target agent, thereby generating an enzyme-analog conjugate, wherein the enzyme-analog conjugate is bound to the nucleic acid molecule, wherein the enzyme catalyzes the conversion of a substance into glucose, and wherein in the presence of the target agent the enzyme-analog conjugate is released and separated from the nucleic acid molecule, and the enzyme converts the substance into glucose; and
the substance that is converted into glucose by the enzyme, wherein the substance is soluble and attached to a second region of the solid support.

25. The lateral flow device of claim 24, wherein the nucleic acid molecule is an aptamer.

26. The lateral flow device of claim 24, wherein the target agent comprises a metal ion, microbe, cytokine, hormone, cell, nucleic acid moleucle, spore, protein, recreational drug, or toxin.

27. The lateral flow device of claim 24, wherein:
the enzyme is an invertase, sucrase, or sucrase-isomaltase and the substance is sucrose,
the enzyme is a maltase and the substance is maltose,
the enzyme is a trehalase and the substance is trehalose,
the enzyme is an amylase and the substance is starch, or
the enzyme is a cellulase and the substance is cellulose.

28. The lateral flow device of claim 24, wherein the solid support comprises a membrane, and wherein the nucleic acid molecule is attached directly to the membrane.

29. A method for detecting a target agent, comprising:
contacting one or more lateral flow devices of claim 24 with a sample under conditions sufficient to allow the target agent in the sample to flow through the lateral flow device and bind to the nucleic acid molecule present on the solid support;
forming a target agent-nucleic acid complex, wherein formation of the target agent-nucleic acid complex results in the release of the enzyme-analog conjugate from the nucleic acid molecule;
allowing the enzyme of the enzyme-analog conjugate to interact with the substance that is converted into glucose, thereby generating glucose; and
detecting glucose, wherein detection of glucose indicates the presence of the target agent in the sample, and an absence of detected glucose indicates the absence of the target agent in the sample.

30. A lateral flow device, comprising:
a first solid support to which is attached a nucleic acid molecule that specifically binds to a target agent but not significantly to other agents;
an enzyme attached to an analogue of the target agent, thereby generating an enzyme-analog conjugate, wherein the enzyme-analog conjugate is bound to the nucleic acid molecule, wherein the enzyme catalyzes the conversion of a substance into glucose, and wherein in the presence of the target agent the enzyme-conjugate is released and separated from the nucleic acid molecule, and the enzyme converts the substance into glucose; and
the substance that is converted into glucose by the enzyme, wherein the substance is soluble and attached to a second solid support.

31. The lateral flow device of claim 30, wherein the nucleic acid molecule is an aptamer.

32. The lateral flow device of claim 30, wherein the target agent comprises a metal ion, microbe, cytokine, hormone, cell, nucleic acid moleucle, spore, protein, recreational drug, or toxin.

33. The lateral flow device of claim 30, wherein:
the enzyme is an invertase, sucrase, or sucrase-isomaltase and the substance is sucrose,
the enzyme is a maltase and the substance is maltose,
the enzyme is a trehalase and the substance is trehalose,
the enzyme is an amylase and the substance is starch, or
the enzyme is a cellulase and the substance is cellulose.

34. The lateral flow device of claim 30, wherein the first solid support comprises a bead and a conjugation pad, wherein the nucleic acid molecule is attached directly to the bead, which is adsorbed to the conjugation pad.

35. A method for detecting a target agent, comprising:
contacting one or more lateral flow devices of claim 30 with a sample under conditions sufficient to allow the target agent in the sample to flow through the lateral flow device and bind to the nucleic acid molecule present on the solid support;
forming a target agent-nucleic acid complex, wherein formation of the target agent-nucleic acid complex results in the release of the enzyme-analog conjugate from the nucleic acid molecule;
allowing the enzyme of the enzyme-analog conjugate to interact with the substance that is converted into glucose, thereby generating glucose; and
detecting glucose, wherein detection of glucose indicates the presence of the target agent in the sample, and an absence of detected glucose indicates the absence of the target agent in the sample.

* * * * *

UNITED STATES PATENT AND TRADEMARK OFFICE
CERTIFICATE OF CORRECTION

PATENT NO. : 8,945,943 B2
APPLICATION NO. : 13/699578
DATED : February 3, 2015
INVENTOR(S) : Yi Lu et al.

Page 1 of 1

It is certified that error appears in the above-identified patent and that said Letters Patent is hereby corrected as shown below:

In the Claims:

Column 57, line 6, claim 1, "to second" should be --to a second--.

Column 60, line 28, claim 32, "moleucle" should be --molecule--.

Signed and Sealed this
Tenth Day of May, 2016

Michelle K. Lee
*Director of the United States Patent and Trademark Office*